United States Patent
Man et al.

(10) Patent No.: US 7,799,819 B2
(45) Date of Patent: Sep. 21, 2010

(54) 7-AMIDO-ISOINDOLYL COMPOUNDS AND THEIR PHARMACEUTICAL USES

(75) Inventors: Hon-Wah Man, Princeton, NJ (US); George W. Muller, Bridgewater, NJ (US); Weihong Zhang, Highland Park, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 12/357,355

(22) Filed: Jan. 21, 2009

(65) Prior Publication Data

US 2009/0131505 A1   May 21, 2009

Related U.S. Application Data

(60) Continuation of application No. 11/818,927, filed on Jun. 15, 2007, now Pat. No. 7,511,072, which is a division of application No. 11/250,408, filed on Oct. 17, 2005, now Pat. No. 7,256,210, which is a division of application No. 10/798,317, filed on Mar. 12, 2004, now Pat. No. 7,034,052.

(60) Provisional application No. 60/454,155, filed on Mar. 12, 2003.

(51) Int. Cl.
*A61K 31/41* (2006.01)
*C07D 207/00* (2006.01)

(52) U.S. Cl. .................. 514/408; 514/415; 548/400; 548/452

(58) Field of Classification Search .................. 514/408; 548/400

See application file for complete search history.

(56) References Cited

U.S. PATENT DOCUMENTS

| 6,204,275 | B1 | 3/2001 | Friesen et al. |
| 6,326,378 | B1 | 12/2001 | Friebe et al. |
| 7,256,210 | B2 * | 8/2007 | Man et al. ............. 514/415 |
| 7,511,072 | B2 * | 3/2009 | Man et al. ............. 514/415 |

FOREIGN PATENT DOCUMENTS

| WO | WO 99/06041 | 2/1999 |
| WO | WO 00/25777 | 5/2000 |
| WO | WO 01/34606 | 5/2001 |
| WO | WO 01/45702 | 6/2001 |

OTHER PUBLICATIONS

Frydoonfar, et al., Colorectal Disease, vol. 4, May 2002, pp. 205-207, especially p. 207.*
Ogawa, et al., Blood, May 1, 2002, vol. 99(9), pp. 3390-3397, especially p. 3395.*
Zhang et al., "Effects of the novel PDE4 inhibitors MEM1018 and MEM1091 on memory in the radial-arm maze and inhibitory avoidance tests in rats," Psychopharm. (2005) 179: 613-19.

* cited by examiner

*Primary Examiner*—Susannah Chung
(74) *Attorney, Agent, or Firm*—Jones Day

(57) ABSTRACT

The invention encompasses 7-amido-isoindolyl compounds and methods of using these compounds and compositions in mammals for treatment, prevention or management of various diseases and disorders. Examples include, but are not limited to, cancer, inflammatory bowel disease and myelodysplastic syndrome.

3 Claims, No Drawings ations of U.S. application Ser. No. 11/818,927, filed Jun. 15, 2007, now U.S. Pat. No. 7,511,072, which is a division of U.S. application Ser. No. 11/250,408, filed Oct. 17, 2005, now U.S. Pat. No. 7,256,210, which is a division of U.S. application Ser. No. 10/798,317, filed Mar. 12, 2004, now U.S. Pat. No. 7,034,052, which claims the benefit of U.S. Provisional Application No. 60/454,155, filed Mar. 12, 2003, all of which are incorporated herein in their entireties by reference.

7-AMIDO-ISOINDOLYL COMPOUNDS AND THEIR PHARMACEUTICAL USES

This application is a continuation of U.S. application Ser. No. 11/818,927, filed Jun. 15, 2007, now U.S. Pat. No. 7,511,072, which is a division of U.S. application Ser. No. 11/250,408, filed Oct. 17, 2005, now U.S. Pat. No. 7,256,210, which is a division of U.S. application Ser. No. 10/798,317, filed Mar. 12, 2004, now U.S. Pat. No. 7,034,052, which claims the benefit of U.S. Provisional Application No. 60/454,155, filed Mar. 12, 2003, all of which are incorporated herein in their entireties by reference.

1. FIELD OF THE INVENTION

The invention encompasses novel 7-amido-substituted isoindolyl compounds, pharmaceutical compositions of these compounds, and methods of using these compounds and compositions in mammals for the treatment, prevention and management of diseases mediated by PDE4 inhibition, associated with abnormal TNF-α levels and/or mediated by MMP inhibition.

2. BACKGROUND OF THE INVENTION

2.1. TNF-α

Tumor necrosis factor alpha (TNF-α) is a cytokine that is released primarily by inflammation and mononuclear phagocytes in response to immunostimulators. TNF-α is capable of enhancing most cellular processes, such as differentiation, recruitment, proliferation, and proteolytic degradation. At low levels, TNF-α confers protection against infective agents, tumors, and tissue damage. However, TNF-α also has role in many diseases. When administered to mammals such as humans, TNF-α causes or aggravates inflammation, fever, cardiovascular effects, hemorrhage, coagulation, and acute phase responses similar to those seen during acute infections and shock states. Enhanced or unregulated TNF-α production has been implicated in a number of diseases and medical conditions, for example, cancers, such as solid tumors and blood-born tumors; heart disease, such as congestive heart failure; and viral, genetic, inflammatory, allergic, and autoimmune diseases.

Cancer is a particularly devastating disease, and increases in blood TNF-α levels are implicated in the risk of and the spreading of cancer. Normally, in healthy subjects, cancer cells fail to survive in the circulatory system, one of the reasons being that the lining of blood vessels acts as a barrier to tumor-cell extravasation. However, increased levels of cytokines have been shown to substantially increase the adhesion of cancer cells to endothelium in vitro. One explanation is that cytokines, such as TNF-α stimulate the biosynthesis and expression of a cell surface receptors called ELAM-1 (endothelial leukocyte adhesion molecule). ELAM-1 is a member of a family of calcium-dependent cell adhesion receptors, known as LEC-CAMs, which includes LECAM-1 and GMP-140. During an inflammatory response, ELAM-1 on endothelial cells functions as a "homing receptor" for leukocytes. ELAM-1 on endothelial cells was shown to mediate the increased adhesion of colon cancer cells to endothelium treated with cytokines (Rice et al., 1989, Science 246: 1303-1306).

Inflammatory diseases such as arthritis, related arthritic conditions (e.g., osteoarthritis and rheumatoid arthritis), inflammatory bowel disease, sepsis, psoriasis, chronic obstructive pulmonary diseases and chronic inflammatory pulmonary diseases are also prevalent and problematic ailments. TNF-α plays a central role in the inflammatory response and the administration of their antagonists block chronic and acute responses in animal models of inflammatory disease.

Enhanced or unregulated TNF-α production has been implicated in viral, genetic, inflammatory, allergic, and autoimmune diseases. Examples of such diseases include, but are not limited to: HIV; hepatitis; adult respiratory distress syndrome; bone-resorption diseases; chronic obstructive pulmonary diseases; chronic pulmonary inflammatory diseases; dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft versus host disease (GVHD); graft rejection; auto-immune disease; rheumatoid spondylitis; arthritic conditions, such as rheumatoid arthritis, rheumatoid spondylitis and osteoarthritis; osteoporosis; inflammatory-bowel disease; Crohn's disease; ulcerative colitis; multiple sclerosis; systemic lupus erythrematosus; ENL in leprosy; radiation damage; asthma; and hyperoxic alveolar injury. Tracey et al., 1987, Nature 330:662-664 and Hinshaw et al., 1990, Circ. Shock 30:279-292 (endotoxic shock); Dezube et al., 1990, Lancet, 335:662 (cachexia); Millar et al., 1989, Lancet 2:712-714 and Ferrai-Baliviera et al., 1989, Arch. Surg. 124:1400-1405 (adult respiratory distress syndrome); Bertolini et al., 1986, Nature 319:516-518, Johnson et al., 1989, Endocrinology 124:1424-1427, Holler et al., 1990, Blood 75:1011-1016, and Grau et al., 1989, N. Engl. J. Med. 320:1586-1591 (bone resorption diseases); Pignet et al., 1990, Nature, 344:245-247, Bissonnette et al., 1989, Inflammation 13:329-339 and Baughman et al., 1990, J Lab. Clin. Med. 115:36-42 (chronic pulmonary inflammatory diseases); Elliot et al., 1995, Int. J. Pharmac. 17:141-145 (rheumatoid arthritis); von Dullemen et al., 1995, Gastroenterology 109:129-135 (Crohn's disease); Duh et al., 1989, Proc. Nat. Acad. Sci. 86:5974-5978, Poll et al., 1990, Proc. Nat. Acad. Sci. 87:782-785, Monto et al., 1990, Blood 79:2670, Clouse et al., 1989, J. Immunol. 142, 431-438, Poll et al., 1992, AIDS Res. Hum. Retrovirus, 191-197, Poli et al. 1990, Proc. Natl. Acad. Sci. 87:782-784, Folks et al., 1989, Proc. Natl. Acad. Sci. 86:2365-2368 (HIV and opportunistic infections resulting from HIV).

2.2. PDE4

Adenosine 3',5'-cyclic monophosphate (cAMP) also plays a role in many diseases and conditions, such as, but not limited to asthma and inflammation (Lowe and Cheng, Drugs of the Future, 17(9), 799-807, 1992). It has been shown that the elevation of cAMP in inflammatory leukocytes inhibits their activation and the subsequent release of inflammatory mediators, including TNF-α and nuclear factor κB (NF-κB). Increased levels of cAMP also lead to the relaxation of airway smooth muscle.

It is believed that primary cellular mechanism for the inactivation of cAMP is the breakdown of cAMP by a family of isoenzymes referred to as cyclic nucleotide phosphodiesterases (PDE) (Beavo and Reitsnyder, Trends in Pharm., 11, 150-155, 1990). There are twelve known members of the family of PDEs. It is recognized that the inhibition of PDE type IV (PDE4) is particularly effective in both the inhibition of inflammatory mediated release and the relaxation of airway smooth muscle (Verghese, et al., Journal of Pharmacology and Experimental Therapeutics, 272(3), 1313-1320, 1995). Thus, compounds that specifically inhibit PDE4 may inhibit inflammation and aid the relaxation of airway smooth muscle with a minimum of unwanted side effects, such as cardiovascular or anti-platelet effects.

The PDE4 family that is specific for cAMP is currently the largest and is composed of at least 4 isozymes (a-d), and multiple splice variants (Houslay, M. D. et al. in *Advances in Pharmacology* 44, eds. J. August et al., p. 225, 1998). There may be over 20 PDE4 isoforms expressed in a cell specific pattern regulated by a number of different promoters. Disease states for which selective PDE4 inhibitors have been sought include: asthma, atopic dermatitis, depression, reperfusion injury, septic shock, toxic shock, endotoxic shock, adult respiratory distress syndrome, autoimmune diabetes, diabetes insipidus, multi-infarct dementia, AIDS, cancer, Crohn's disease, multiple sclerosis, cerebral ischemia, psoriasis, allograft rejection, restenosis, ulcerative colitis, cachexia, cerebral malaria, allergic rhino-conjunctivitis, osteoarthritis, rheumatoid arthritis, chronic obstructive pulmonary disease (COPD), chronic bronchitis, eosinophilic granuloma, and autoimmune encephalomyelitis (Houslay et al., 1998). PDE4 is present in the brain and major inflammatory cells and has been found in abnormally elevated levels in a number of diseases including atopic dermatitis or eczema, asthma, and hay fever among others (reference OHSU flyer and *J. of Allergy and Clinical Immunology,* 70: 452-457, 1982 by Grewe et al.). In individuals suffering from atopic diseases elevated PDE-4 activity is found in their peripheral blood mononuclear leukocytes, T cells, mast cells, neutrophils and basophils. This increased PDE activity decreases cAMP levels and results in a breakdown of cAMP control in these cells. This results in increased immune responses in the blood and tissues of those that are affected.

Some PDE 4 inhibitors reportedly have a broad spectrum of anti-inflammatory activity, with impressive activity in models of asthma, chronic obstructive pulmonary disorder (COPD) and other allergic disorders such as atopic dermatitis and hay fever. PDE 4 inhibitors that have been used include theophylline, rolipram, denbufylline, ARIFLO, ROFLUMILAST, CDP 840 (a tri-aryl ethane) and CP80633 (a pyrimidone). PDE4 inhibitors have been shown to influence eosinophil responses, decrease basophil histamine release, decrease IgE, PGE2, IL10 synthesis, and decrease anti-CD3 stimulated Il-4 production. Similarly, PDE4 inhibitors have been shown to block neutrophil functions. Neutrophils play a major role in asthma, chronic obstructive pulmonary disorder (COPD) and other allergic disorders. PDE4 inhibitors have been shown to inhibit the release of adhesion molecules, reactive oxygen species, interleukin (IL)-8 and neutrophil elastase, associated with neutrophils which disrupt the architecture of the lung and therefore airway function. PDE4 inhibitors influence multiple functional pathways, act on multiple immune and inflammatory pathways, and influence synthesis or release of numerous immune mediators. J. M. Hanifin and S. C. Chan, "Atopic Dermatitis-Therapeutic Implication for New Phosphodiesterase Inhibitors," Monocyte Dysregulation of T Cells in AACI News, 7/2, 1995; J. M. Hanifin et al., "Type 4 Phosphodiesterase Inhibitors Have clinical and In Vitro Anti-inflammatory Effects in Atopic Dermatitis," *Journal of Investigative Dermatology,* 1996, 107, pp 51-56).

Some of the first generation of PDE-4 inhibitors are effective in inhibiting PDE4 activity and alleviating a number of the inflammatory problems caused by over expression of this enzyme. However, their effectiveness is limited by side effects, particularly when used systemically, such as nausea and vomiting. Huang et al., *Curr. Opin. In Chem. Biol.* 2001, 5:432-438. Indeed, all of the PDE-4 inhibitors developed to date have been small molecule compounds with central nervous system and gastrointestinal side effects, e.g., headache, nausea/emesis, and gastric secretion.

2.3. MMP

Matrix metalloproteinases (MMPs) are a family of proteases (enzymes) involved in the degradation and remodeling of connective tissues. Excessive degradation of extracellular matrix by MMPs is implicated in the pathogenesis of many diseases, including rheumatoid arthritis, osteoarthritis, cancer, multiple sclerosis, bone resorptive diseases (such as osteoporosis), chronic obstructive pulmonary disease, restenosis, cerebral hemorrhaging associated with stroke, periodontal disease, aberrant angiogenesis, tumor invasion and metastasis, corneal and gastric ulceration, ulceration of skin, aneurysmal disease, and in complications of diabetes. MMP inhibition is, therefore, recognized as a good target for therapeutic intervention of this type of diseases. Many compounds having MMP inhibition activities have been reported (R. A. Nigel et al, *Current Opinion on Therapeutic Patents*, Vol. 4, 7-16, (1994), R. P. Beckett et al, *Drug Discovery Today, Vol.* 1, 16-26, (1996)). However, most are peptide derivatives based on the amino acid sequence of the enzymatic cleavage site in the collagen molecule constituting the substrate of MMP. A need exists for small molecule inhibitors of MMP.

3. SUMMARY OF THE INVENTION

The present invention provides compounds which are useful in the treatment of diseases mediated by the inhibition of PDE4, TNF-α and/or MMP, and other various diseases or disorders. The invention also provides pharmaceutical compositions comprising these compounds and methods of using the subject compounds and compositions for the treatment of a variety of diseases.

One embodiment of the invention encompasses compounds of formula (I):

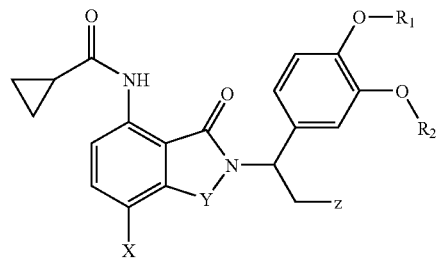

wherein:

Y is —C(O)—, —CH$_2$—, —CH$_2$C(O)— or —SO$_2$—;

X is H;

Z is (C$_{0-4}$-alkyl)-C(O)R$^3$, C$_{1-4}$-alkyl, (C$_{0-4}$-alkyl)-OH, (C$_{1-4}$-alkyl)-O—(C$_{1-4}$-alkyl), (C$_{1-4}$-alkyl)-SO$_2$(C$_{1-4}$-alkyl), (C$_{0-4}$-alkyl)-SO(C$_{1-4}$-alkyl), (C$_{0-4}$-alkyl)-NH$_2$, (C$_{0-4}$-alkyl)-N(C$_{1-8}$-alkyl)$_2$, (C$_{0-4}$-alkyl)-N(H)(OH), (C$_{0-4}$-alkyl)-dichloropyridine, or CH$_2$NSO$_2$—(C$_{1-4}$-alkyl);

R$_1$ and R$_2$ are independently C$_{1-8}$-alkyl, cycloalkyl, or (C$_{1-4}$-alkyl)-cycloalkyl;

R$^3$ is, NR$^4$, R$^5$, OH, or O—(C$_{1-8}$-alkyl);

R$^4$ is H;

R$^5$ is —OH, or —O—C(O)R$^6$;

$R^6$ is $C_{1-8}$-alkyl, amino-($C_{1-8}$-alkyl), ($C_{1-8}$-alkyl)-($C_{3-6}$-cycloalkyl), $C_{3-6}$-cycloalkyl, phenyl, benzyl, or aryl;

and pharmaceutically acceptable salts, solvates, hydrates, stereoisomers, clathrates, or prodrugs thereof.

In one embodiment, Z is ($C_{0-4}$-alkyl)-C(O)$R^3$, $C_{1-4}$-alkyl, ($C_{0-4}$-alkyl)-OH, ($C_{1-4}$-alkyl)-O—($C_{1-4}$-alkyl), ($C_{1-4}$-alkyl)-SO$_2$($C_{1-4}$-alkyl), ($C_{0-4}$-alkyl)-SO($C_{1-4}$-alkyl), ($C_{0-4}$-alkyl)-NH$_2$, ($C_{0-4}$-alkyl)-N($C_{1-8}$-alkyl)$_2$, ($C_{0-4}$-alkyl)-N(H)(OH), or CH$_2$NSO$_2$—($C_{1-4}$-alkyl).

This invention also encompasses compounds of formula (II):

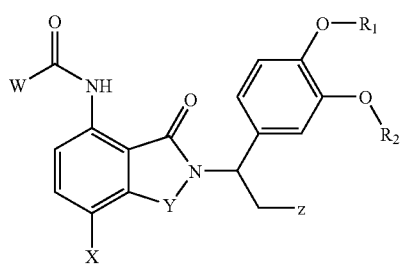

wherein:

Y is —C(O)—, —CH$_2$—, —CH$_2$C(O)—, or —SO$_2$—;

X is halogen, CN, NR$_7$R$_8$, NO$_2$, CH$_3$, or CF$_3$;

Z is ($C_{0-4}$-alkyl)-SO$_2$($C_{1-4}$-alkyl), ($C_{0-4}$-alkyl)-CN, ($C_{0-4}$-alkyl)-C(O)R$^3$, $C_{1-4}$-alkyl, ($C_{0-4}$-alkyl)-OH, ($C_{0-4}$-alkyl)-O—($C_{1-4}$-alkyl), ($C_{0-4}$-alkyl)-SO($C_{1-4}$-alkyl), ($C_{0-4}$-alkyl)-NH$_2$, ($C_{0-4}$-alkyl)-N($C_{1-8}$-alkyl)$_2$, ($C_{0-4}$-alkyl)-N(H)(OH), ($C_{0-4}$-alkyl)-dichloropyridine, or ($C_{0-4}$-alkyl)-NSO$_2$($C_{1-4}$-alkyl);

W is $C_{3-6}$-cycloalkyl, ($C_{1-8}$-alkyl)-($C_{3-6}$-cycloalkyl), ($C_{0-8}$-alkyl)-($C_{3-6}$cycloalkyl)-NR$_7$R$_8$, ($C_{0-8}$-alkyl)-NR$_7$R$_8$, ($C_{0-4}$alkyl)-CHR$_9$—($C_{0-4}$alkyl)-NR$_7$R$_8$, R$_1$ and R$_2$ are independently $C_{1-8}$-alkyl, cycloalkyl, or ($C_{1-4}$-alkyl)-cycloalkyl;

R$^3$ is $C_{1-8}$-alkyl, NR$^4$, R$^5$, OH, or O—($C_{1-8}$-alkyl);

R$^4$ and R$^5$ are independently H, $C_{1-8}$-alkyl, ($C_{0-8}$-alkyl)-($C_{3-6}$-cycloalkyl), OH, or OC(O)R$^6$;

R$^6$ is $C_{1-8}$-alkyl, ($C_{0-8}$-alkyl)-($C_{3-6}$-cycloalkyl), amino-($C_{1-8}$-alkyl), phenyl, benzyl, or aryl;

R$_7$ and R$_8$ are each independently H, $C_{1-8}$-alkyl, ($C_{0-8}$-alkyl)-($C_{3-6}$-cycloalkyl), phenyl, benzyl, aryl, or can be taken together with the atom connecting them to form a 3 to 7 membered heterocycloalkyl or heteroaryl ring;

R$^9$ is $C_{1-4}$ alkyl, ($C_{0-4}$-alkyl)-aryl, ($C_{0-4}$-alkyl)-($C_{3-6}$-cycloalkyl), ($C_{0-4}$alkyl)-heterocycle;

and pharmaceutically acceptable salts, solvates, hydrates, stereoisomers, clathrates, or prodrugs thereof.

In another embodiment, Z is ($C_{0-4}$-alkyl)-SO$_2$($C_{1-4}$-alkyl), ($C_{0-4}$-alkyl)-CN, ($C_{0-4}$-alkyl)-C(O)R$^3$, $C_{1-4}$-alkyl, ($C_{0-4}$-alkyl)-OH, ($C_{0-4}$-alkyl)-O—($C_{1-4}$-alkyl), ($C_{0-4}$-alkyl)-SO($C_{1-4}$-alkyl), ($C_{0-4}$-alkyl)-NH$_2$, ($C_{0-4}$-alkyl)-N($C_{1-8}$-alkyl)$_2$, ($C_{0-4}$-alkyl)-N(H)(OH), or ($C_{0-4}$-alkyl)-NSO$_2$(C1-4-alkyl).

In another embodiment, W is:

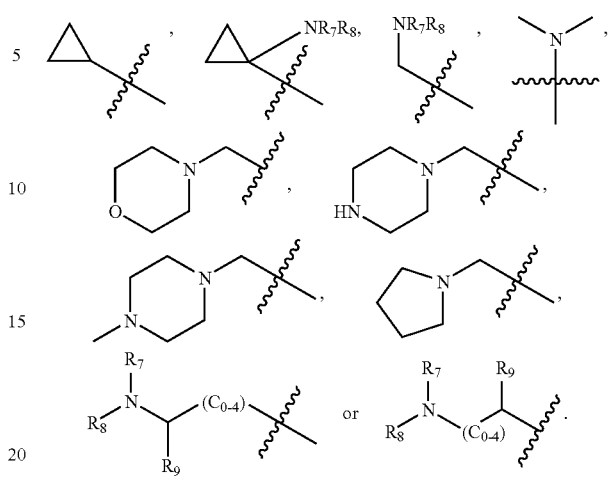

In another embodiment, W is not

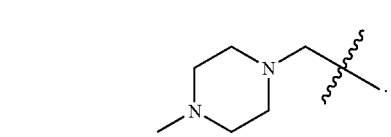

In another embodiment, this invention encompasses compounds of formula (III):

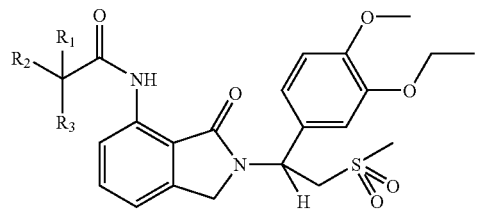

wherein:

R$_1$, R$_2$ and R$_3$ are independently H or $C_{1-8}$-alkyl, with the proviso that at least one of R$_1$, R$_2$ and R$_3$ is not H;

and pharmaceutically acceptable salts, solvates, hydrates, stereoisomers, clathrates, or prodrugs thereof.

In one embodiment, with regard to formula III, R$_1$ is H and R$_2$ and R$_3$ are both methyl.

In another embodiment, with regard to formula III, R$_1$, R$_2$ and R$_3$ are methyl.

In another embodiment, the invention encompasses a method of modulating (e.g., inhibiting) the production or lowering the levels of PDE4 in a mammal or a mammalian cell comprising administering to said mammal an effective amount of a compound of the invention (e.g., compounds of formula I, II or III).

Another embodiment of the invention encompasses a method of modulating the production of, or lowering the levels of, TNF-α in a mammal or a mammalian cell comprising administering to said mammal or mammalian cell an effective amount of a compound of the invention.

In yet another embodiment, the invention encompasses a method of modulating the production of, or inhibiting or lowering the levels of, MMP in a mammal or a mammalian cell comprising administering to said mammal or mammalian cell an effective amount of a compound of the invention.

Other embodiments of the invention encompass methods of treating, preventing and managing various disease or disorders, such as, but not limited to: central nervous system (CNS) disorders; myelodysplastic syndrome (MDS) and related syndromes; complex regional pain syndrome (CRPS) and related syndromes; cancer and related diseases; macular degeneration (MD) and related syndromes; myeloproliferative diseases (MPD) and related syndromes; and asbestos-related diseases and disorders.

Pharmaceutical compositions, modes of administration, formulations, and methods of using the above compounds alone or in combination are described in more detail below.

3.1. Abbreviations and Definitions

The abbreviations used herein are conventional, unless otherwise defined.

The terms "treat," "treating" and "treatment," as used herein, contemplate an action that occurs while a patient is suffering from the specified disease or disorder, which reduces the severity of the disease or disorder.

As used herein, and unless otherwise specified, the terms "prevent," "preventing" and "prevention" contemplate an action that occurs before a patient begins to suffer from the specified disease or disorder, which inhibits or reduces the severity of the disease or disorder.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The term "therapeutically effective amount" refers to that amount of the compound being administered sufficient to prevent development of or alleviate to some extent one or more of the symptoms of the condition or disorder being treated as well as to alleviate or eradicate the cause of the disease itself.

As used herein, the term "PDE4-responsive condition or disorder" or "mediated by PDE4 inhibition" or "mediated by inhibition of PDE4" refers to a condition or disorder that responds favorably to modulation of PDE4 activity. Favorable responses to PDE4 modulation include alleviation or abrogation of the disease and/or its attendant symptoms, inhibition of the disease, i.e., arrest or reduction of the development of the disease, or its clinical symptoms, and regression of the disease or its clinical symptoms. A PDE4-responsive condition or disease may be completely or partially responsive to PDE4 modulation. A PDE4-responsive condition or disorder may be associated with inappropriate, e.g., less than or greater than normal, PDE4-activity. Inappropriate PDE4 functional activity might arise as the result of PDE4 expression in cells which normally do not express PDE4, decreased PDE4 expression (leading to, e.g., lipid and metabolic disorders and diseases) or increased PDE4 expression. A PDE4-responsive condition or disease includes a PDE4-mediated condition or disease.

The term "alkyl," by itself or as part of another substituent, means, unless otherwise stated, a straight or branched chain, acyclic or cyclic hydrocarbon radical, or combination thereof, which may be fully saturated, mono- or polyunsaturated and can include di- and multi-valent radicals, having the number of carbon atoms designated (e.g., $C_{0-10}$ means one to ten carbons, or not present, i.e., $C_0$ means the moiety does not exist). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene." The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, acyclic or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$—CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini. For alkylene and heteroalkylene linking groups, no orientation of the linking group is implied.

The terms "cycloalkyl" and "heterocycloalkyl," by themselves or in combination with other terms, represent, unless otherwise stated, cyclic versions of "alkyl" and "heteroalkyl," respectively. Thus, the terms "cycloalkyl" and "heterocycloalkyl" are meant to be included in the terms "alkyl" and "heteroalkyl," respectively. Furthermore, the term "$C_{3-18}$ cycloalkyl," means a cycloalkyl with 3 to 18 carbon atoms. Additionally, for heterocycloalkyl, a heteroatom can occupy the position at which the heterocycle is attached to the remainder of the molecule. Examples of cycloalkyl include cyclopropyl, cyclobutyl, cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include alkyl substituted with halogen atoms which can be the same or different, in a number ranging from one to (2m'+1), where m' is the total number of carbon atoms in the alkyl group. For example, the term "halo $(C_1-C_4)$alkyl" includes trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example, the term "perhalo$(C_1-C_4)$alkyl" includes trifluoromethyl, pentachloroethyl, 1,1,1-trifluoro-2-bromo-2-chloroethyl, and the like.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a heteroatom. Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, oxadiazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, triazolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below.

The term "arylalkyl" includes those radicals in which an aryl group is attached to an alkyl group (e.g., benzyl, phenethyl, pyridylmethyl and the like) or a heteroalkyl group (e.g. phenoxymethyl, 2-pyridyloxymethyl, 3-(1-naphthyloxy)propyl, and the like).

Each of the above terms (e.g., "alkyl," "heteroalkyl" and "aryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2N+1), where N is the total number of carbon atoms in such radical, and where R', R" and R'" each independently refer to hydrogen, unsubstituted$(C_1-C_8)$alkyl and heteroalkyl, unsubstituted aryl, aryl substituted with 1-3 halogens, unsubstituted alkyl, alkoxy or thioalkoxy groups, or aryl-$(C_1-C_4)$alkyl groups. When R' and R" are attached to the same nitrogen atom, they can be combined with the carbon atoms to which they are attached with the nitrogen atom to form a 5-, 6- or 7-membered ring containing from 1 to 3 heteroatoms selected from the group consisting of N, O and S. For example, —NR'R" includes 1-pyrrolidinyl and 4-morpholinyl. From the above discussion of substituents, one of skill in the art will understand that the term "alkyl" includes substituted alkyl groups including haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similarly, substituents for the aryl groups are varied and can be selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, fluoro$(C_1-C_4)$alkoxy, and fluoro$(C_1-C_4)$alkyl, in a number ranging from zero to the total number of open valences on the aromatic ring system; and where each R', R" and R'" is independently selected from hydrogen, $(C_1-C_8)$alkyl and heteroalkyl, unsubstituted aryl, (unsubstituted aryl)-$(C_1-C_4)$alkyl and (unsubstituted aryl)oxy-$(C_1-C_4)$alkyl.

As used herein, the term "heteroatom" includes oxygen (O), nitrogen (N) and sulfur (S). In certain embodiments, the term further encompasses silicon (Si).

The term "pharmaceutically acceptable salt" includes salts which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, and magnesium salts. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids such as hydrochloric, hydrobromic, nitric, carbonic, monohydrogencarbonic, phosphoric, monohydrogenphosphoric, dihydrogenphosphoric, sulfuric, monohydrogensulfuric, hydriodic, and phosphorous acids, as well as the salts derived from relatively nontoxic organic acids such as acetic, propionic, isobutyric, oxalic, maleic, malonic, benzoic, succinic, suberic, fumaric, mandelic, phthalic, benzenesulfonic, p-tolylsulfonic, citric, tartaric, and methanesulfonic acids. Also included are salts of amino acids, such as arginate, and salts of organic acids, such as glucuronic and galactunoric acids. See, e.g., Berge et al. (1977) *J. Pharm. Sci.* 66:1-19. Certain specific compounds of the present invention contain both basic and acidic functionalities that allow the compounds to be converted into either base or acid addition salts.

Neutral forms of some compounds may be regenerated by contacting the salt with a base or acid and isolating the parent compound in the conventional manner. The parent form of a compound can differ from its various salt forms in certain physical properties, such as solubility in polar solvents, but the salts are typically equivalent to the parent form of the compound for the purposes of the present invention.

Certain compounds of the present invention can exist in unsolvated forms as well as solvated forms, including hydrated forms. In general, solvated forms are equivalent to unsolvated forms. Certain compounds of the invention may exist in multiple crystalline or amorphous forms. In general, all physical forms are equivalent for the uses contemplated by the present invention, and are encompassed by the present invention.

Certain compounds of the present invention possess asymmetric carbon atoms (optical or stereo-centers) or double bonds; the racemates, enantiomers, diastereomers, geometric isomers and mixtures thereof are all intended to be encompassed by this invention.

Compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). Radiolabeled compounds are useful as therapeutic agents, e.g., cancer therapeutic agents, research reagents, e.g., assay reagents, and diagnostic agents, e.g., in vivo imaging agents. All isotopic variations of the compounds of the present invention, whether radioactive or not, are intended to be encompassed within the scope of the present invention.

4. DETAILED DESCRIPTION OF THE INVENTION

The invention encompasses novel compounds and compositions that can be used to treat, prevent or manage diseases and disorders in mammals (e.g., humans). Examples of such diseases or disorders include, but are not limited to: cancer; viral, genetic, inflammatory, allergic, and autoimmune diseases; bacterial infections; CNS disorders; MDS and related syndromes; CRPS and related syndromes; MD and related syndromes; MPD and related syndromes; and asbestos-related diseases or disorders. Compounds of the invention can be used to treat, prevent or manage diseases caused or aggravated by excessive, insufficient or unregulated levels of PDE4, TNF-α, and/or MMP.

One embodiment of the invention encompasses compounds of formula (I):

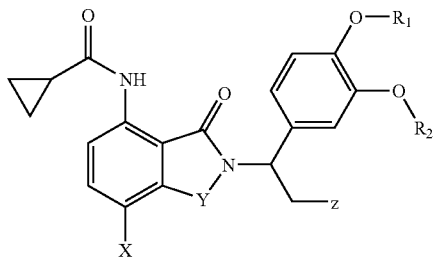

wherein:

Y is —C(O)—, —CH$_2$—, —CH$_2$C(O)— or —SO$_2$—;

X is H;

Z is (C$_{0-4}$-alkyl)-C(O)R$^3$, C$_{1-4}$-alkyl, (C$_{0-4}$-alkyl)-OH, (C$_{1-4}$-alkyl)-O—(C$_{1-4}$-alkyl), (C$_{1-4}$-alkyl)-SO$_2$(C$_{1-4}$-alkyl), (C$_{0-4}$-alkyl)-SO(C$_{1-4}$-alkyl), (C$_{0-4}$-alkyl)-NH$_2$, (C$_{0-4}$-alkyl)-N(C$_{1-8}$-alkyl)$_2$, (C$_{0-4}$-alkyl)-N(H)(OH), (C$_{0-4}$-alkyl)-dichloropyridine, or CH$_2$NSO$_2$—(C$_{1-4}$-alkyl);

R$_1$ and R$_2$ are independently C$_{1-8}$-alkyl, cycloalkyl, or (C$_{1-4}$-alkyl)-cycloalkyl;

R$^3$ is, NR$^4$R$^5$, OH, or O—(C$_{1-8}$-alkyl);

R$^4$ is H;

R$^5$ is —OH, or —O—C(O)R$^6$;

R$^6$ is C$_{1-8}$-alkyl, amino-(C$_{1-8}$-alkyl), (C$_{1-8}$-alkyl)-(C$_{3-6}$-cycloalkyl), C$_{3-6}$-cycloalkyl, phenyl, benzyl, or aryl;

and pharmaceutically acceptable salts, solvates, hydrates, stereoisomers, clathrates, or prodrugs thereof.

In one embodiment, Z is (C$_{0-4}$-alkyl)-C(O)R$^3$, C$_{1-4}$-alkyl, (C$_{0-4}$-alkyl)-OH, (C$_{1-4}$-alkyl)-O—(C$_{1-4}$-alkyl), (C$_{1-4}$-alkyl)-SO$_2$(C$_{1-4}$-alkyl), (C$_{0-4}$-alkyl)-SO(C$_{1-4}$-alkyl), (C$_{0-4}$-alkyl)-NH$_2$, (C$_{0-4}$-alkyl)-N(C$_{1-8}$-alkyl)$_2$, (C$_{0-4}$-alkyl)-N(H)(OH), or CH$_2$NSO$_2$—(C$_{1-4}$-alkyl).

This invention also encompasses compounds of formula (II):

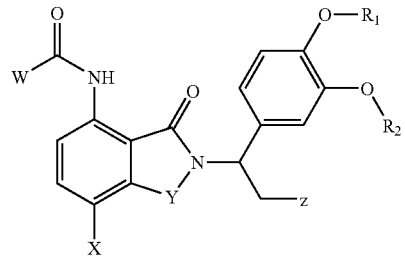

wherein:

Y is —C(O)—, —CH$_2$—, —CH$_2$C(O)—, or —SO$_2$—;

X is halogen, CN, NR$_7$R$_8$, NO$_2$, CH$_3$, or CF$_3$;

Z is (C$_{0-4}$-alkyl)-SO$_2$(C$_{1-4}$-alkyl), (C$_{0-4}$-alkyl)-CN, (C$_{0-4}$-alkyl)-C(O)R$^3$, C$_{1-4}$-alkyl, (C$_{0-4}$-alkyl)-OH, (C$_{0-4}$-alkyl)-O—(C$_{1-4}$-alkyl), (C$_{0-4}$-alkyl)-SO(C$_{1-4}$-alkyl), (C$_{0-4}$-alkyl)-NH$_2$, (C$_{0-4}$-alkyl)-N(C$_{1-8}$-alkyl)$_2$, (C$_{0-4}$-alkyl)-N(H)(OH), (C$_{0-4}$-alkyl)-dichloropyridine, or (C$_{0-4}$-alkyl)-NSO$_2$(C1-4-alkyl);

W is C$_{3-6}$-cycloalkyl, (C$_{1-8}$-alkyl)-(C$_{3-6}$-cycloalkyl), (C$_{0-8}$-alkyl)-(C$_{3-6}$cycloalkyl)-NR$_7$R$_8$, (C$_{0-8}$-alkyl)-NR$_7$R$_8$, (C$_{0-4}$alkyl)-CHR$_9$—(C$_{0-4}$alkyl)-NR$_7$R$_8$, R$_1$ and R$_2$ are independently C$_{1-8}$-alkyl, cycloalkyl, or (C$_{1-4}$-alkyl)-cycloalkyl;

R$^3$ is C$_{1-8}$-alkyl, NR$^4$, R$^5$, OH, or O—(C$_{1-8}$-alkyl);

R$^4$ and R$^5$ are independently H, C$_{1-8}$-alkyl, (C$_{0-8}$-alkyl)-(C$_{3-6}$-cycloalkyl), OH, or OC(O)R$^6$;

R$^6$ is C$_{1-8}$-alkyl, (C$_{0-8}$-alkyl)-(C$_{3-6}$-cycloalkyl), amino-(C$_{1-8}$-alkyl), phenyl, benzyl, or aryl;

R$_7$ and R$_8$ are each independently H, C$_{1-8}$-alkyl, (C$_{0-8}$-alkyl)-(C$_{3-6}$-cycloalkyl), phenyl, benzyl, aryl, or can be taken together with the atom connecting them to form a 3 to 7 membered heterocycloalkyl or heteroaryl ring;

R$_9$ is C$_{1-4}$ alkyl, (C$_{0-4}$-alkyl)-aryl, (C$_{0-4}$-alkyl)-(C$_{3-6}$-cycloalkyl), (C$_{0-4}$alkyl)-heterocycle;

and pharmaceutically acceptable salts, solvates, hydrates, stereoisomers, clathrates, or prodrugs thereof.

In another embodiment, Z is (C$_{0-4}$-alkyl)-SO$_2$(C$_{1-4}$-alkyl), (C$_{0-4}$-alkyl)-CN, (C$_{0-4}$-alkyl)-C(O)R$^3$, C$_{1-4}$-alkyl, (C$_{0-4}$- alkyl)-OH, $(C_{0-4}$-alkyl)-O—$(C_{1-4}$-alkyl), $(C_{0-4}$-alkyl)-SO $(C_{1-4}$-alkyl), $(C_{0-4}$-alkyl)-NH$_2$, $(C_{0-4}$-alkyl)-N$(C_{1-8}$-alkyl)$_2$, $(C_{0-4}$-alkyl)-N(H)(OH), or $(C_{0-4}$-alkyl)-NSO$_2$(C1-4-alkyl).

In another embodiment, W is:

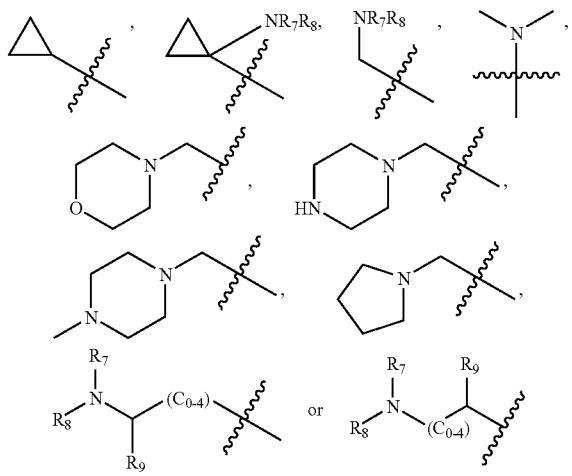

In another embodiment, W is not

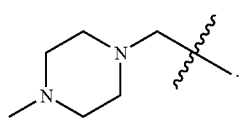

In another embodiment, this invention encompasses compounds of formula (III):

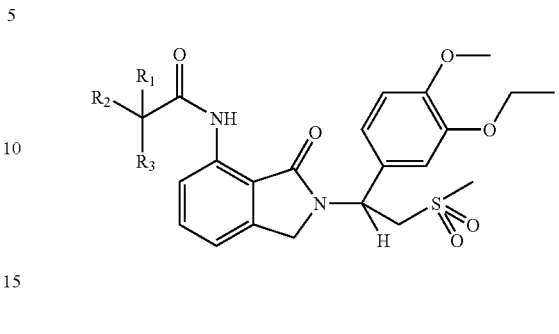

wherein:

$R_1$, $R_2$ and $R_3$ are independently H or $C_{1-8}$-alkyl, with the proviso that at least one of $R_1$, $R_2$ and $R_3$ is not H;

and pharmaceutically acceptable salts, solvates, hydrates, stereoisomers, clathrates, or prodrugs thereof.

In one embodiment, with regard to formula III, $R_1$ is H and $R_2$ and $R_3$ are both methyl.

In another embodiment, with regard to formula III, $R_1$, $R_2$ and $R_3$ are methyl.

Examples of compounds of the invention include, but are not limited to, those listed in Table I below:

TABLE I

| No. | Compound | Name |
|---|---|---|
| 1 | | (1R)-Cyclopropanecarboxylic acid {2-[1-(3-ethoxy-4-methoxyphenyl)-3-hydroxy-propyl]-3-oxo-2,3-dihydro-1H-isoindol-4-yl}-amide |
| 2 | | (3R)-(tert-Butoxy)-N-{3-[7-(cyclopropylcarbonylamino)-1-oxoisoindolin-2-yL]-3-(3-ethoxy-4-methoxyphenyl)propyl}carbonyl amino (tert-butoxy)formate |

TABLE I-continued

| No. | Compound | Name |
|---|---|---|
| 3 | | (1R)-Cyclopropanecarboxylic acid {2-[1-(3-ethoxy-4-methoxy-phenyl)-3-hydroxyamino-propyl]-3-oxo-2,3-dihydro-1H-isoindol-4-yl}-amide |
| 4 | | (1R)-Cyclopropanecarboxylic acid {2-[1-(3-ethoxy-4-methoxy-phenyl)-3-methanesulfonylamino-propyl]-3-oxo-2,3-dihydro-1H-isoindol-4-yl}-amide |
| 5 | | (1R)-Cyclopropanecarboxylic acid {2-[3-amino-1-(3-ethoxy-4-methoxy-phenyl)-propyl]-3-oxo-2,3-dihydro-1H-isoindol-4-yl}-amide |
| 6 | | (1R)-Cyclopropanecarboxylic acid {2-[1-(3-ethoxy-4-methoxy-phenyl)-3-ureido-propyl]-3-oxo-2,3-dihydro-1H-isoindol-4-yl}-amide |
| 7 | | (1R)-Cyclopropanecarboxylic acid {2-[3-dimethylamino-1-(3-ethoxy-4-methoxy-phenyl)-propyl]-3-oxo-2,3-dihydro-1H-isoindol-4-yl}-amide hydrochloride |
| 8 | | (1R)-Cyclopropanecarboxylic acid {2-[1-(3-ethoxy-4-methoxy-phenyl)-3-methanesulfonyl-propyl]-3-oxo-2,3-dihydro-1H-isoindol-4-yl}-amide |

TABLE I-continued

| No. | Compound | Name |
|---|---|---|
| 9 | | (1R)-Cyclopropanecarboxylic acid {2-[1-(3-ethoxy-4-methoxy-phenyl)-2-hydroxycarbamoyl-ethyl]-3-oxo-2,3-dihydro-1H-isoindol-4-yl}-amide |
| 10 | | (1R)-Cyclopropanecarboxylic acid {2-[2-acetoxycarbamoyl-1-(3-ethoxy-4-methoxy-phenyl)-ethyl]-3-oxo-2,3-dihydro-1H-isoindol-4-yl}-amide |
| 11 | | (3R)-Cyclopropanecarboxylic acid {2-[1-(3-ethoxy-4-methoxy-phenyl)-3-methanesulfinyl-propyl]-3-oxo-2,3-dihydro-1H-isoindol-4-yl}-amide |
| 12 | | (3R)-3-[4-Chloro-7-(cyclopropanecarbonyl-amino)-1-oxo-1,3-dihydro-isoindol-2-yl]-3-(3-ethoxy-4-methoxy-phenyl)-propionic acid |
| 13 | | (3R)-3-[4-Chloro-7-(cyclopropanecarbonyl-amino)-1-oxo-1,3-dihydro-isoindol-2-yl]-3-(3-ethoxy-4-methoxy-phenyl)-propionic acid methyl ester |

TABLE I-continued

| No. | Compound | Name |
|---|---|---|
| 14 | | (1R)-Cyclopropanecarboxylic acid {2-[2-carbamoyl-1-(3-ethoxy-4-methoxy-phenyl)-ethyl]-7-chloro-3-oxo-2,3-dihydro-1H-isoindol-4-yl}-amide |
| 15 | | (1R)-Cyclopropanecarboxylic acid {7-chloro-2-[2-dimethylcarbamoyl-1-(3-ethoxy-4-methoxy-phenyl)-ethyl]-3-oxo-2,3-dihydro-1H-isoindol-4-yl}-amide |
| 16 | | (1R)-Cyclopropanecarboxylic acid {7-chloro-2-[1-(3-ethoxy-4-methoxy-phenyl)-2-hydroxycarbamoyl-ethyl]-3-oxo-2,3-dihydro-IH-isoindol-4-yl}-amide |
| 17 | | (1R)-Cyclopropanecarboxylic acid {2-[2-acetoxycarbamoyl-1-(3-ethoxy-4-methoxy-phenyl)-ethyl]-7-chloro-3-oxo-2,3-dihydro-1H-isoindol-4-yl}-amide |
| 18 | | (1S)-Cyclopropanecarboxylic acid {7-chloro-2-[1-(3-ethoxy-4-methoxy-phenyl)-2-methanesulfonyl-ethyl]-3-oxo-2,3-dihydro-1H-isoindol-4-yl}-amide |

TABLE I-continued

| No. | Compound | Name |
|---|---|---|
| 19 | | (1S)-Cyclopropanecarboxylic acid {7-bromo-2-[1-(3-ethoxy-4-methoxy-phenyl)-2-methanesulfonyl-ethyl]-3-oxo-2,3-dihydro-1H-isoindol-4-yl}-amide |
| 20 | | Cyclopropanecarboxylic acid {2-[1-(3-ethoxy-4-methoxy-phenyl)-propyl]-3-oxo-2,3-dihydro-1H-isoindol-4-yl}-amide |
| 21 | | Cyclopropanecarboxylic acid {7-chloro-2-[2-cyano-1-(3-ethoxy-4-methoxy-phenyl)-ethyl]-3-oxo-2,3-dihydro-1H-isoindol-4-yl}-amide |
| 22 | | Cyclopropanecarboxylic acid {2-[2-(3,5-dichloro-pyridin-4-yl)-1-(3-ethoxy-4-methoxy-phenyl)-ethyl]-3-oxo-2,3-dihydro-1H-isoindol-4-yl}-amide |
| 23 | | (1R)-Cyclopropanecarboxylic acid {2-[1-(3-ethoxy-4-methoxy-phenyl)-3-hydroxy-3-methyl-butyl]-3-oxo-2,3-dihydro-1H-isoindol-4-yl}-amide |

TABLE I-continued

| No. | Compound | Name |
|---|---|---|
| 24 | | (1R)-Cyclopropanecarboxylic acid{2-[2-cyclopropanecarbonyloxycarbamoyl-1-(3-ethoxy-4-methoxy-phenyl)-ethyl]-3-oxo-2,3-dihydro-1H-isoindol-4-yl}-amide |
| 25 | | (1R)-Cyclopropanecarboxylic acid {2-[1-(3-ethoxy-4-methoxy-phenyl)-2-isobutyryloxycarbamoyl-ethyl]-3-oxo-2,3-dihydro-1H-isoindol-4-yl}-amide |
| 26 | | (1R)-Cyclopropanecarboxylic acid {2-[2-(2,2-dimethyl-propionyloxycarbamoyl)-1-(3-ethoxy-4-methoxy-phenyl)-ethyl]-3-oxo-2,3-dihydro-1H-isoindol-4-yl}-amide |
| 27 | | (1R)-Cyclopropanecarboxylic acid {2-[2-(3,3-dimethyl-butyryloxycarbamoyl)-1-(3-ethoxy-4-methoxy-phenyl)-ethyl]-3-oxo-2,3-dihydro-1H-isoindol-4-yl}-amide |
| 28 | | (1S)-Cyclopropanecarboxylic acid {2-[1-(3-ethoxy-4-methoxy-phenyl)-2-methanesulfonyl-ethyl]-7-fluoro-3-oxo-2,3-dihydro-1H-isoindol-4-yl}-amide |

TABLE I-continued

| No. | Compound | Name |
|---|---|---|
| 29 | | (1S)-3-{7-Chloro-2-[1-(3-ethoxy-4-methoxy-phenyl)-2-methanesulfonyl-ethyl]-3-oxo-2,3-dihydro-1H-isoindol-4-yl}-1,1-dimethyl-urea |
| 30 | | (1S)-N-{7-Chloro-2-[1-(3-ethoxy-4-methoxy-phenyl)-2-methanesulfonyl-ethyl]-3-oxo-2,3-dihydro-1H-isoindol-4-yl}-2-(4-methyl-piperazin-1-yl)-acetamide |
| 31 | | (1S)-N-{7-Chloro-2-[1-(3-ethoxy-4-methoxy-phenyl)-2-methanesulfonyl-ethyl]-3-oxo-2,3-dihydro-1H-isoindol-4-yl}-2-morpholin-4-yl-acetamide; hydrochloride |
| 32 | | (1S)-N-{7-Chloro-2-[1-(3-ethoxy-4-methoxy-phenyl)-2-methanesulfonyl-ethyl]-3-oxo-2,3-dihydro-1H-isoindol-4-yl}-2-dimethylamino-acetamide; hydrochloride |
| 33 | | N-{2-[1-(3-Ethoxy-4-methoxy-phenyl)-2-methanesulfonyl-ethyl]-3-oxo-2,3-dihydro-1H-isoindol-4-yl}-2,2-dimethyl-propionamide |

TABLE I-continued

| No. | Compound | Name |
| --- | --- | --- |
| 34 |  | N-{2-[1-(3-Ethoxy-4-methoxy-phenyl)-2-methanesulfonyl-ethyl]-3-oxo-2,3-dihydro-1H-isoindol-4-yl}-isobutyramide |

Compounds of the invention generally exist in solid form and can be recrystallized according to well-known methods affording high-purity crystals, preferably, in greater than 95% purity, more preferably, in greater than 98% purity. A narrow melting-point range is often an indication of purity. Thus, preferred compounds of the invention have a melting point within a range of 3° C. to 4° C., more preferably, within a range of 2° C.

Various compounds of the invention contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular compounds of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

Compounds of the invention can contain one or more chiral centers and/or double bonds and, therefore, exist as stereoisomers and geometric isomers. Chemical structures and portions of chemical structures depicted herein that do not indicate stereochemistry encompass all of their enantiomers and stereoisomers, e.g., both the stereomerically pure forms stereoisomeric mixtures.

As used herein, and unless otherwise indicated, the term "stereoisomeric mixture" encompasses racemic mixtures as well as enantiomerically enriched mixtures (e.g., R/S=30/70, 35/65, 40/60, 45/55, 55/45, 60/40, 65/35 and 70/30).

As used herein, and unless otherwise indicated, the term "stereomerically pure" or "enantiomerically pure" means that a compound one stereoisomer and is substantially free of its counter stereoisomer or enantiomer. For example, a compound is stereomerically or eneantiomerically pure when the compound contains 80%, 90%, or 95% or more of one stereoisomer and 20%, 10%, or 5% or less of the counter stereoisomer. In certain cases, a compound of the invention is considered optically active or stereomerically/enantiomerically pure (i.e., substantially the R-form or substantially the S-form) with respect to a chiral center when the compound is about 80% ee (enantiomeric excess) or greater, preferably, equal to or greater than 90% ee with respect to a particular chiral center, and more preferably 95% ee with respect to a particular chiral center. Thus, the invention encompasses all enantiomerically pure, enantiomerically enriched, and racemic mixtures of compounds of Formula I, II, or III.

In one embodiment, the invention encompasses an enantiomerically R isomer of a compound of formula I, II or III, substantially free of its S isomer, or a pharmaceutically acceptable salt, solvate, hydrate, clathrate, or prodrug thereof.

In another embodiment, the invention also encompasses an enantiomerically S isomer of a compound of formula I, II or III, substantially free of its R isomer, or a pharmaceutically acceptable salt, solvate, hydrate, clathrate, or prodrug thereof.

Enantiomeric and stereoisomeric mixtures of compounds of the invention can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

The invention further encompasses prodrugs of compounds encompassed by Formulae I, II and III. As used herein, and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of the invention that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff ed., 5th ed. 1995), and *Design of Prodrugs* (H. Bundgaard ed., Elselvier, N.Y. 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, -amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

The compounds of the invention are defined herein by their chemical structures and/or chemical names. Where a compound is referred to by both a chemical structure and a chemical name, and the chemical structure and chemical name conflict, the chemical structure is to be accorded more weight.

This invention provides pharmaceutical compositions comprising a therapeutically effective or a prophylactically effective amount of one or more compounds of the invention and a pharmaceutically acceptable vehicle or carrier. A pharmaceutically acceptable vehicle or carrier can comprise an excipient, diluent, or a mixture thereof. The term "therapeutically effective amount" means the amount of a compound of the invention that will elicit the biological or medical response in a mammal that is being that is being treated by the veterinarian or clinician. The term "prophylactically effective" means the amount of a compound of the invention that will prevent or inhibit affliction or mitigate affliction of a mammal with a medical condition that a veterinarian or clinician is trying to prevent, inhibit, or mitigate.

In another embodiment, the invention encompasses a method inhibiting PDE4 in a mammal comprising administering to said mammal an effective amount of a compound of the invention.

In another embodiment, the invention encompasses a method of modulating the production or lowering the levels of TNF-α in a mammal comprising administering to said mammal an effective amount of a compound of the invention.

In yet another embodiment, the invention encompasses a method of inhibiting MMP in a mammal comprising administering to said mammal an effective amount of a compound of the invention.

In yet another embodiment, the invention encompasses a method of treating undesired angiogenesis in a mammal comprising administering to said mammal an effective amount of a compound of the invention. Diseases associated with angiogenesis are well known in the art.

A separate embodiment of the invention encompasses methods of treating, preventing and managing Myelodysplastic Syndrome (MDS) which comprises administering to a patient in need of such treatment, prevention or management a therapeutically or prophylactically effective amount of a compound of the invention, or a pharmaceutically acceptable salt, solvate, hydrate, stereoisomer, clathrate, or prodrug thereof. MDS refers to a diverse group of hematopoietic stem cell disorders. MDS is characterized by a cellular marrow with impaired morphology and maturation (dysmyelopoiesis), peripheral blood cytopenias, and a variable risk of progression to acute leukemia, resulting from ineffective blood cell production. *The Merck Manual* 953 (17th ed. 1999) and List et al., 1990, *J. Clin. Oncol.* 8:1424.

Another separate embodiment of the invention encompasses methods of treating, preventing and managing Macular Degeneration (MD), which comprises administering to a patient in need of such treatment, prevention or management a therapeutically or prophylactically effective amount of a compound of the invention, or a pharmaceutically acceptable salt, solvate, hydrate, stereoisomer, clathrate, or prodrug thereof. MD refers to an eye disease that destroys central vision by damaging the macula.

A separate embodiment of the invention encompasses methods of treating, preventing and managing Myeloproliferative Disease (MPD) which comprises administering to a patient in need of such treatment, prevention or management a therapeutically or prophylactically effective amount of a compound of the invention, or a pharmaceutically acceptable salt, solvate, hydrate, stereoisomer, clathrate, or prodrug thereof. MPD refers to a group of disorders characterized by clonal abnormalities of the hematopoietic stem cell. See e.g., *Current Medical Diagnosis & Treatment*, pp. 499 (37th ed., Tierney et al. ed, Appleton & Lange, 1998).

The invention also encompasses a method of treating, preventing and managing Complex Regional Pain Syndrome (CRPS), which comprises administering to a patient in need of such treatment, prevention or management a therapeutically or prophylactically effective amount of a compound of the invention, or a pharmaceutically acceptable salt, solvate, hydrate, stereoisomer, clathrate, or prodrug thereof, before, during or after surgery or physical therapy directed at reducing or avoiding a symptom of complex regional pain syndrome in the patient.

In another embodiment, this invention encompasses a method of treating, preventing and managing a Central Nervous System (CNS) disorder, which comprises administering to a patient in need of such treatment, prevention or management a therapeutically or prophylactically effective amount of a compound of the invention, or a pharmaceutically acceptable salt, solvate, hydrate, stereoisomer, clathrate, or prodrug thereof.

In another embodiment, this invention encompasses a method of treating, preventing or managing an asbestos-related disease or disorder, which comprises administering to a patient in need of such treatment, prevention or management a therapeutically or prophylactically effective amount of a compound of the invention, or a pharmaceutically acceptable salt, solvate, hydrate, stereoisomer, clathrate, or prodrug thereof. Asbestos-related disease or disorder refers to a disease or disorder caused by an exposure to asbestos.

In still another embodiment, the invention encompasses methods of treating, preventing and managing cancer in a mammal, comprising administering to said mammal a therapeutically effective amount of a compound of the invention. The compounds of the invention can be used to treat, prevent or manage any cancer, for example, solid tumors and blood-born tumors. Specific examples of cancers treatable, preventable or manageable by compounds of the invention include, but are not limited to: cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are particularly useful for treating, preventing or managing cancers of the blood and bone marrow, such as multiple myeloma and acute and chronic leukemias, for example, lymphoblastic, myelogenous, lymphocytic, and myelocytic leukemias. The compounds of the invention can be used for treating, preventing or managing either primary or metastatic tumors.

In yet one more embodiment, the invention encompasses methods of treating, preventing and managing cancer in a mammal, comprising administering to a mammal in need thereof, a therapeutically effective amount of a compound of the invention and another therapeutic agent.

In yet another embodiment, the invention encompasses methods of treating, preventing and managing inflammatory disorders in a mammal, comprising administering to said mammal a therapeutically effective amount of a compound of the invention. The compounds of the invention are especially effective to treat, prevent or manage inflammatory diseases related to the up-regulation of TNF-α including, but not limited to, arthritic conditions, such as, rheumatoid arthritis, and osteoarthritis; rheumatoid spondylitis; psoriasis; post ischemic perfusion injury; inflammatory bowel disease; and chronic inflammatory pulmonary disease.

In one more embodiment still, the invention encompasses methods of treating, preventing and managing inflammatory disorders in a mammal, comprising administering to a mammal in need thereof, a therapeutically effective amount of a compound of the invention and another anti-inflammatory agent.

In a further embodiment, the invention encompasses methods of treating, preventing and managing heart disease in a mammal comprising administering to said mammal a therapeutically effective amount of a compound of the invention. For example, the compounds of the invention can be used to treat, prevent or manage congestive heart failure, cardiomyopathy, pulmonary edema, endotoxin-mediated septic shock, acute viral myocarditis, cardiac allograft rejection, and myocardial infarction.

In an additional embodiment, the invention encompasses methods of treating, preventing and managing osteoporosis in a mammal comprising administering to said mammal a therapeutically effective amount of a compound of the invention.

In a further embodiment, the invention encompasses methods of treating, preventing and managing viral, genetic, allergic, and autoimmune diseases. For example, the compounds are useful to treat, prevent or manage diseases including, but not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft versus host disease, graft rejection, auto-immune disease, rheumatoid spondylitis, Crohn's disease, ulcerative colitis, inflammatory-bowel disease, multiple sclerosis, systemic lupus erythrematosus, ENL in leprosy, radiation damage, cancer, asthma, or hyperoxic alveolar injury in a mammal comprising administering to said mammal a therapeutically effective amount of a compound of the invention.

In still another embodiment, the invention encompasses methods of treating, preventing and managing malaria, mycobacterial infection, or an opportunistic infection resulting from HIV in a mammal, comprising administering to said mammal a therapeutically effective amount of a compound of the invention.

In still one more embodiment, the invention relates to treating, preventing or managing mammals having more than one of the conditions treatable by a compound of the invention.

In the above embodiments, it is preferable that the mammal be in need of the treatment, prevention or management, that is, the mammal is actually suffering from a medical condition or at risk of a medical condition for which a compound of the invention can provide treatment, prevention or management. However, the compounds of the invention can also be administered to test animals that do not necessarily require such treatment, prevention or management.

In a further embodiment, the invention encompasses a method of modulating the production, preferably inhibiting, or lowering the levels of PDE4 in a mammalian cell or tissue comprising contacting an effective amount of a compound of the invention with said mammalian cell or tissue.

In a further embodiment, the invention encompasses a method of modulating the production or lowering the levels of TNF-α in a mammalian cell or tissue comprising contacting an effective amount of a compound of the invention with said mammalian cell or tissue.

In yet another embodiment, the invention encompasses a method of modulating the production or lowering the levels of MMP in a mammalian cell or tissue comprising contacting an effective amount of a compound of the invention with said mammalian cell or tissue.

In these embodiments, the term "effective amount" means the amount of the compound that will induce the biological response sought by the researcher, veterinarian, physician, or clinician. It should be understood that the cell can be in a cell culture or a tissue culture (in vitro) or in an organism (in vivo) including a human.

The present invention may be understood by reference to the detailed description and examples that are intended to exemplify non-limiting embodiments of the invention.

4.1. Preparation of the Compounds

The compounds can be prepared using methods which are known in general for the preparation of imides and 2,3-dihydro-1H-isoindolinones. However, the present invention also pertains to an improvement in the formation of the final compounds, as discussed below in greater detail.

An N-alkoxycarbonylimide and an amine thus are allowed to react in the presence of a base such as sodium carbonate or sodium bicarbonate substantially as described by Shealy et al., Chem. & Ind., (1965) 1030-1031) and Shealy et al., J. Pharm. Sci. 57, 757-764 (1968) to yield the N-substituted imide. Alternatively, a cyclic acid anhydride can be reacted with an appropriate amine to form an imide. Formation of a cyclic imide also can be accomplished by refluxing a solution of an appropriately substituted dicarboxylic acid monoamide in anhydrous tetrahydrofuran with N,N'-carbonyldiimidazole. Also, a 2-bromomethyl-benzoic ester can be reacted with an appropriate amine to form a 2,3-dihydro-1H-isoindolinone as shown below.

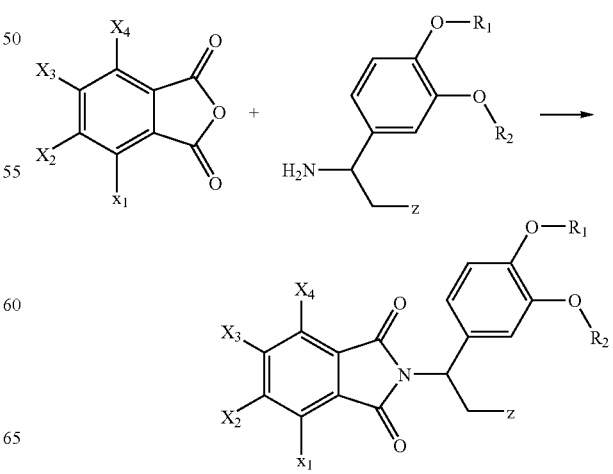

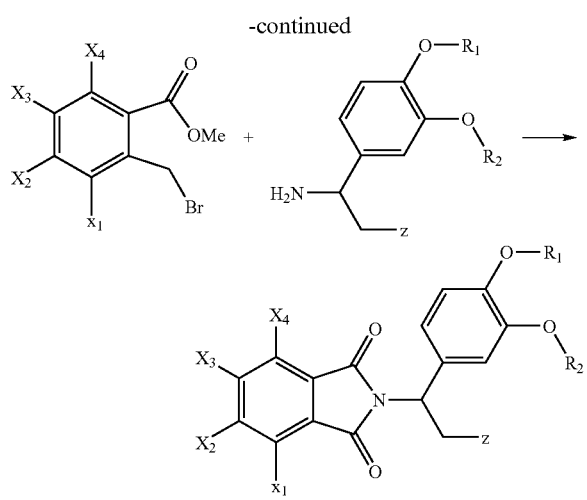

Other methods of formation are described in U.S. Pat. No. 5,605,914 and International Publication No. WO 01/34606 A1 which are incorporated herein in there entireties by reference.

4.2. Pharmaceutical Compositions

This invention provides pharmaceutical compositions comprising a pharmaceutically acceptable carrier, excipient or diluent and one or more compounds of the present invention.

One embodiment provides the subject compounds combined with a pharmaceutically acceptable excipient such as sterile saline, methylcellulose solutions, detergent solutions or other medium, water, gelatin, oils, etc. The compounds or compositions may be administered alone or in combination with any convenient carrier, diluent, etc., and such administration may be provided in single or multiple dosages. The compositions are sterile, particularly when used for parenteral delivery. However, oral unit dosage forms need not be sterile. Useful carriers include water soluble and water insoluble solids, fatty acids, micelles, inverse micelles, liposomes and semi-solid or liquid media, including aqueous solutions and non-toxic organic solvents. All of the above formulations may be treated with ultrasounds, stirred, mixed, high-shear mixed, heated, ground, milled, aerosolized, pulverized, lyophilized, etc., to form pharmaceutically acceptable compositions.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

The pharmaceutical compositions and methods of the present invention may further comprise other therapeutically active compounds, as noted herein, useful in the treatment of metabolic disorders, cardiovascular diseases, inflammatory conditions or neoplastic diseases and pathologies associated therewith (e.g., diabetic neuropathy) or other adjuvant. In many instances, compositions which include a compound of the invention and an alternative agent have additive or synergistic effects when administered.

4.3. Methods of Treatment, Prevention and Management

In accordance with the invention, a compound or composition of the invention is administered to a mammal, preferably, a human, with or at risk of a disease or medical condition, for example, cancer, such as solid tumors and blood-born tumors. Specific examples of cancers treatable, preventable or manageable by administering compounds of the invention include, but are not limited to, disease of skin tissues, organs, blood, and vessels, including, but not limited to, cancers of the bladder, bone or blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scelroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation; in particular, refractory to thalidomide.

The compounds of the invention are also useful to treat, prevent or manage heart disease, such as congestive heart failure, cardiomyopathy, pulmonary edema, endotoxin-mediated septic shock, acute viral myocarditis, cardiac allograft rejection, and myocardial infarction.

The compounds of the invention can also be used to treat, prevent or manage viral, genetic, inflammatory, allergic, and autoimmune diseases. For example, the compounds are useful to treat, prevent or manage diseases including, but not limited to, HIV; hepatitis; adult respiratory distress syndrome; bone-resorption diseases; chronic obstructive pulmonary disease, chronic pulmonary inflammatory diseases; dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft rejection; auto-immune disease; rheumatoid spondylitis; arthritic conditions, such as rheumatoid arthritis and osteoarthritis; osteoporosis, Parkinson's Disease, Crohn's disease; ulcerative colitis; inflammatory-bowel disease; multiple sclerosis; systemic lupus erythrematosus; ENL in leprosy; radiation damage; asthma; and hyperoxic alveolar injury.

The compounds of the invention are also useful for treating, preventing or managing bacterial infections including, but not limited to, malaria, mycobacterial infection, and opportunistic infections resulting from HIV.

Another embodiment of the invention encompasses methods of treating, managing or preventing diseases and disorders associated with, or characterized by, undesired angiogenesis, which comprise administering to a patient in need of such treatment, management or prevention a therapeutically or prophylactically effective amount of a compound of the invention, or a pharmaceutically acceptable salt, solvate, hydrate, stereoisomer, clathrate, or prodrug thereof.

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle), which are mediated by undesired or uncontrolled angiogenesis.

Other examples include, but are not limited to, diabetic retinopathy, retinopathy of prematurity, corneal graft rejection, neovascular glaucoma, retrolental fibroplasia, proliferative vitreoretinopathy, trachoma, myopia, optic pits, epidemic keratoconjunctivitis, atopic keratitis, superior limbic keratitis, pterygium keratitis sicca, sjogrens, acne rosacea, phylectenulosis, syphilis, lipid degeneration, bacterial ulcer, fungal ulcer, Herpes simplex infection, Herpes zoster infection, protozoan infection, Kaposi sarcoma, Mooren ulcer, Terrien's marginal degeneration, mariginal keratolysis, rheumatoid arthritis, systemic lupus, polyarteritis, trauma, Wegeners sarcoidosis, scleritis, Steven's Johnson disease, periphigoid radial keratotomy, sickle cell anemia, sarcoid, pseudoxanthoma elasticum, Pagets disease, vein occlusion, artery occlusion, carotid obstructive disease, chronic uveitis, chronic vitritis, Lyme's disease, Eales disease, Bechet's disease, retinitis, choroiditis, presumed ocular histoplasmosis, Bests disease, Stargarts disease, pars planitis, chronic retinal detachment, hyperviscosity syndromes, toxoplasmosis, rubeosis, sarcodisis, sclerosis, soriatis, psoriasis, primary sclerosing cholangitis, proctitis, primary biliary srosis, idiopathic pulmonary fibrosis, alcoholic hepatitis, endotoxemia, toxic shock syndrome, osteoarthritis, retrovirus replication, wasting, meningitis, silica-induced fibrosis, asbestos-induced fibrosis, malignancy-associated hypercalcemia, stroke, circulatory shock, periodontitis, gingivitis, macrocytic anemia, refractory anemia, 5q-syndrome, and veterinary disorder caused by feline immunodeficiency virus, equine infectious anemia virus, caprine arthritis virus, visna virus, maedi virus or lenti virus.

In certain embodiment of the invention, specific diseases do not include congestive heart failure, cardiomyopathy, pulmonary edema, endotoxin-mediated septic shock, acute viral myocarditis, cardiac allograft rejection, myocardial infarction, HIV, hepatitis, adult respiratory distress syndrome, bone-resorption disease, chronic obstructive pulmonary diseases, chronic pulmonary inflammatory disease, dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft rejection, rheumatoid spondylitis, osteoporosis, Parkinson's Disease, Crohn's disease, ulcerative colitis, inflammatory-bowel disease, multiple sclerosis, systemic lupus erythrematosus, erythema nodosum leprosum in leprosy, radiation damage, asthma, hyperoxic alveolar injury, malaria and mycobacterial infection.

The compounds of the invention are also useful for preventing heart disease, such as congestive heart failure, cardiomyopathy, pulmonary edema, endotoxin-mediated septic shock, acute viral myocarditis, cardiac allograft rejection, and myocardial infarction.

The compounds of the invention are also useful for treating, preventing or managing MDS and related syndromes, such as, but not limited to, refractory anemia (RA), RA with ringed sideroblasts (RARS), RA with excess blasts (RAEB), RAEB in transformation (RAEB-T), chronic myelomonocytic leukemia (CMML), and symptoms such as anemia, thrombocytopenia, neutropenia, cytopenias, bicytopenia (two deficient cell lines), and pancytopenia (three deficient cell lines).

The compounds of the invention are also useful for treating, preventing or managing CRPS and related syndromes. As used herein, and unless otherwise specified, the term "CRPS" refers to a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration). Unless otherwise indicated, the terms "complex regional pain syndrome," "CRPS" and "CRPS and related syndromes" include: type I, encompassing the condition known as reflex sympathetic dystrophy (RSD), which occurs after an initial noxious event other than a nerve injury; type II, encompassing the condition known as causalgia, which occurs after nerve injury; acute stage (usually hyperthermic phase of 2-3 months); dystrophic phase (showing vasomotor instability for several months); atrophic phase (usually cold extremity with atrophic changes); reflex neurovascular dystrophy; reflex dystrophy; sympathetic maintained pain syndrome; Sudeck atrophy of bone; algoneurodystrophy; shoulder hand syndrome; post-traumatic dystrophy; trigeminal neuralgia; post herpetic neuralgia; cancer related pain; phantom limb pain; fibromyalgia; chronic fatigue syndrome; radiculopathy; and other painful neuropathic conditions, e.g., diabetic neuropathy, luetic neuropathy, or painful neuropathic condition iatrogenically induced from drugs such as vincristine, velcade and thalidomide.

The compounds of the invention are useful for treating, preventing or managing all types of CRPS and related syndromes, including, but not limited to, those referred to as CRPS type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, post-operative pain, spinal cord injury pain, central post-stroke pain, radiculopathy, and other painful neuropathic conditions, e.g., diabetic neuropathy.

The compounds of the invention are also useful for treating, preventing and managing MD and related syndromes, such as, but not limited to, atrophic (dry) MD, exudative (wet) MD, age-related maculopathy (ARM), choroidal neovascularisation (CNVM), retinal pigment epithelium detachment (PED), and atrophy of retinal pigment epithelium (RPE).

As used herein, the term macular degeneration (MD) encompasses all forms of macular degenerative diseases regardless of a patient's age, although some macular degenerative diseases are more common in certain age groups. These include, but are not limited to, Best's disease or vitelliform (most common in patients under about 7 years of age); Stargardt's disease, juvenile macular dystrophy or fundus flavimaculatus (most common in patients between about 5 and about 20 years of age); Behr's disease, Sorsby's disease, Doyne's disease or honeycomb dystrophy (most common in patients between about 30 and about 50 years of age); and age-related macular degeneration (most common in patients of about 60 years of age or older).

Symptoms associated with MD and related syndromes include, but are not limited to, drusen rounded whitish-yellowish spots in the fundus, submacular disciform scar tissue, choroidal neovascularisation, retinal pigment epithelium detachment, atrophy of retinal pigment epithelium, abnormal blood vessels stemming from the choroid (the blood vessel-rich tissue layer just beneath the retina), a blurry or distorted area of vision, a central blind spot, pigmentary abnormalities, a continuous layer of fine granular material deposited in the inner part of Bruch's membrane, and a thickening and decreased permeability of Bruch's membrane.

Causes of MD include, but are not limited to, genetic, physical trauma, diseases such as diabetes, and infection, such as bacterial infection (e.g., leprosy and ENL in particular). The compounds of the invention can effectively treat, prevent or manage all types of MD and related syndromes or symptoms, regardless of their causes.

The compounds of the invention are also useful for treating, preventing or managing all types of MPD and related syndromes or symptoms. Examples of MPD that can be treated, prevented or managed by the compounds of the invention include, but are not limited to, polycythemia rubra vera (PRV), primary thromobocythemia (PT), chronic myelogenous leukemia (CML), and agnogenic myeloid metaplasia (AMM).

As used herein, the term "myeloproliferative disease," or "MPD," means a hematopoietic stem cell disorder characterized by one or more of the following: clonal expansion of a multipotent hematopoietic progenitor cell with the overproduction of one or more of the formed elements of the blood (e.g., elevated red blood cell count, elevated white blood cell count, and/or elevated platelet count), presence of Philadelphia chromosome or bcr-abl gene, teardrop poikilocytosis on peripheral blood smear, leukoerythroblastic blood pictuer, giant abnormal platelets, hypercellular bone marrow with reticular or collagen fibrosis, marked left-shifted myeloid series with a low percentage of promyelocytes and blasts, splenomegaly, thrombosis, risk of progression to acute leukemia or cellular marrow with impaired morphology. The term "myeloproliferative disease," or "MPD," unless otherwise noted, includes: polycythemia rubra vera (PRV), primary thromobocythemia (PT), chronic myelogenous leukemia (CML), and agnogenic myeloid metaplasia (AMM).

Symptoms associated with MPD include, but are not limited to, headache, dizziness, tinnitus, blurred vision, fatigue, night sweat, low-grade fever, generalized pruritus, epistaxis, blurred vision, splenomegaly, abdominal fullness, thrombosis, increased bleeding, anemia, splenic infarction, severe bone pain, hematopoiesis in the liver, ascites, esophageal varices, liver failure, respiratory distress, and priapism. Laboratory findings associated with MPD include, but are not limited to, clonal expansion of a multipotent hematopoietic progenitor cell with the overproduction of one or more of the formed elements of the blood (e.g., elevated red blood cell count, elevated white blood cell count, and/or elevated platelet count), presence of Philadelphia chromosome or bcr-abl gene, teardrop poikilocytosis on peripheral blood smear, leukoerythroblastic blood pictuer, giant abnormal platelets, hypercellular bone marrow with reticular or collagen fibrosis, and marked left-shifted myeloid series with a low percentage of promyelocytes and blasts.

The compounds of the invention are also useful for treating, preventing and managing all types of CNS disorders.

Examples of CNS disorders include, but are not limited to, Parkinson disease; Alzheimer disease, mild cognitive impairment; depression; defective long-term memory; Amyotrophic Lateral Sclerosis (ALS); CNS trauma; hypokinetic disorders; bradykinesia; slowness of movement; paucity of movement; impairment of dexterity; hypophonia; monotonic speech; muscular rigidity; masked faces; decreased blinking; stooped posture; decreased arm swinging when walking; micrographia; parkinsonian tremor; parkinsonian gait; postural instability; festinating gait; motion freezing; disturbances of cognition, mood, sensation, sleep or autonomic function; dementia; and sleep disorders.

In a specific embodiment, the central nervous system disorder to be prevented, treated and/or managed is Parkinson disease, Alzheimer disease, mild cognitive impairment, dementia, depression, defective long-term memory, Amyotrophic Lateral Sclerosis (ALS) or CNS trauma.

The invention encompasses methods of treating, preventing or managing central nervous system disorders, preferably Parkinson disease or Alzheimer disease. In one embodiment, the methods of the invention are used to treat, prevent or manage disorders related to movement, including, but not limited to, slow execution or bradykinesia, paucity of movement or akinesia, movement disorders that impair fine motor control and finger dexterity, and other manifestations of bradykinesia, such as, but not limited to, hypophonia and monotonic speech. In another embodiment, the methods of the invention are used to treat, prevent or manage disorders related to muscular rigidity, including, but not limited to, a uniform increase in resistance to passive movement, interruptions to passive movement, and combinations of rigidity and dystonia. In a specific embodiment, methods of the invention are used to treat inflammation associated with Parkinson or related disease. In yet another embodiment of the invention, disorders resembling Parkinsonian tremor are treated, prevented or managed by the methods of the invention, including but not limited to, tremors of the face, jaw, tongue, posture, and other tremors that are present at rest and that attenuate during movement. In another embodiment, the methods of the invention are used to treat, prevent or manage disorders in gait, including, but not limited to, those resembling parkinsonian gait, shuffling, short steps, a tendency to turn en bloc, and festinating gait. In another embodiment of the invention, nonmotor symptoms are treated, prevented or managed using the methods of the invention, including, but not limited to, disorders of mood, cognition, defective long-term memory, sensation, sleep, dementia, and depression. In other embodiment of the invention, secondary forms of parkinsonism are treated, prevented or managed by the methods of the invention, including, but not limited to, drug induced parkinsonism, vascular parkinsonism, multiple system atrophy, progressive supranuclear palsy, disorders with primary tau pathology, cortical basal ganglia degeneration, parkinsonism with dementia, hyperkinetic disorders, chorea, Huntington disease, dystonia, Wilson disease, Tourette syndrome, essential tremor, myoclonus, and tardive movement disorders. In other embodiment of the invention, other central nervous system disorders are treated, prevented or managed by the methods of the invention, including, but not limited to, Alzheimer disease, mild cognitive impairment, Amyotrophic Lateral Sclerosis (ALS) and CNS trauma.

The compounds of the invention are also useful for treating, preventing or managing an asbestos-related disease or disorder and related symptoms. Examples of asbestos-related diseases or disorders include, but are not limited to, malignant mesothelioma, asbestosis, malignant pleural effusion, benign pleural effusion, pleural plaque, pleural calcification, diffuse pleural thickening, round atelectasis, and bronchogenic carcinoma. It further encompasses methods of treating patients who have been previously treated for asbestos-related diseases or disorders but were not sufficiently responsive or were non-responsive, as well as those who have not previously been treated for the diseases or disorders. Because patients have heterogenous clinical manifestations and varying clinical outcomes, the treatment given to a patient may vary, depending on his/her prognosis. The skilled clinician will be able to readily determine without undue experimentation specific secondary agents and types of physical therapy that can be effectively used to treat an individual patient.

Symptoms of asbestos-related diseases or disorders include, but are not limited to, dyspnea, obliteration of the diaphragm, radiolucent sheet-like encasement of the pleura, pleural effusion, pleural thickening, decreased size of the chest, chest discomfort, chest pain, easy fatigability, fever, sweats and weight loss. Examples of patients at risk of asbestos-related diseases or disorders include, but are not limited to, those who have been exposed to asbestos in the workplace and their family members who have been exposed to asbestos embedded in the worker's clothing. Patients having familial history of asbestos-related diseases or disorders are also preferred candidates for preventive regimens.

4.4. Pharmaceutical Formulations

Administration of compounds of the invention can be systemic or local. In most instances, administration to a mammal will result in systemic release of the compounds of the invention (i.e., into the bloodstream). Methods of administration include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. Preferably, the compounds and compositions of the invention are administered orally. In specific embodiments, it may be desirable to administer one or more compounds of the invention locally to the area in need of treatment. This may be achieved, for example, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

The compounds of the invention can be administered via typical as well as non-standard delivery systems, e.g., encapsulation in liposomes, microparticles, microcapsules, capsules, etc. For example, the compounds and compositions of the invention can be delivered in a vesicle, in particular a liposome (see Langer, 1990, *Science* 249:1527-1533; Treat et al., in Liposomes in *Therapy of Infectious Disease and Cancer*, Lopez-Berestein and Fidler (eds.), Liss, New York, pp. 353-365 (1989); Lopez-Berestein, ibid., pp. 317-327; see generally ibid.). In another example, the compounds and compositions of the invention can be delivered in a controlled release system. In one embodiment, a pump may be used (see Langer, supra; Sefton, 1987, *CRC Crit. Ref. Biomed. Eng.* 14:201; Buchwald et al., 1980, *Surgery* 88:507 Saudek et al., 1989, *N. Engl. J. Med.* 321:574). In another example, polymeric materials can be used (see Medical Applications of Controlled Release, Langer and Wise (eds.), CRC Press., Boca Raton, Fla. (1974); Controlled Drug Bioavailability, Drug Product Design and Performance, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71: 105). In still another example, a controlled-release system can be placed in proximity of the target area to be treated, e.g., the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, 1990, *Science* 249:1527-1533) can be used.

When administered as a composition, a compound of the invention will be formulated with a suitable amount of a pharmaceutically acceptable vehicle or carrier so as to provide the form for proper administration to the mammal. The term "pharmaceutically acceptable" means approved by a regulatory agency of the Federal or a state government or listed in the U.S. Pharmacopeia or other generally recognized pharmacopeia for use in mammals, and more particularly in humans. The term "vehicle" refers to a diluent, adjuvant, excipient, or carrier with which a compound of the invention is formulated for administration to a mammal. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. Preferably, when administered to a mammal, the compounds and compositions of the invention and pharmaceutically acceptable vehicles, excipients, or diluents are sterile. An aqueous medium is a preferred vehicle when the compound of the invention is administered intravenously, such as water, saline solutions, and aqueous dextrose and glycerol solutions.

The present compounds and compositions can take the form of capsules, tablets, pills, pellets, lozenges, powders, granules, syrups, elixirs, solutions, suspensions, emulsions, suppositories, or sustained-release formulations thereof, or any other form suitable for administration to a mammal. In a preferred embodiment, the compounds and compositions of the invention are formulated for administration in accordance with routine procedures as a pharmaceutical composition adapted for oral or intravenous administration to humans. In one embodiment, the pharmaceutically acceptable vehicle is a hard gelatin capsule. Examples of suitable pharmaceutical vehicles and methods for formulation thereof are described in *Remington: The Science and Practice of Pharmacy*, Alfonso R. Gennaro ed., Mack Publishing Co. Easton, Pa., 19th ed., 1995, Chapters 86, 87, 88, 91, and 92, incorporated herein by reference.

Compounds and compositions of the invention formulated for oral delivery, are preferably in the form of capsules, tablets, pills, or any compressed pharmaceutical form. Moreover, where in tablet or pill form, the compounds and compositions may be coated to delay disintegration and absorption in the gastrointestinal tract thereby providing a sustained action over an extended period of time. Selectively permeable membranes surrounding an osmotically active driving compound are also suitable for orally administered compounds and compositions of the invention. In these later platforms, fluid from the environment surrounding the capsule is imbibed by the driving compound that swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles, excipients, and diluents, such as magnesium stearate, sodium saccharine, cellulose, magnesium carbonate, lactose, dextrose, sucrose, sorbitol, mannitol, starch, gum acacia, calcium silicate, microcrystalline cellulose, polyvinylpyrrolidinone, water, syrup, and methyl cellulose, the formulations can additionally include lubricating agents, such as talc, magnesium stearate, mineral oil, wetting agents, emulsifying and suspending agents, preserving agents such as methyl- and propylhydroxybenzoates. Such vehicles are preferably of pharmaceutical grade. Orally administered compounds and compositions of the invention can optionally include one or more sweetening agents, such as fructose, aspartame or saccharin; one or more flavoring agents such as peppermint, oil of wintergreen, or cherry; or one or more coloring agents to provide a pharmaceutically palatable preparation.

A therapeutically effective dosage regimen for the treatment of a particular disorder or condition will depend on its nature and severity, and can be determined by standard clinical techniques according to the judgment of a medical practitioner. In addition, in vitro or in vivo assays can be used to help identify optimal dosages. Of course, the amount of a compound of the invention that constitutes a therapeutically effective dose also depends on the administration route. In general, suitable dosage ranges for oral administration are about 0.001 milligrams to about 20 milligrams of a compound of the invention per kilogram body weight per day, preferably, about 0.7 milligrams to about 6 milligrams, more preferably, about 1.5 milligrams to about 4.5 milligrams. In a preferred embodiment, a mammal, preferably, a human is orally administered about 0.01 mg to about 1000 mg of a compound of the invention per day, more preferably, about 0.1 mg to about 300 mg per day, or about 1 mg to about 100 mg in single or divided doses. The dosage amounts described herein refer to total amounts administered; that is, if more than one compound of the invention is administered, the preferred dosages correspond to the total amount of the compounds of the invention administered. Oral compositions preferably contain 10% to 95% of a compound of the invention by weight. Preferred unit oral-dosage forms include pills, tablets, and capsules, more preferably capsules. Typically such unit-dosage forms will contain about 0.01 mg, 0.1 mg, 1 mg, 5 mg, 10 mg, 15 mg, 20 mg, 50 mg, 100 mg, 250 mg, or 500 mg of a compound of the invention, preferably, from about 5 mg to about 200 mg of compound per unit dosage.

In another embodiment, the compounds and compositions of the invention can be administered parenterally (e.g., by intramuscular, intrathecal, intravenous, and intraarterial routes), preferably, intravenously. Typically, compounds and compositions of the invention for intravenous administration are solutions in sterile isotonic aqueous vehicles, such as water, saline, Ringer's solution, or dextrose solution. Where necessary, the compositions may also include a solubilizing agent. Compositions for intravenous administration may optionally include a local anesthetic such as lignocaine to ease pain at the site of the injection. For intravenous administration, the compounds and compositions of the invention can be supplied as a sterile, dry lyophilized powder or water-free concentrate in a hermetically sealed container, such as an ampule or sachette, the container indicating the quantity of active agent. Such a powder or concentrate is then diluted with an appropriate aqueous medium prior to intravenous administration. An ampule of sterile water, saline solution, or other appropriate aqueous medium can be provided with the powder or concentrate for dilution prior to administration. Or the compositions can be supplied in pre-mixed form, ready for administration. Where a compound or composition of the invention is to be administered by intravenous infusion, it can be dispensed, for example, with an infusion bottle containing sterile pharmaceutical-grade water, saline, or other suitable medium.

Rectal administration can be effected through the use of suppositories formulated from conventional carriers such as cocoa butter, modified vegetable oils, and other fatty bases. Suppositories can be formulated by well-known methods using well-known formulations, for example see *Remington: The Science and Practice of Pharmacy*, Alfonso R. Gennaro ed., Mack Publishing Co. Easton, Pa., 19th ed., 1995, pp. 1591-1597, incorporated herein by reference To formulate and administer topical dosage forms, well-known transdermal and intradermal delivery mediums such as lotions, creams, and ointments and transdermal delivery devices such as patches can be used (Ghosh, T. K.; Pfister, W. R.; Yum, S. I. *Transdermal and Topical Drug Delivery Systems*, Interpharm Press, Inc. p. 249-297, incorporated herein by reference). For example, a reservoir type patch design can comprise a backing film coated with an adhesive, and a reservoir compartment comprising a compound or composition of the invention, that is separated from the skin by a semipermeable membrane (e.g., U.S. Pat. No. 4,615,699, incorporated herein by reference). The adhesive coated backing layer extends around the reservoir's boundaries to provide a concentric seal with the skin and hold the reservoir adjacent to the skin.

Mucosal dosage forms of the invention include, but are not limited to, ophthalmic solutions, sprays and aerosols, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

The compounds of the invention may also be administered directly to the lung by inhalation. For administration by inhalation, a compound of the invention can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a compound of formula I directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a compound of the invention to the lung (See, e.g., Raleigh et al., *Proc. Amer. Assoc. Cancer Research Annual Meeting*, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a compound of the invention to the lung is a liquid spray device supplied, for example, by Aradigm Corporation. Liquid spray systems use extremely small nozzle holes to aerosolize liquid drug formulations that can then be directly inhaled into the lung.

In a preferred embodiment, a nebulizer device is used to deliver a compound of the invention to the lung. Nebulizers create aerosols from liquid drug formulations by using, for example, ultrasonic energy to form fine particles that can be readily inhaled (See e.g., Verschoyle et al., *British J Cancer*, 1999, 80, Suppl 2, 96, which is herein incorporated by reference). Examples of nebulizers include devices supplied by Sheffield/Systemic Pulmonary Delivery Ltd. (See, Anner et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics In a particularly preferred embodiment, an electrohydrodynamic ("EHD") aerosol device is used to deliver a compound of the invention to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the formulation containing compounds of the invention may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery will be known to the skilled artisan and are within the scope of the invention.

Liquid drug formulations suitable for use with nebulizers and liquid spray devices and EHD aerosol devices will typically include a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of a compound of the invention. Preferably, this material is liquid such as an alcohol, glycol, polyglycol or a fatty acid. Other methods of formulating liquid drug solutions or suspension suitable for use in aerosol devices are known to those of skill in the art (See, e.g., Biesalski, U.S. Pat. Nos. 5,112,598; Biesalski, 5,556,611, which are herein incorporated by reference). A compound of the invention can also be formulated in rectal or vaginal compositions such as suppositories or retention enemas, e.g., containing conventional suppository bases such as cocoa butter or other glycerides.

In addition to the formulations described previously, a compound of the invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver compounds of the inventions. Certain organic solvents such as dimethylsulfoxide can also be employed, although usually at the cost of greater toxicity. A compound of the invention can also be delivered in a controlled release system. In one embodiment, a pump can be used (Sefton, CRC Crit. Ref Biomed Eng., 1987, 14, 201; Buchwald et al., *Surgery,* 1980, 88, 507; Saudek et al., *N. Engl. J Med,* 1989, 321, 574). In another embodiment, polymeric materials can be used (see *Medical Applications of Controlled Release,* Langer and Wise (eds.), CRC Pres., Boca Raton, Fla. (1974); *Controlled Drug Bioavailability, Drug Product Design and Performance,* Smolen and Ball (eds.), Wiley, New York (1984); Ranger and Peppas, *J Macromol. Sci. Rev. Macromol. Chem.,* 1983, 23, 61; see also Levy et al., *Science* 1985, 228, 190; During et al., *Ann. Neurol.,* 1989, 25, 351; Howard et al., 1989, *J. Neurosurg.* 71, 105). In yet another embodiment, a controlled-release system can be placed in proximity of the target of the compounds of the invention, e.g., the lung, thus requiring only a fraction of the systemic dose (see, e.g., Goodson, in *Medical Applications of Controlled Release,* supra, vol. 2, pp. 115 (1984)). Other controlled-release system can be used (see e.g. Langer, *Science,* 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In one embodiment, the kit contains more than one compound of the invention. In another embodiment, the kit comprises a compound of the invention and another biologically active agent.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred. The compounds and compositions of the invention may also be demonstrated to be effective and safe using animal model systems. Other methods will be known to the skilled artisan and are within the scope of the invention.

4.5. Combination Therapy

In certain embodiments, a compound of the invention is administered to a mammal, preferably, a human concurrently with one or more other therapeutic agents, or with one or more other compounds of the invention, or with both. By "concurrently," it is meant that a compound of the invention and the other agent are administered to a mammal in a sequence and within a time interval such that the compound of the invention can act together with the other agent to provide an increased or synergistic benefit than if they were administered otherwise. For example, each component may be administered at the same time or sequentially in any order at different points in time; however, if not administered at the same time, they should be administered sufficiently closely in time so as to provide the desired treatment effect. Preferably, all components are administered at the same time, and if not administered at the same time, preferably, they are all administered from about 6 hours to about 12 hours apart from one another.

When used in combination with other therapeutic agents, the compounds of the invention and the therapeutic agent can act additively or, more preferably, synergistically. In one embodiment, a compound or a composition of the invention is administered concurrently with another therapeutic agent in the same pharmaceutical composition. In another embodiment, a compound or a composition of the invention is administered concurrently with another therapeutic agent in separate pharmaceutical compositions. In still another embodiment, a compound or a composition of the invention is administered prior or subsequent to administration of another therapeutic agent. As many of the disorders for which the compounds and compositions of the invention are useful in treating are chronic disorders, in one embodiment combination therapy involves alternating between administering a compound or a composition of the invention and a pharmaceutical composition comprising another therapeutic agent, e.g., to minimize the toxicity associated with a particular drug. In certain embodiments, when a composition of the invention is administered concurrently with another therapeutic agent that potentially produces adverse side effects including, but not limited to toxicity, the therapeutic agent can advantageously be administered at a dose that falls below the threshold that the adverse side effect is elicited. Additional therapeutic agents include, but are not limited to, hematopoietic growth factors, cytokines, anti-cancer agents, antibiotics, immunosuppressive agents, steroids, antihistamines, lukatriene inhibitors and other therapeutics discussed herein.

Preferred additional therapeutic agents include, but are not limited to, Remicade™, docetaxel, Celecoxib™, melphalan, dexamethasone, steroids, gemcitabine, cisplatinum, temozolomide, etoposide, cyclophosphamide, temodar, carboplatin, procarbazine, gliadel, tamoxifen, topotecan, methotrexate, Arisat®, Taxol™, taxotere, fluorouracil, leucovorin, irinotecan, xeloda, CPT-11, interferon alpha, pegylated interferon alpha, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, PEG INTRON-A, doxil, vincristine, decadron, doxorubicin, paclitaxel, ganciclovir, adriamycin, estramustine, Emcyt, sulindac, and etoposide.

The invention further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Recombinant and mutated forms of G-CSF can be prepared as described in U.S. Pat. Nos. 4,810,643; 4,999,291; 5,528,823; and 5,580,755; all of which are incorporated herein by reference. Recombinant and mutated forms of GM-CSF can be prepared as described in U.S. Pat. Nos. 5,391,485; 5,393,870; and 5,229,496; all of which are incorporated herein by reference. In fact, recombinant forms of G-CSF and GM-CSF are currently sold in the United States for the treatment of symptoms associated with specific chemotherapies. A recombinant form of G-CSF known as filgrastim is sold in the United States under the trade name NEUPOGEN®, and is indicated to decrease the incidence of infection, as manifested by febrile neutropenia, in patients with nomyeloid malignancies receiving myelosuppressive anti-cancer drugs associated with a significant incidence of severe neutropenia with fever. *Physicians' Desk Reference,* 587-592 (56$^{th}$ ed., 2002). A recombinant form of GM-CSF known as sargramostim is also sold in the United States under the trade name LEUKINE™. LEUKINE™ is indicated for use following induction chemotherapy in older adult patients with acute myelogenous leukemia (AML) to shorten time to neutrophil recovery. *Physicians' Desk Reference,* 1755-1760 (56$^{th}$ ed., 2002). A recombinant form of EPO known as epoetin alfa is sold in the United States under the trade name EPOGEN™. EPOGEN™ is used to stimulate red cell production by stimulating division and maturation of committed red cell precursor cells. *Physicians' Desk Reference,* 582-587 (56$^{th}$ ed., 2002).

A growth-factor or cytokine such as G-CSF, GM-CSF and EPO can also be administered in the form of a vaccine. For example, vaccines that secrete, or cause the secretion of, cytokines such as G-CSF and GM-CSF can be used in the methods, pharmaceutical compositions, and kits of the invention. See, e.g., Emens, L. A., et al., *Curr. Opinion Mol. Ther.* 3(1):77-84 (2001).

Examples of anti-cancer drugs that can be used in the various embodiments of the invention, including the methods, dosing regimens, cocktails, pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; dacarbazine; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; cartilage derived inhibitor; carzelesin; casein kinase inhibitors (ICOS);

castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; diethylnorspermine; dihydro-5-azacytidine; dihydrotaxol; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In one embodiment of the invention, the compounds of the invention can be used, not only to directly treat the disorder, but also to reduce the dose or toxicity of another chemotherapeutic. For example, the compounds of the invention can be administered to reduce gastrointestinal toxicity associated with a topoisomerase inhibitor, such as irinotecan.

4.6. Biological Assays

Compounds having PDE 4, TNF-α, and MMP inhibitory activity can be assayed using methods commonly known in the art including, but not limited to, enzyme immunoassay, radioimmunoassay, immunoelectrophoresis, and affinity labeling. Further assays which can be utilized include LPS-induced TNF and PDE4 enzymatic assays and the methods set out in International Patent Publication Nos. WO 01/90076 A1 WO 01/34606 A1 each of which are incorporated herein in their entireties by reference.

PBMC from normal donors are obtained by Ficoll-Hypaque density centrifugation. Cells are cultured in RPMI supplemented with 10%, AB+serum, 2 mM L-glutamine, 100 U/mL penicillin and 100 mg/mL streptomycin.

The test compounds are dissolved in dimethylsulfoxide (Sigma Chemical), further dilutions are done in supplemented RPMI. The final dimethylsulfoxide concentration in the presence or absence of drug in the PBMC suspensions is 0.25 wt %. The test compounds are assayed at half-log dilutions starting in 50 mg/mL. The test compounds are added to PBMC ($10^6$ cells/mL) in 96 wells plates one hour before the addition of LPS.

PBMC ($10^6$ cells/mL) in the presence or absence of test compounds are stimulated by treatment with 1 mg/mL of LPS from *Salmonella minnesota* R595 (List Biological Labs, Campbell, Calif.). Cells are then incubated at 37° C. for 18-20 hours. Supernatants are harvested and assayed immediately for TNFα levels or kept frozen at −70° C. (for not more than 4 days) until assayed.

The concentration of TNFα in the supernatant is determined by human TNFα ELISA kits (ENDOGEN, Boston, Mass.) according to the manufacturer's directions.

Phosphodiesterase can be determined in conventional models. For example, using the method of Hill and Mitchell, U937 cells of the human promonocytic cell line are grown to $1 \times 10^6$ cells/mL and collected by centrifugation. A cell pellet of $1 \times 10^9$ cells is washed in phosphate buffered saline and then frozen at −70° C. for later purification or immediately lysed in cold homogenization buffer (20 mM Tris-HCl, pH 7.1, 3 mM 2-mercaptoethanol, 1 mM magnesium chloride, 0.1 mM ethylene glycol-bis-(β-aminoethyl ether)-N,N,N',N'-tetraacetic acid (EGTA), 1 µM phenyl-methylsulfonyl fluoride (PMSF), and 1 µg/mL leupeptin). Cells are homogenized with 20 strokes in a Dounce homogenizer and supernatant containing the cytosolic fraction are obtained by centrifugation. The supernatant then is loaded onto a Sephacryl S-200 column equilibrated in homogenization buffer. Phosphodiesterase is eluted in homogenization buffer at a rate of approximately 0.5 mL/min and fractions are assayed for phosphodiesterase activity−/+rolipram. Fractions containing phosphodiesterase activity (rolipram sensitive) are pooled and aliquoted for later use.

The phosphodiesterase assay is carried out in a total volume of 100 µl containing various concentration of test compounds, 50 mM Tris-HCl, pH 7.5, 5 mM magnesium chloride, and 1 µM cAMP of which 1% was $^3$H cAMP. Reactions are incubated at 30° C. for 30 minutes and terminated by boiling for 2 minutes. The amount of phosphodiesterase IV containing extract used for these experiments is predetermined such that reactions are within the linear range and consumed less than 15% of the total substrate. Following termination of reaction, samples are chilled at 4° C. and then treated with 10 µl 10 mg/mL snake venom for 15 min at 30° C. Unused substrate then is removed by adding 200 µl of a quaternary ammonium ion exchange resin (AG1-X8, BioRad) for 15 minutes. Samples then are spun at 3000 rpm, 5 min and 50 µl of the aqueous phase are taken for counting. Each data point is carried out in duplicate and activity is expressed as percentage of control. The $IC_{50}$ of the compound then is determined from dose response curves of a minimum of three independent experiments.

The following examples are offered by way of illustration and are not intended to limit the scope of the invention.

5. EXAMPLES

Reagents and solvents used below can be obtained from commercial sources such as Aldrich Chemical Co. (Milwaukee, Wis., USA). $^1$H-NMR and $^{13}$C-NMR spectra were recorded on a Bruker AC 250 MHz NMR spectrometer. Significant peaks are tabulated in the order: chemical shift, multiplicity (s, singlet; d, doublet; t, triplet; q, quartet; m, multiplet; br s, broad singlet), coupling constant(s) in Hertz (Hz) and number of protons.

5.1. Example 1

(1R)-Cyclopropanecarboxylic acid {2-[1-(3-ethoxy-4-methoxy-phenyl)-3-hydroxy-propyl]-3-oxo-2,3-dihydro-1H-isoindol-4-yl}-amide

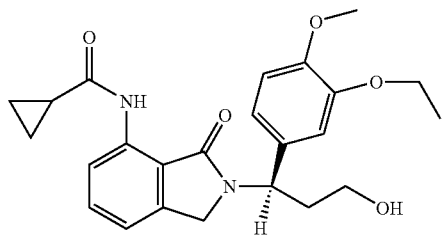

A solution of (3R)-3-amino-3-(3-ethoxy-4-methoxy-phenyl)-propan-1-ol (1.1 g, 4.9 mmol), 2-bromomethyl-6-(cyclopropanecarbonyl-amino)-benzoic acid methyl ester (1.5 g, 4.8 mmol) and triethylamine (0.75 mL, 5.4 mmol) in DMF (10 mL) was heated at 100° C. for 18 hrs. The solvent was removed in vacuo. The residue was extracted with ethyl acetate (50 mL) and water (50 mL). The organic layer was washed with HCl (1N, 50 mL), brine (50 mL), and dried over MgSO$_4$. The solvent was removed in vacuo to give an oil. The oil was stirred in ether (5 mL) and hexane (5 mL) to give a suspension. The suspension was filtered to give (1R)-cyclopropanecarboxylic acid {2-[1-(3-ethoxy-4-methoxy-phenyl)-3-hydroxy-propyl]-3-oxo-2,3-dihydro-1H-isoindol-4-yl}-amide as a white solid (1.3 g, 64% yield): mp, 103-105° C.; $^1$H NMR (CDCl$_3$) δ 0.86-0.93 (m, 2H, CH$_2$), 1.08-1.12 (m, 2H, CH$_2$), 1.44 (t, J=7 Hz, 3H, CH$_3$), 1.64-1.73 (m, 1H, CH), 2.11-2.32 (m, 2H, CH$_2$), 3.37 (dd, J=4, 9 Hz, 1H, OH), 3.50-3.59 (m, 1H, CHH), 3.74-3.79 (m, 2H, NCHH, CHH), 3.80 (s, 3H, CH$_3$), 4.06 (q, J=7 Hz, 2H, CH$_2$), 4.16 (d, J=18 Hz, 1H, NCHH), 6.65 (dd, J=4, 11 Hz, 1H, NCH), 6.83-6.99 (m, 4H, Ar), 7.44 (t, J=8 Hz, 1H, Ar), 8.45 (d, J=8 Hz, 1H, Ar), 10.52 (s, 1H, NH); $^{13}$C NMR (CDCl$_3$) δ8.35, 14.77, 16.22, 33.85, 46.23, 50.52, 55.98, 58.59, 64.55, 111.36, 112.99, 116.77, 116.99, 117.83, 119.77, 130.73, 133.37, 138.05, 141.49, 148.62, 149.25, 170.33, 172.76; Anal Calcd for $C_{24}H_{28}N_2O_5$: C, 67.91; H, 6.65; N, 6.60. Found: C, 67.92; H, 6.67; N, 6.37.

5.2. Example 2

(3R)-(tert-Butoxy)-N-{3-[7-(cyclopropylcarbonylamino)-1-oxoisoindolin-2-yl]-3-(3-ethoxy-4-methoxyphenyl)propyl}carbonylamino(tert-butoxy)formate

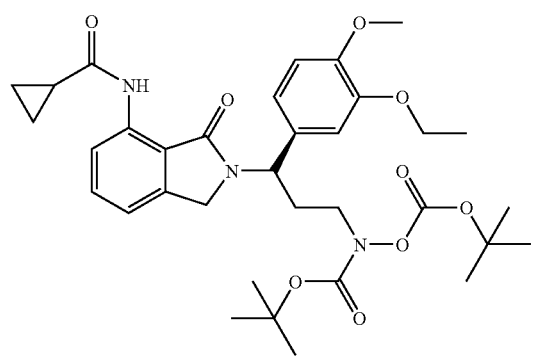

A solution of (3R)—N-[3-(7-amino-1-oxoisoindolin-2-yl)-3-(3-ethoxy-4-methoxyphenyl)propyl](tert-butoxy)carbonylamino(tert-butoxy)formate (4.1 g, 7.2 mmol), cyclopropanecarbonyl chloride (0.80 mL, 8.8 mmol) and triethylamine (1.3 mL, 9.3 mmol) in THF (20 mL) was heated at reflux for 2 hrs. The solution was extracted with ethyl acetate (100 mL) and sodium hydrogen carbonate (sat, 50 mL). The organic layer was washed with sodium hydrogen carbonate (sat, 50 mL), brine (50 mL), and dried over $MgSO_4$. The solvent was removed in vacuo to give (3R)-(tert-Butoxy)-N-{3-[7-(cyclopropylcarbonylamino)-1-oxoisoindolin-2-yl]-3-(3-ethoxy-4-methoxyphenyl)propyl}carbonylamino(tert-butoxy)formate as a white solid (4.4 g, 95% yield): mp, 153-155° C.; $^1$H NMR ($CDCl_3$) δ 0.84-0.92 (m, 2H, $CH_2$), 1.06-1.13 (m, 2H, $CH_2$), 1.42 (s, 9H, $3CH_3$), 1.43 (t, J=7 Hz, 3H, $CH_3$), 1.50 (s, 9H, $3CH_3$), 1.65-1.73 (m, 1H, CH), 2.38-2.48 (m, 2H, $CH_2$), 3.61-3.73 (m, 2H, $CH_2$), 3.85 (s, 3H, $CH_3$), 4.03 (d, J=18 Hz, 1H, NCHH), 4.04 (q, J=7 Hz, 2H, $CH_2$), 4.33 (d, J=18 Hz, 1H, NCHH), 5.47 (t, J=7 Hz, 1H, NCH), 6.81-7.00 (m, 4H, Ar), 7.42 (t, J=8 Hz, 1H, Ar), 8.42 (d, J=8 Hz, 1H, Ar), 10.61 (s, 1H, NH); $^{13}$C NMR ($CDCl_3$) δ8.21, 14.76, 16.16, 27.58, 28.03, 29.14, 46.21, 47.93, 52.21, 55.96, 58.45, 64.54, 82.57, 85.01, 111.45, 112.58, 116.73, 117.54, 117.67, 119.37, 131.36, 133.08, 138.02, 141.39, 148.59, 149.12, 152.21, 154.61, 169.50, 172.70; Anal Calcd for $C_{34}H_{45}N_3O_9$: C, 63.83; H, 7.09; N, 6.57. Found: C, 63.84; H, 7.03; N, 6.44.

5.3. Example 3

(1R)-Cyclopropanecarboxylic acid {2-[1-(3-ethoxy-4-methoxy-phenyl)-3-hydroxyamino-propyl]-3-oxo-2,3-dihydro-1H-isoindol-4-yl}-amide

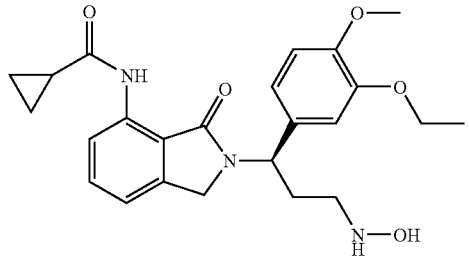

A solution of (3R)-(tert-Butoxy)-N-{3-[7-(cyclopropylcarbonylamino)-1-oxoisoindolin-2-yl]-3-(3-ethoxy-4-methoxyphenyl)propyl}carbonylamino(tert-butoxy)formate (4.1 g, 6.4 mmol) in methylene chloride (20 mL) and trifluoromethylacetic acid (9 mL)was stirred at room temperature for 1.5 hrs. The solvent was removed in vacuo to give a yellow oil. The oil was extracted with ethyl acetate (50 mL) and sodium hydrogen carbonate (sat, 50 mL). The organic layer was washed with brine (50 mL), and dried over $MgSO_4$. The solvent was removed in vacuo to give an oil. The oil was slurried in ether (15 mL) to give a suspension. The suspension was filtered to give (3R)-cyclopropanecarboxylic acid {2-[1-(3-ethoxy-4-methoxy-phenyl)-3-hydroxyamino-propyl]-3-oxo-2,3-dihydro-1H-isoindol-4-yl}-amide as white solid (2.1 g, 75% yield): mp, 136-138° C.; $^1$H NMR ($CDCl_3$) δ 0.84-0.91 (m, 2H, $CH_2$), 1.06-1.14 (m, 2H, $CH_2$), 1.43 (t, J=7 Hz, 3H, $CH_3$), 1.64-1.71 (m, 1H, CH), 2.23-2.45 (m, 2H, $CH_2$), 2.99 (t, J=7 Hz, 2H, $CH_2$), 3.85 (s, 3H, $CH_3$), 3.95 (d, J=16 Hz, 1H, NCHH), 4.06 (q, J=7 Hz, 2H, $CH_2$), 4.26 (d, J=16 Hz, 1H, NCHH), 5.57 (dd, J=6, 10 Hz, 1H, NCH), 6.81-6.99 (m, 4H, Ar), 7.41 (t, J=8 Hz, 1H, Ar), 8.42 (d, J=8 Hz, 1H, Ar), 10.57 (s, 1H, NH); $^{13}$C NMR ($CDCl_3$) δ8.27, 14.77, 16.19, 28.83, 45.79, 50.40, 51.49, 55.96, 64.57, 111.44, 112.84, 116.73, 117.39, 117.73, 119.52, 131.27, 133.13, 137.99, 141.36, 148.62, 149.18, 169.55, 172.72; Anal Calcd for $C_{24}H_{29}N_3O_5$: C, 65.59; H, 6.65; N, 9.56. Found: C, 65.30; H, 6.63; N, 9.21.

5.4. Example 4

(1R)-Cyclopropanecarboxylic acid {2-[1-(3-ethoxy-4-methoxy-phenyl)-3-methanesulfonylamino-propyl]-3-oxo-2,3-dihydro-1H-isoindol-4-yl}-amide

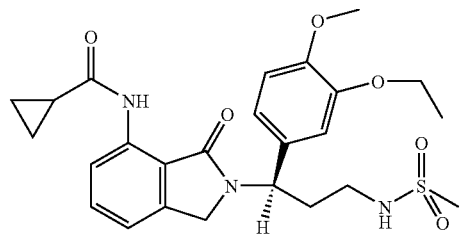

To a solution of (1R)-cyclopropanecarboxylic acid {2-[3-amino-1-(3-ethoxy-4-methoxy-phenyl)-propyl]-3-oxo-2,3-dihydro-1H-isoindol-4-yl}-amide (0.45 g, 1.1 mmol) and triethylamine (0.3 mL, 2 mmol) in methylene chloride (10 mL) was added methane sulfonyl chloride (0.10 mL, 1.3 mmol) at 0° C. After 3 hrs, the mixture was extracted with methylene chloride (20 mL) and water (20 mL). The organic layer was washed with HCl (1N, 20 mL), sodium hydrogen carbonate (sat 20 mL), brine (20 mL), and dried over $MgSO_4$. The solvent was removed in vacuo to give a solid, which was purified with chromatography (Silica Gel) to give (1R)-cyclopropanecarboxylic acid {2-[1-(3-ethoxy-4-methoxy-phenyl)-3-methanesulfonylamino-propyl]-3-oxo-2,3-dihydro-1H-isoindol-4-yl}-amide as a white solid (320 mg, 58% yield): mp, 93-95° C.; $^1$H NMR ($CDCl_3$) δ 0.89-0.93 (m, 2H, $CH_2$), 1.08-1.10 (m, 2H, $CH_2$), 1.42 (t, J=7 Hz, 3H, $CH_3$), 1.65-1.72 (m, 1H, CH), 2.27-2.32 (m, 2H, $CH_2$), 2.94 (s, 3H, $CH_3$), 2.97-3.06 (m, 1H, CHH), 3.85 (s, 3H, $CH_3$), 3.50 (d, J=17 Hz, 1H, NCHH), 4.04 (q, J=7 Hz, 2H, $CH_2$), 4.18 (d, J=17 Hz, 1H, NCHH), 5.51 (dd, J=6, 9 Hz, 1H, NCH), 5.60-5.62 (m, 1H, NH), 6.81-6.99 (m, 4H, Ar), 7.42 (t, J=8 Hz, 1H, Ar), 8.42 (d, J=8 Hz, 1H, Ar), 10.47 (s, 1H, NH); $^{13}$C NMR ($CDCl_3$) δ8.35, 14.76, 16.19, 32.26, 40.24, 40.65, 46.05, 51.12, 55.98, 64.63, 111.50, 112.83, 116.86, 116.94, 117.84, 119.64, 130.31, 133.43, 138.02, 141.44, 148.72, 149.41, 170.07, 172.72; Anal Calcd for $C_{25}H_{31}N_3O_6S+0.35H_2O$: C, 59.12; H, 6.29; N, 8.27, $H_2O$ 1.26. Found: C, 59.42; H, 6.16; N, 8.05, $H_2O$ 1.24.

5.5. Example 5

(1R)-Cyclopropanecarboxylic acid {2-[3-amino-1-(3-ethoxy-4-methoxy-phenyl)-propyl]-3-oxo-2,3-dihydro-1H-isoindol-4-yl}-amide

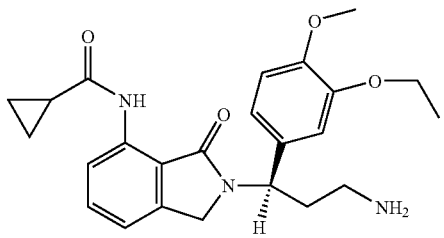

To a solution of triphenyl phosphine (1.4 g, 5.2 mmol), (1R)-cyclopropanecarboxylic acid {2-[1-(3-ethoxy-4-methoxy-phenyl)-3-hydroxy-propyl]-3-oxo-2,3-dihydro-1H-isoindol-4-yl}-amide (1.5 g, 3.4 mmol) and tert-butyl [(tert-butoxy)carbonylamino]formate (2.3 g, 10 mmol) in THF (15 mL) was added a solution of DIAD (1 mL, 5.1 mmol) in THF (10 mL) at room temperature. After 1.5 hrs, the residue was purified with chromatography (Silica Gel) to give (3R)-tert-butyl (N-{(3R)-3-[7-(cyclopropylcarbonylamino)-1-oxoisoindolin-2-yl]-3-(3-ethoxy-4-methoxyphenyl)propyl}(tert-butoxy)carbonylamino)formate as an oil (2.4 g). The oil in trifluoroacetic acid (5 mL) and methylene chloride (5 mL) was stirred at room temperature for 1 hr. The solvent was removed in vacuo to give an oil. The oil was stirred in ether (10 mL) to give a suspension. The suspension was filtered to give (1R)-cyclopropanecarboxylic acid {2-[3-amino-1-(3-ethoxy-4-methoxy-phenyl)-propyl]-3-oxo-2,3-dihydro-1H-isoindol-4-yl}-amide $CF_3COOH$ salt as a white solid (1.1 g, 57% yield). mp, 169-171° C.; $^1H$ NMR (DMSO-$d_6$) δ 0.89-0.94 (m, 4H, 2CH$_2$), 1.31 (t, J=7 Hz, 3H, CH$_3$), 1.72-1.79 (m, 1H, CH), 2.31-2.41 (m, 2H, CH$_2$), 2.80-2.82 (m, 2H, CH$_2$), 3.74 (s, 3H, CH$_3$), 3.99-4.09 (m, 3H, CH$_2$, NCHH), 4.53 (d, J=18 Hz, 1H, NCHH), 5.35 (dd, J=6, 9 Hz, 1H, NCH), 6.91-6.99 (m, 3H, Ar), 7.19 (d, J=8 Hz, 1H, Ar) 7.51 (t, J=8 Hz, 1H, Ar), 7.80 (br. s, 3H, NH$_3$), 8.23 (d, J=8 Hz, 1H, Ar), 10.54 (s, 1H, NH); $^{13}C$ NMR (DMSO-$d_6$) δ7.78, 14.70, 15.48, 29.20, 36.69, 45.99, 51.58, 55.49, 63.84, 112.01, 112.35, 116.91, 117.19, 117.59, 119.59, 130.87, 132.89, 136.98, 142.32, 148.05, 148.74, 168.55, 171.69; Anal Calcd for $C_{24}H_{29}N_3O_4$+1.2 $CF_3COOH$: C, 56.59; H, 5.43; N, 7.50. Found: C, 56.65; H, 5.39; N, 7.26.

5.6. Example 6

(1R)-Cyclopropanecarboxylic acid {2-[1-(3-ethoxy-4-methoxy-phenyl)-3-ureido-propyl]-3-oxo-2,3-dihydro-1H-isoindol-4-yl}-amide

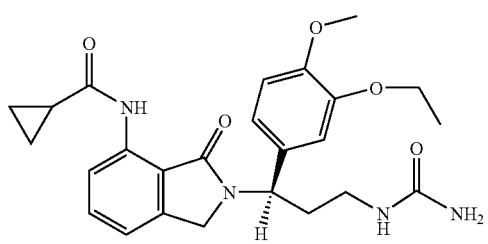

To a solution of (1R)-cyclopropanecarboxylic acid {2-[3-amino-1-(3-ethoxy-4-methoxy-phenyl)-propyl]-3-oxo-2,3-dihydro-1H-isoindol-4-yl}-amide $CF_3COOH$ salt (0.40 g, 0.74 mmol) in HCl (10 mL, 0.5 M) was added a solution of potassium cyanate (240 mg, 3 mmol) in water (3 mL). The suspension was heated at 50° C. overnight. The mixture was extracted with ethyl acetate (50 mL) and water (20 mL). The organic layer was washed with HCl (1N, 50 mL), brine (50 mL), and dried over MgSO$_4$. The solvent was removed in vacuo to give a solid, which was purified with prep HPLC to give (1R)-Cyclopropanecarboxylic acid {2-[1-(3-ethoxy-4-methoxy-phenyl)-3-ureido-propyl]-3-oxo-2,3-dihydro-1H-isoindol-4-yl}-amide as a white solid (220 mg, 65% yield): mp, 162-164° C.; $^1H$ NMR (DMSO-$d_6$) δ 0.88 (d, J=6 Hz, 4H, 2CH$_2$), 1.31 (t, J=7 Hz, 3H, CH$_3$), 1.72-1.79 (m, 1H, CH), 2.11-2.23 (m, 2H, CH$_2$), 2.90-2.99 (m, 2H, CH$_2$), 3.73 (s, 3H, CH$_3$), 3.93-4.13 (m, 3H, NCHH, CH$_2$), 4.57 (d, J=17 Hz, 1H, NCHH), 5.28 (t, J=9 Hz, 1H, NH), 5.48 (s, 2H, NH$_2$), 6.01 (t, J=5 Hz, 1H, NCH), 6.88-6.94 (m, 3H, Ar), 7.17 (d, J=8 Hz, 1H, Ar), 7.48 (t, J=8 Hz, 1H, Ar), 8.22 (d, J=8 Hz, 1H, Ar), 10.59 (s, 1H, NH); $^{13}C$ NMR (DMSO-$d_6$) δ7.75, 14.72, 15.48, 31.97, 36.81, 45.89, 51.74, 55.45, 63.78, 111.97, 112.34, 116.79, 117.33, 117.52, 119.67, 131.93, 132.68, 136.95, 142.29, 147.96, 148.46, 159.69, 168.27, 171.68; Anal Calcd for $C_{25}H_{30}N_4O_5$+0.6$H_2O$: C, 62.91; H, 6.59; N, 11.74, $H_2O$ 2.26. Found: C, 62.60; H, 6.32; N, 11.56, $H_2O$ 1.20.

5.7. Example 7

(1R)-Cyclopropanecarboxylic acid {2-[3-dimethylamino-1-(3-ethoxy-4-methoxy-phenyl)-propyl]-3-oxo-2,3-dihydro-1H-isoindol-4-yl}-amide hydrochloride

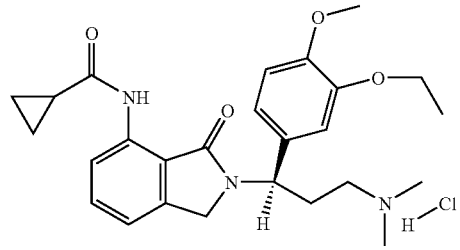

A mixture of (1R)-cyclopropanecarboxylic acid {2-[3-amino-1-(3-ethoxy-4-methoxy-phenyl)-propyl]-3-oxo-2,3-dihydro-1H-isoindol-4-yl}-amide $CF_3COOH$ salt (0.56 g, 1.0 mmol), Pd/C (150 mg) and formaldehyde (400 mg, 5 mmol) in methanol (40 mL) was shaken under hydrogen (50 psi) overnight. The suspension was filtered thru a pad of Celite. The solvent was removed in vacuo. The residue was extracted with methylene chloride (50 mL) and sodium hydrogen carbonate (sat, 50 mL). The organic layer was washed with brine (50 mL), and dried over MgSO$_4$. The solvent was removed in vacuo to give a solid, which was purified with prep HPLC to give (1R)-cyclopropanecarboxylic acid {2-[3-dimethylamino-1-(3-ethoxy-4-methoxy-phenyl)-propyl]-3-oxo-2,3-dihydro-1H-isoindol-4-yl}-amide hydrochloride as a white solid (220 mg, 44% yield): mp, 119-121° C.; $^1H$ NMR (DMSO-$d_6$) δ 0.88 (d, J=6 Hz, 4H, 2CH$_2$), 1.32 (t, J=7 Hz, 3H, CH$_3$), 1.73-1.79 (m, 1H, CH), 2.42-2.59 (m, 2H, CH$_2$), 2.76 (s, 3H, CH$_3$), 2.78 (s, 3H, CH$_3$), 3.02-3.10 (m, 2H, CH$_2$), 3.74 (s, 3H, CH$_3$), 3.99-4.06 (m, 3H, NCHH, CH$_2$), 4.59 (d, J=17 Hz, 1H, NCHH), 5.32 (dd, J=5, 10 Hz, 1H, NH), 6.96 (brs, 3H, Ar), 7.19 (d, J=8 Hz, 1H, Ar), 7.51 (t, J=8 Hz, 1H, Ar), 8.23 (d, J=8 Hz, 1H, Ar), 10.46 (brs, 1H, HCl) 10.54 (s, 1H, NH); $^{13}$C NMR (DMSO-d$_6$) δ7.79, 14.71, 15.47, 25.86, 42.00, 42.05, 45.72, 51.54, 54.07, 55.49, 63.89, 111.96, 122.29, 116.88, 117.22, 117.61, 119.75, 130.64, 132.85, 136.99, 142.37, 148.07, 148.75, 168.42, 171.72; Anal Calcd for $C_{26}H_{34}N_3O_4Cl+1\ H_2O$: C, 61.71; H, 7.17; N, 8.30, Cl, 7.01, $H_2O$ 3.56. Found: C, 61.85; H, 7.26; N, 7.99, Cl, 7.51, $H_2O$ 3.36.

5.8. Example 8

(1R)-Cyclopropanecarboxylic acid {2-[1-(3-ethoxy-4-methoxy-phenyl)-3-methanesulfonyl-propyl]-3-oxo-2,3-dihydro-1H-isoindol-4-yl}-amide

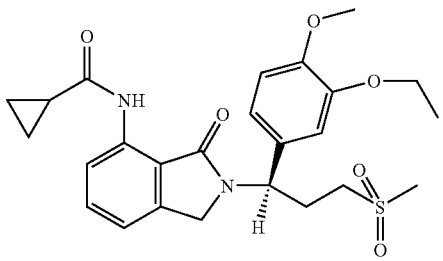

To a solution of triphenyl phosphine (0.63 g, 2.4 mmol) in THF (10 mL) was added DIAD (0.47 mL, 2.4 mmol) at 0° C. After 10 min, (1R)-cyclopropanecarboxylic acid {2-[1-(3-ethoxy-4-methoxy-phenyl)-3-hydroxy-propyl]-3-oxo-2,3-dihydro-1H-isoindol-4-yl}-amide (0.93 mL, 2.2 mmol) was added as solid. After 5 min, sodium thiomethoxide (180 mg, 2.6 mmol) was added. After 20 min, the cold bath was removed and the mixture was stirred at room temperature for 1.5 hrs. To the mixture was added water (15 mL), methanol (15 mL), and oxone (5.4 g, 8.8 mmol) and kept for 16 h. The mixture was extracted with methylene chloride (100 mL) and water (50 mL). The organic layer was dried over MgSO$_4$. The solvent was removed in vacuo to give a solid. The solid was purified with prep HPLC to give (1R)-cyclopropanecarboxylic acid {2-[1-(3-ethoxy-4-methoxy-phenyl)-3-methanesulfonyl-propyl]-3-oxo-2,3-dihydro-1H-isoindol-4-yl}-amide as a white solid (50 mg, 5% yield): mp, 148-150° C.; $^1$H NMR (CDCl$_3$) δ 0.89-0.94 (m, 2H, CH$_2$), 1.10-1.13 (m, 2H, CH$_2$), 1.46 (t, J=7 Hz, 3H, CH$_3$), 1.65-1.73 (m, 1H, CH), 2.60-2.69 (m, 2H, CH$_2$), 2.96 (s, 3H, CH$_3$), 3.02-3.22 (m, 2H, CH$_2$), 3.87 (s, 3H, CH$_3$), 3.99 (d, J=17 Hz, 1H, NCHH), 4.07 (q, J=7 Hz, 2H, CH$_2$), 4.30 (d, J=17 Hz, 1H, NCHH), 5.48 (t, J=8 Hz, 1H, NCH), 6.84-7.02 (m, 4H, Ar), 7.46 (t, J=8 Hz, 1H, Ar), 8.45 (d, J=8 Hz, 1H, Ar), 10.49 (s, 1H, NH); $^{13}$C NMR (CDCl$_3$) δ8.30, 14.75, 16.19, 23.78, 41.24, 45.95, 51.99, 53.01, 56.00, 64.65, 111.60, 112.37, 116.88, 117.00, 117.89, 119.46, 129.82, 133.52, 138.09, 141.29, 148.87, 149.55, 169.79, 172.66; Anal Calcd for $C_{25}H_{30}N_2O_6S_1$: C, 61.71; H, 6.21; N, 5.76. Found: C, 61.33; H, 6.19; N, 5.59.

5.9. Example 9

(1R)-Cyclopropanecarboxylic acid {2-[1-(3-ethoxy-4-methoxy-phenyl)-2-hydroxycarbamoyl-ethyl]-3-oxo-2,3-dihydro-1H-isoindol-4-yl}-amide

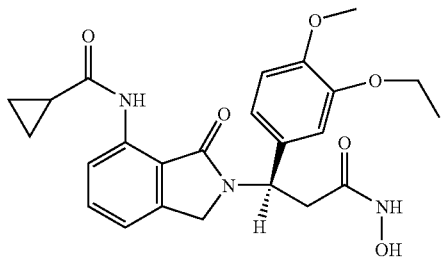

A solution of (1R)-3-[7-(cyclopropanecarbonyl-amino)-1-oxo-1,3-dihydro-isoindol-2-yl]-3-(3-ethoxy-4-methoxy-phenyl)-propionic acid (300 mg, 0.68 mmol) and CDI (130 mg, 0.81 mmol) in THF (3 mL) was stirred at room temperature for 2 hrs. To the mixture was added hydroxylamine HCl (69 mg, 1 mmol) and kept for overnight. Water (20 mL) was added to the mixture. The suspension was filtered to give (1R)-Cyclopropanecarboxylic acid {2-[1-(3-ethoxy-4-methoxy-phenyl)-2-hydroxycarbamoyl-ethyl]-3-oxo-2,3-dihydro-1H-isoindol-4-yl}-amide as a white solid (220 mg, 71% yield): mp, 160-162° C.; $^1$H NMR (DMSO-d$_6$) δ 0.88-0.92 (m, 4H, 2CH$_2$), 1.31 (t, J=7 Hz, 3H, CH$_3$), 1.72-1.81 (m, 1H, CH), 2.85 (d, J=8 Hz, 2H, CH$_2$), 3.73 (s, 3H, CH$_3$), 4.01 (q, J=7 Hz, 2H, CH$_2$), 4.16 (d, J=18 Hz, 1H, NCHH), 4.57 (d, J=18 Hz, 1H, NCHH), 5.68 (t, J=8 Hz, 1H, NCH), 6.86-6.95 (m, 3H, Ar), 7.19 (d, J=8 Hz, 1H, Ar) 7.49 (t, J=8 Hz, 1H, Ar), 8.22 (d, J=8 Hz, 1H, Ar), 8.83 (s, 1H, OH), 10.56 (s, 1H, NH), 10.58 (s, 1H, NH); $^{13}$C NMR (DMSO-d$_6$) δ7.77, 14.72, 15.47, 35.03, 46.44, 51.33, 55.48, 63.81, 111.93, 112.16, 116.81, 117.38, 117.51, 119.37, 131.45, 132.74, 136.96, 142.21, 147.94, 148.55, 165.93, 167.97, 171.11; Anal Calcd for $C_{24}H_{27}N_3O_6$: C, 63.57; H, 6.00; N, 9.27. Found: C, 63.24; H, 5.69; N, 8.91.

5.10. Example 10

(1R)-Cyclopropanecarboxylic acid {2-[2-acetoxycarbamoyl-1-(3-ethoxy-4-methoxy-phenyl)-ethyl]-3-oxo-2,3-dihydro-1H-isoindol-4-yl}-amide

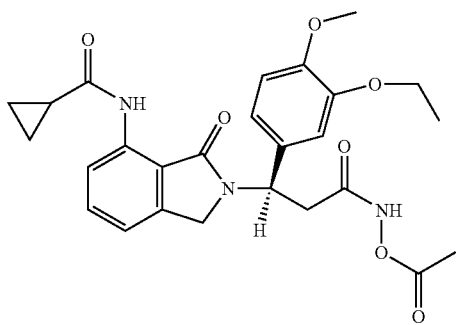

A solution of (1R)-cyclopropanecarboxylic acid {2-[1-(3-ethoxy-4-methoxy-phenyl)-2-hydroxycarbamoyl-ethyl]-3-oxo-2,3-dihydro-1H-isoindol-4-yl}-amide and acetic anhydride (0.09 mL, 1 mmol) in acetonitrile/methylene chloride (6 mL each) was stirred at room temperature for 21 hrs. Ether (10 mL) and hexane (10 mL) was added to give a suspension. The suspension was filtered to give (1R)-cyclopropanecarboxylic acid {2-[2-acetoxycarbamoyl-1-(3-ethoxy-4-methoxy-phenyl)-ethyl]-3-oxo-2,3-dihydro-1H-isoindol-4-yl}-amide as a white solid (270 mg, 63% yield): mp, 140-142° C.; $^1$H NMR (DMSO-$d_6$) δ 0.88-0.92 (m, 4H, 2CH$_2$), 1.30 (t, J=7 Hz, 3H, CH$_3$), 1.75-1.81 (m, 1H, CH), 2.09 (s, 3H, CH$_3$), 3.02-3.07 (m, 2H, CH$_2$), 3.73 (s, 3H, CH$_3$), 4.01 (q, J=7 Hz, 2H, CH$_2$), 4.18 (d, J=18 Hz, 1H, NCHH), 4.60 (d, J=18 Hz, 1H, NCHH), 5.67 (t, J=8 Hz, 1H, NCH), 6.86-6.95 (m, 3H, Ar), 7.18 (d, J=8 Hz, 1H, Ar) 7.49 (t, J=8 Hz, 1H, Ar), 8.23 (d, J=8 Hz, 1H, Ar), 10.54 (s, 1H, NH), 11.86 (s, 1H, NH); $^{13}$C NMR (DMSO-$d_6$) δ7.79, 14.70, 15.46, 17.95, 17.95, 34.55, 46.53, 51.06, 55.44, 63.76, 111.87, 111.99, 116.77, 117.29, 117.47, 119.23, 131.17, 132.74, 136.94, 142.25, 147.92, 148.52, 166.48, 168.02, 168.32, 171.70; Anal Calcd for $C_{26}H_{29}N_3O_7+0.1H_2O$: C, 62.79; H, 5.92; N, 8.45, $H_2O$, 0.36. Found: C, 62.44; H, 5.82; N, 8.37, $H_2O$, 0.30.

5.11. Example 11

(3R)-Cyclopropanecarboxylic acid {2-[1-(3-ethoxy-4-methoxy-phenyl)-3-methanesulfinyl-propyl]-3-oxo-2,3-dihydro-1H-isoindol-4-yl}-amide

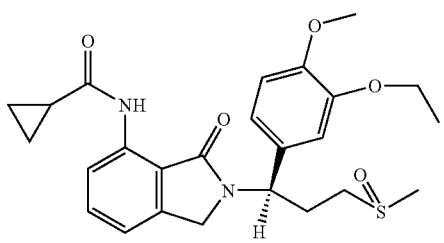

To a solution of (1R)-cyclopropanecarboxylic acid {2-[1-(3-ethoxy-4-methoxy-phenyl)-3-hydroxy-propyl]-3-oxo-2,3-dihydro-1H-isoindol-4-yl}-amide (5.7 g, 13 mmol), triphenyl phosphine (7.1 g, 2.4 mmol) and thioacetic acid (2.2 mL, 31 mmol) in THF (50 mL) was added a solution of DIAD (5.5 mL, 28 mmol) in THF (50 mL) at room temperature. After 4 hrs, methanol (5 mL) was added to the solution. The solvent was removed in vacuo. The residue was purified with Chromatography to give (3R)-thioacetic acid S-[3-[7-(cyclopropanecarbonyl-amino)-1-oxo-1,3-dihydro-isoindol-2-yl]-3-(3-ethoxy-4-methoxy-phenyl)-propyl]ester (5.1 g, 79% yield). To a solution of (3R)-thioacetic acid S-[3-[7-(cyclopropanecarbonyl-amino)-1-oxo-1,3-dihydro-isoindol-2-yl]-3-(3-ethoxy-4-methoxy-phenyl)-propyl]ester (5.0 g, 10 mmol) and methyl iodide (0.8 mL, 13 mmol) in methanol (40 mL) was added a solution of sodium hydroxide (5N, 4.2 mL, 21 mmol) at room temperature. After 2 hrs, to the mixture was added water (40 mL), methylene chloride (20 mL), and oxone (18 g, 29 mmol) and kept for 1.5 hrs. The mixture was extracted with methylene chloride (100 mL) and water (50 mL). The organic layer was washed with $Na_2S_2O_3$ (10% 50 mL), brine (50 mL) and dried over MgSO$_4$. The solvent was removed in vacuo. The residue was purified with chromatography (Silica Gel) to give (3R)-cyclopropanecarboxylic acid {2-[1-(3-ethoxy-4-methoxy-phenyl)-3-methanesulfinyl-propyl]-3-oxo-2,3-dihydro-1H-isoindol-4-yl}-amide as a white solid (320 mg, 6% yield): mp, 122-125° C.; $^1$H NMR (CDCl$_3$) δ 0.86-0.93 (m, 2H, CH$_2$), 1.08-1.14 (m, 2H, CH$_2$), 1.45 (t, J=7 Hz, 3H, CH$_3$), 1.63-1.72 (m, 1H, CH), 2.58 and 2.59 (2s, 3H, CH$_3$), 2.60-2.82 (m, 4H, CH$_2$CH$_2$), 3.86 (s, 3H, CH$_3$), 3.97 (d, J=17 Hz, 1H, NCHH), 4.06 (q, J=7 Hz, 2H, CH$_2$), 4.31 and 4.35 (2 sets of d, J=17 Hz, 1H, NCHH), 5.50-5.59 (m, 1H, NCH), 6.84-7.02 (m, 4H, Ar), 7.41-7.48 (m, 1H, Ar), 8.43 (d, J=8 Hz, 1H, Ar), 10.54 (s, 1H, NH); $^{13}$C NMR (CDCl$_3$) δ8.28, 14.76, 16.18, 24.28, 24.76, 38.95, 45.71, 45.89, 51.22, 51.42, 53.07, 53.63, 55.99, 64.64, 111.54, 112.49, 116.89, 117.19, 117.80, 119.54, 130.38, 130.48, 133.37, 138.04, 141.36, 148.77, 149.40, 169.79, 169.82, 172.66; Anal Calcd for $C_{25}H_{30}N_2O_5S+0.8H_2O$: C, 61.93; H, 6.57; N, 5.78; $H_2O$, 2.97. Found: C, 61.63; H, 6.62; N, 5.61; $H_2O$, 2.19.

5.12. Example 12

(3R)-3-[4-Chloro-7-(cyclopropanecarbonyl-amino)-1-oxo-1,3-dihydro-isoindol-2-yl]-3-(3-ethoxy-4-methoxy-phenyl)-propionic acid

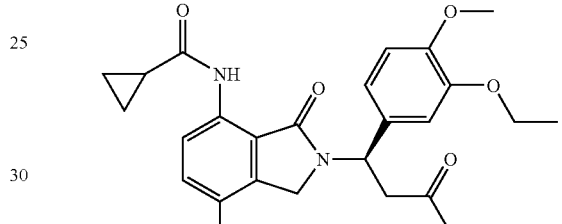

To a solution of (3R)-3-[4-chloro-7-(cyclopropanecarbonyl-amino)-1-oxo-1,3-dihydro-isoindol-2-yl]-3-(3-ethoxy-4-methoxy-phenyl)-propionic acid methyl ester (3.0 g, 6.2 mmol) in THF (60 ml) was added NaOH (10 N, 1.2 ml, 12 mmol). The mixture was stirred at room temperature overnight. To it was added water (50 ml). The mixture was extracted with EtOAc (50 ml×2). The aqueous layer was acidified by conc. HCl until pH=6. The resulted cloudy mixture was extracted with EtOAc (50 ml×2). The organice layer was washed with water (30 ml×2), brine (30 ml), dried over $Na_2SO_4$, filtered and concentrated in vacuo to give (3R)-3-[4-chloro-7-(cyclopropanecarbonyl-amino)-1-oxo-1,3-dihydro-isoindol-2-yl]-3-(3-ethoxy-4-methoxy-phenyl)-propionic acid as a white solid (2.8 g, 99%): mp, 118-120° C.; $^1$H NMR (CDCl$_3$) δ 0.86-0.91 (m, 2H, c-CH$_2$), 1.05-1.11 (m, 2H, c-CH$_2$), 1.45 (t, J=7.0 Hz, 3H, OCH$_2$CH$_3$), 1.65-1.70 (m, 1H, c-CH), 3.13 (dd, J=6, 15 Hz, 1H, CHH), 3.23 (dd, J=10, 15 Hz, 1H, CHH), 3.86 (s, 3H, OCH$_3$), 4.00-4.11 (m, 3H, NCHH+OCH$_2$CH$_3$), 4.32 (d, J=18 Hz, 1H, NCHJH), 5.80-5.86 (m, 1H, CHN), 6.83-6.92 (m, 3H, Ar), 7.35 (d, J=9 Hz, 1H, Ar), 8.41 (d, J=9 Hz, 1H, Ar), 10.39 (s, 1H, NHCO). $^{13}$CNMR (CDCl$_3$): δ8.4, 8.5, 14.7, 16.1, 36.7, 45.9, 51.8, 55.9, 64.6, 111.5, 112.4, 118.9, 119.0, 1198, 121.9, 130.1, 132.9, 136.7, 139.0, 148.7, 149.5, 168.7, 172.8, 173.8; Anal Calcd for $C_{24}H_{25}ClN_2O_6+0.37H_2O$: C, 60.11; H, 5.41; N, 5.84. Found: C, 60.11; H, 5.25; N, 5.64, $H_2O$, 1.40.

5.13. Example 13

(3R)-3-[4-Chloro-7-(cyclopropanecarbonyl-amino)-1-oxo-1,3-dihydro-isoindol-2-yl]-3-(3-ethoxy-4-methoxy-phenyl)-propionic acid methyl ester

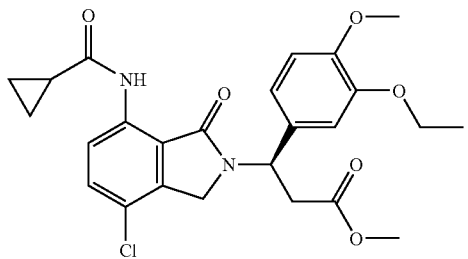

To a solution of (3R)-3-amino-3-(3-ethoxy-4-methoxy-phenyl)-propionic acid methyl ester (3.0 g, 8.7 mmol) in DMF (25 ml) was added 2-bromomethyl-3-chloro-6-(cyclopropanecarbonyl-amino)-benzoic acid methyl (2.2 g, 8.6 mmol) and triethyl amine (2.4 ml, 17 mmol). The mixture was heated at 90° C. overnight. The solvent was removed in vacuo. The resulted oil was extracted with ethyl acetate (50 ml) and water (30 ml). The organic layer was washed with water (30 ml×2), brine (30 ml) and dried over magnesium sulfate. The solvent was removed in vacuo and the resulted oil was purified by silica gel column to give (3R)-3-[4-chloro-7-(cyclopropanecarbonyl-amino)-1-oxo-1,3-dihydro-isoindol-2-yl]-3-(3-ethoxy-4-methoxy-phenyl)-propionic acid methyl ester as a white solid (3.5 mg, 83%): mp, 158-160° C.; $^1$H NMR (CDCl$_3$) δ 0.86-0.93 (m, 2H, c-CH$_2$), 1.07-1.13 (m, 2H, c-CH$_2$), 1.46 (t, J=7.0 Hz, 3H, OCH$_2$CH$_3$), 1.64-1.71 (m, 1H, c-CH), 3.10 (dd, J=6, 15 Hz, 1H, CHH), 3.24 (dd, J=10, 15 Hz, 1H, CHN), 3.67 (s, 3H, COOCH$_3$), 3.86 (s, 3H, OCH$_3$), 4.03 (d, J=18 Hz, 1H, NCHH), 4.10 (t, J=7.0 Hz, 2H, OCH$_2$CH$_3$), 4.31 (d, J=18 Hz, 1H, NCHH), 5.82-5.88 (m, 1H, CHN), 6.84-6.93 (m, 3H, Ar), 7.37 (d, J=8 Hz, 1H, Ar), 8.44 (d, J=8 Hz, 1H, Ar), 10.47 (s, 1H, NHCO). $^{13}$CNMR (CDCl$_3$): δ8.4, 14.7, 16.1, 36.7, 45.9, 51.8, 52.1, 55.9, 64.6, 111.5, 118.9, 119.0, 119.6, 121.8, 130.2, 132.8, 136.7, 139.0, 148.7, 149.3, 168.5, 170.6, 172.7, 184.3; Anal Calcd for C$_{25}$H$_{27}$ClN$_2$O$_6$: C, 61.66; H, 5.59; N, 5.75. Found: C, 61.32; H, 5.49; N, 5.70.

5.14. Example 14

(1R)-Cyclopropanecarboxylic acid {2-[2-carbamoyl-1-(3-ethoxy-4-methoxy-phenyl)-ethyl]-7-chloro-3-oxo-2,3-dihydro-1H-isoindol-4-yl}-amide

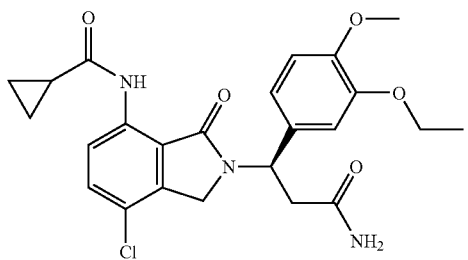

To a solution of (3R)-3-[4-chloro-7-(cyclopropanecarbonyl-amino)-1-oxo-1,3-dihydro-isoindol-2-yl]-3-(3-ethoxy-4-methoxy-phenyl)-propionic acid (0.62 g, 1.3 mmol) in THF (5 ml) was added carbonyldiimidazole (0.3 g, 2 mmol) at room temperature. The solution was stirred for 2 hrs at room temperature. To the mixture was added NH$_4$OH (13.8 N, 0.3 ml, 3.9 mmol). The resulting mixture was stirred at room temperature for 4 hrs. Water (20 ml) was added to the reaction mixture. THF was removed in vacuo and to the resulting mixture was added ethyl acetate (30 ml). The mixture was washed with saturated sodium bicarbonate solution (3×20 ml), water (20 ml) and brine (20 ml). The organic layer was dried over magnesium sulfate, filtered and concentrated in vacuo. The resulting oil was stirred with ether (5 ml) for 2 hrs and filtered to give (1R)-cyclopropanecarboxylic acid {2-[2-carbamoyl-1-(3-ethoxy-4-methoxy-phenyl)-ethyl]-7-chloro-3-oxo-2,3-dihydro-1H-isoindol-4-yl}-amide as white solid (0.5 g, 82%): mp 201-203° C.; $^1$HNMR (CDCl$_3$): δ 0.88-0.91 (m, 2H, c-CH$_2$), 1.08-1.11 (m, 2H, c-CH$_2$), 1.45 (t, J=7.5 Hz, 3H, OCH$_2$CH$_3$), 1.65-1.68 (m, 1H, c-CH), 2.98 (dd, J=5, 16 Hz, 1H, CHH), 3.36 (dd, J=5, 16 Hz, 1H, CHH), 3.86 (s, 3H, OCH$_3$), 4.08 (q, J=7.5 Hz, 2H, OCH$_2$CH$_3$), 4.13 (d, J=17 Hz, 1H, NCHH), 4.35 (d, J=17 Hz, 1H, NCHH), 5.42 (broad s, 1H), 5.58-5.64 (m, 1H, CHN), 6.00 (broad s, 1H), 6.83-6.95 (m, 3H, Ar), 7.36 (d, J=9 Hz, 1H, Ar), 8.43 (d, J=9 Hz, 1H, Ar), 10.41 (s, 1H); $^{13}$C NMR (CDCl$_3$): 8.4, 14.7, 16.1, 38.6, 48.6, 46.7, 53.2, 53.4, 56.0, 64.5, 65.8, 112.2, 119.0, 119.1, 119.5, 121.8, 130.6, 132.8, 136.6, 139.1, 148.7, 149.4, 169.0, 171.8, 172.6; Anal. Calcd. for C$_{24}$H$_{26}$ClN$_3$O$_5$: C, 61.08; H, 5.55; N, 8.90. Found: C, 60.89; H, 5.42; N, 8.51.

5.15. Example 15

(1R)-Cyclopropanecarboxylic acid {7-chloro-2-[2-dimethylcarbamoyl-1-(3-ethoxy-4-methoxy-phenyl)-ethyl]-3-oxo-2,3-dihydro-1H-isoindol-4-yl}-amide

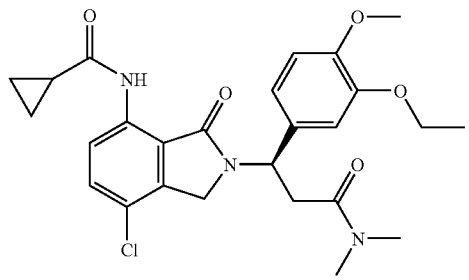

To a solution of (3R)-3-[4-chloro-7-(cyclopropanecarbonyl-amino)-1-oxo-1,3-dihydro-isoindol-2-yl]-3-(3-ethoxy-4-methoxy-phenyl)-propionic acid (0.62 g, 1.3 mmol) in tetrahydrofurane (5 ml) was added carbonyldiimidazole (0.3 g, 2 mmol) at room temperature. The solution was stirred for 2 hours at room temperature. To the mixture was added THF solution of dimethylamine (2 M, 1.3 ml, 2.6 mmol). The resulted mixture was stirred at room temperature for 4 hrs. Water (20 ml) was added to the reaction mixture. THF was removed in vacuo and to the resulted mixture was added ethyl acetate (30 ml). The mixture was washed with saturated sodium bicarbonate solution (3×20 ml), water (20 ml) and brine (20 ml). The organic layer was dried over magnesium sulfate, filtered and concentrated in vacuo. The resulted oil was stirred with ether (5 ml) for 2 hrs and filtered to give (1R)-cyclopropanecarboxylic acid {7-chloro-2-[2-dimethylcarbamoyl-1-(3-ethoxy-4-methoxy-phenyl)-ethyl]-3-oxo-2,3-dihydro-1H-isoindol-4-yl}-amide as white solid (0.5 g, 77%): mp 163-165° C.; $^1$HNMR (CDCl$_3$): δ 0.86-0.89 (m, 2H, c-CH$_2$), 1.08-1.11 (m, 2H, c-CH$_2$), 1.46 (t, J=7.5 Hz, 3H, OCH$_2$CH$_3$), 1.65-1.68 (m, 1H, c-CH), 2.93 (s, 3H, NCH$_3$), 3.04 (dd, J=5, 16 Hz, 1H, CHH), 3.12 (s, 3H, NCH$_3$), 3.56 (dd, J=5, 16 Hz, 1H, CHH), 3.86 (s, 3H, OCH$_3$), 4.10 (q, J=7.5 Hz, 2H, OCH$_2$CH$_3$), 4.25 (d, J=17 Hz, 1H, NCHH), 4.60 (d, J=17 Hz, 1H, NCHH), 5.58-5.64 (m, 1H, CHN), 6.83-6.97 (m, 3H, Ar), 7.35 (d, J=9 Hz, 1H, Ar), 8.41 (d, J=9 Hz, 1H, Ar), 10.51 (s, 1H, NH); $^{13}$C NMR (CDCl$_3$): 8.9, 15.4, 16.8, 36.2, 36.6, 38.0, 48.6, 54.3, 56.6, 65.2, 112.1, 113.1, 119.8, 120.0, 120.1, 122.3, 132.2, 133.2, 137.3, 139.9, 149.2, 149.8, 169.4, 170.1, 173.2; Anal. Calcd. for C$_{26}$H$_{30}$ClN$_3$O$_5$: C, 62.46; H, 6.05; N, 8.40. Found: C, 62.43; H, 5.42; N, 8.51.

5.16. Example 16

(1R)-Cyclopropanecarboxylic acid {7-chloro-2-[1-(3-ethoxy-4-methoxy-phenyl)-2-hydroxycarbamoyl-ethyl]-3-oxo-2,3-dihydro-1H-isoindol-4-yl}-amide

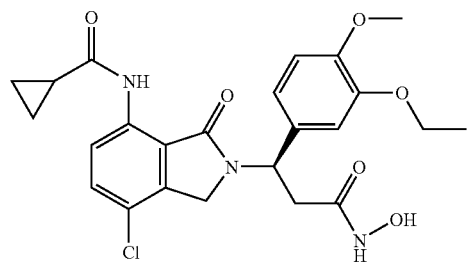

To a solution of (3R)-3-[4-chloro-7-(cyclopropanecarbonyl-amino)-1-oxo-1,3-dihydro-isoindol-2-yl]-3-(3-ethoxy-4-methoxy-phenyl)-propionic acid (1.3 g, 2.8 mmol) in tetrahydrofurane (10 ml) was added carbonyldiimidazole (0.7 g, 4.2 mmol) at room temperature. The solution was stirred for 2 hours at room temperature. To the mixture was added hydroxylamine HCl salt (0.4 g, 5.6 mmol). The resulted mixture was stirred at room temperature for 4 hours. Water (20 ml) was added to the reaction mixture. THF was removed in vacuo and the resulted mixture was added ethyl acetate (30 ml). The mixture was washed with saturated sodium bicarbonate solution (3×20 ml), water (20 ml) and brine (20 ml). The organic layer was dried over magnesium sulfate, filtered and concentrated in vacuo. The resulted oil was stirred with ether (5 ml) for 2 hours and filtered to give (1R)-cyclopropanecarboxylic acid {7-chloro-2-[1-(3-ethoxy-4-methoxy-phenyl)-2-hydroxycarbamoyl-ethyl]-3-oxo-2,3-dihydro-1H-isoindol-4-yl}-amide as white solid (1.2 g, 86%): mp 142-144° C.; $^1$HNMR (DMSO-d$_6$): δ 0.87-0.89 (m, 4H, c-CH$_2$), 1.28-1.33 (t, J=7.5 Hz, 3H, OCH$_2$CH$_3$), 1.78-1.83 (m, 1H, c-CH), 2.85-2.91 (m, 2H, CH$_2$CO), 3.73 (s, 3H), 4.00 (t, J=7.5 Hz, 2H, OCH$_2$CH$_3$), 4.11 (d, J=17 Hz, 1H, NCHH), 4.60 (d, J=17 Hz, 1H, NCHH), 5.53-5.69 (m, 1H, CHN), 6.92-6.94 (m, 3H, Ar), 7.58 (d, J=10 Hz, 1H, Ar), 8.26 (d, J=10 Hz, 1H, Ar), 8.84 (s, 1H), 10.46 (s, 1H), 10.57 (s, 1H); $^{13}$C NMR (DMSO-d$_6$): δ8.4, 8.5, 15.2, 15.9, 35.4, 46.2, 52.2, 55.9, 64.3, 74.6, 112.4, 112.7, 119.7, 119.8, 121.5, 131.7, 132.9, 136.4, 140.2, 148.4, 149.1, 166.3, 167.6, 172.4; Anal. Calcd. for C$_{26}$H$_{28}$ClN$_3$O$_7$+0.5H$_2$O: C, 58.01; H, 5.48; N, 8.46. Found: C, 57.97; H, 5.29; N, 8.53, H$_2$O, 1.5.

5.17. Example 17

(1R)-Cyclopropanecarboxylic acid {2-[2-acetoxycarbamoyl-1-(3-ethoxy-4-methoxy-phenyl)-ethyl]-7-chloro-3-oxo-2,3-dihydro-1H-isoindol-4-yl}-amide

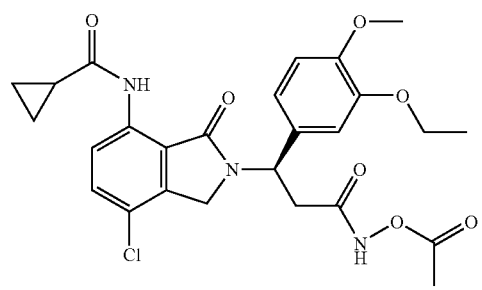

To the solution of cyclopropanecarboxylic acid {7-chloro-2-[1-(3-ethoxy-4-methoxy-phenyl)-2-hydroxycarbamoyl-ethyl]-3-oxo-2,3-dihydro-1H-isoindol-4-yl}-amide (0.45 g, 92 mmol) in CH$_3$CN (50 ml) was added acetic anhydride (0.1 ml, 92 mmol) at room temperature. The mixture was stirred overnight. The solvent was removed in vacuo and the resulted solid was stirred with ether (10 ml) for 2 hrs. The suspension was filtered and the solid was dried in oven to give (1R)-cyclopropanecarboxylic acid {2-[2-acetoxycarbamoyl-1-(3-ethoxy-4-methoxy-phenyl)-ethyl]-7-chloro-3-oxo-2,3-dihydro-1H-isoindol-4-yl}-amide (0.4 g, 80%): mp 139-141° C.; $^1$HNMR (CDCl$_3$): δ 0.85-0.92 (m, 2H, c-CH$_2$), 1.05-1.11 (m, 2H, c-CH$_2$), 1.43 (t, J=7.5 Hz, 3H, OCH$_2$CH$_3$), 1.62-1.68 (m, 1H, c-CH), 2.12 (s, 3H, CH$_3$), 3.02 (dd, J=5, 16 Hz, 1H, CHH), 3.50 (dd, J=5, 16 Hz, 1H, CHH), 3.85 (s, 3H, OCH$_3$), 4.08 (q, J=7.5 Hz, 2H, OCH$_2$CH$_3$), 4.12 (d, J=17 Hz, 1H, CHH), 4.38 (d, J=17 Hz, 1H, CHH), 5.61-5.65 (m, 1H, CHN), 6.81-6.94 (m, 3H, Ar), 7.31 (d, J=10 Hz, 1H, Ar), 8.38 (d, J=10 Hz, 1H, Ar), 10.41 (s, 1H); $^{13}$C NMR (CDCl$_3$): δ9.0, 9.1, 15.3, 16.7, 18.7, 36.8, 48.2, 54.4, 56.5, 65.2, 112.2, 112.8, 119.7, 119.8, 120.2, 122.4, 131.1, 133.5, 137.2, 139.8, 149.3, 150.1, 167.0, 169.0, 170.0, 173.5; Anal. Calcd. for C$_{26}$H$_{28}$ClN$_3$O$_7$: C, 58.92; H, 5.33; N, 7.93. Found: C, 58.58; H, 5.00; N, 7.76.

5.18. Example 18

(1S)-Cyclopropanecarboxylic acid {7-chloro-2-[1-(3-ethoxy-4-methoxy-phenyl)-2-methanesulfonyl-ethyl]-3-oxo-2,3-dihydro-1H-isoindol-4-yl}-amide

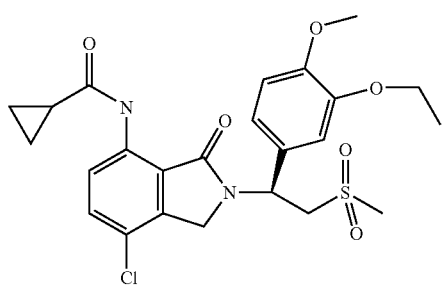

To a solution of (1S)-1-(3-ethoxy-4-methoxy-phenyl)-2-methanesulfonyl-ethylamine (1.4 g, 5.1 mmol) in DMF (20 ml) was added 2-bromomethyl-3-chloro-6-(cyclopropanecarbonyl-amino)-benzoic acid methyl ester (1.6 g, 4.6 mmol) and triethyl amine (2.0 ml, 14 mmol). The mixture was heated at 90° C. overnight. The solvent was removed in vacuo. The resulted oil was extracted with ethyl acetate (50 ml) and water (30 ml). The organic layer was washed with water (30 ml×2), brine (30 ml) and dried over magnesium sulfate. The solvent was removed in vacuo and the resulted oil was purified by silica gel column to give (1S)-cyclopropanecarboxylic acid {7-chloro-2-[1-(3-ethoxy-4-methoxy-phenyl)-2-methanesulfonyl-ethyl]-3-oxo-2,3-dihydro-1H-isoindol-4-yl}-amide as a white solid (650 mg, 30%): mp, 197-199° C.; $^1$H NMR (CDCl$_3$) δ 0.89-0.93 (m, 2H, c-CH$_2$), 1.08-1.12 (m, 2H, c-CH$_2$), 1.44 (t, J=7.0 Hz, 3H, OCH$_2$CH$_3$), 1.65-1.69 (m, 1H, c-CH), 2.97 (s, 3H, CH$_3$SO$_2$), 3.70 (dd, J=5, 15 Hz, 1H, CHH), 3.87 (s, 3H, OCH$_3$), 4.05-4.23 (m, 4H, NCH+CH+OCH$_2$CH$_3$), 4.41 (d, J=17 Hz, 1H, CHH), 5.75-5.81 (m, 1H, CHN), 6.86-6.96 (m, 3H, Ar), 7.39 (d, J=9.0 Hz, 1H, Ar), 8.45 (d, J=9.0 Hz, 1H, Ar), 10.36 (s, 1H, NHCO). $^{13}$CNMR (CDCl$_3$): δ8.5, 14.7, 16.2, 41.6, 46.9, 51.3, 55.5, 56.0, 64.7, 111.7, 112.3, 118.6, 119.3, 119.7, 121.8, 129.1, 133.2, 136.8, 139.0, 149.0, 149.9, 169.2, 172.6; Anal Calcd for C$_{24}$H$_{27}$ClN$_2$O$_6$S: C, 56.86; H, 5.37; N, 5.53. Found: C, 56.81; H, 5.26; N, 5.56.

5.19. Example 19

(1S)-Cyclopropanecarboxylic acid {7-bromo-2-[1-(3-ethoxy-4-methoxy-phenyl)-2-methanesulfonyl-ethyl]-3-oxo-2,3-dihydro-1H-isoindol-4-yl}-amide

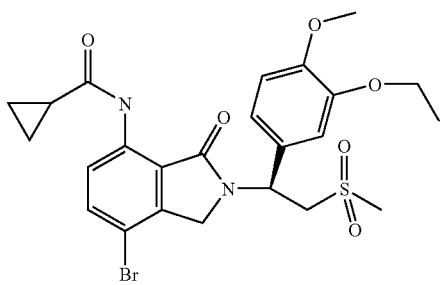

To a solution of (1S)-1-(3-ethoxy-4-methoxy-phenyl)-2-methanesulfonyl-ethylamine (0.35 g, 1.2 mmol) in DMF (10 ml) was added 2-bromomethyl-3-bromo-6-(cyclopropanecarbonyl-amino)-benzoic acid methyl ester (0.45 g, 1.1 mmol) and triethyl amine (0.5 ml, 3.3 mmol). The mixture was heated at 90° C. overnight. The solvent was removed in vacuo. The resulted oil was extracted with ethyl acetate (50 ml) and water (30 ml). The organic layer was washed with water (30 ml×2), brine (30 ml) and dried over magnesium sulfate. The solvent was removed in vacuo and the resulted oil was purified by silica gel column to give (1S)-cyclopropanecarboxylic acid {7-bromo-2-[1-(3-ethoxy-4-methoxy-phenyl)-2-methanesulfonyl-ethyl]-3-oxo-2,3-dihydro-1H-isoindol-4-yl}-amide as a white solid (450 mg, 74%): mp, 219-221° C.; $^1$H NMR (CDCl$_3$) δ 0.89-0.93 (m, 2H, c-CH$_2$), 1.08-1.14 (m, 2H, c-CH$_2$), 1.47 (t, J=7.0 Hz, 3H, OCH$_2$CH$_3$), 1.65-1.70 (m, 1H, c-CH), 2.98 (s, 3H, CH$_3$SO$_2$), 3.70 (dd, J=5, 15 Hz, 1H, CHH), 3.87 (s, 3H, OCH$_3$), 4.06-4.14 (m, 3H, NCHH+OCH$_2$CH$_3$), 4.19 (dd, J=10, 15 Hz, 1H, CHH), 4.55 (d, J=17 Hz, 1H, CH), 5.75-5.81 (m, 1H, CHN), 6.86-6.96 (m, 3H, Ar), 7.53 (d, J=9 Hz, 1H, Ar), 8.40 (d, J=9 Hz, 1H, Ar), 10.38 (s, 1H, NHCO). $^{13}$CNMR (CDCl$_3$): δ9.1, 9.2, 15.4, 16.9, 42.2, 49.1, 52.0, 56.1, 56.7, 65.3, 110.1, 112.3, 112.8, 119.5, 119.9, 120.7, 129.7, 136.8, 138.1, 142.0, 149.6, 150.5, 170.0, 173.3; Anal Calcd for C$_{24}$H$_{27}$BrN$_2$O$_6$S: C, 52.27; H, 4.94; N, 5.08. Found: C, 52.57; H, 4.68; N, 4.95.

5.20. Example 20

Cyclopropanecarboxylic acid {2-[1-(3-ethoxy-4-methoxy-phenyl)-propyl]-3-oxo-2,3-dihydro-1H-isoindol-4-yl}-amide

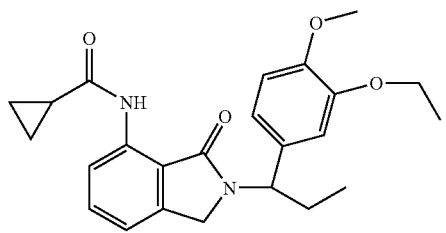

A solution of 7-amino-2-[1-(3-ethoxy-4-methoxy-phenyl)-propyl]-2,3-dihydro-isoindol-1-one (1.0 g, 2.9 mmol) and cyclopropanecarbonyl chloride (0.32 mL, 3.5 mmol) in THF (10 mL) was heated to reflux for 40 min. The solvent was removed in vacuo. The residue was extracted with ethyl acetate (50 mL) and sodium hydrogen carbonate (sat, 50 mL). The organic layer was washed with brine (50 mL) and dried over MgSO$_4$. The solvent was removed in vacuo and the residue was purified with chromatography (Silica Gel) to cyclopropanecarboxylic acid {2-[1-(3-ethoxy-4-methoxy-phenyl)-propyl]-3-oxo-2,3-dihydro-1H-isoindol-4-yl}-amide as a white solid (900 mg, 76% yield): mp, 107-109° C.; $^1$H NMR (CDCl$_3$) δ 0.84-0.92 (m, 2H, CH$_2$), 0.99 (t, J=7 Hz, 3H, CH$_3$), 1.02-1.13 (m, 2H, CH$_2$), 1.44 (t, J=7 Hz, 3H, CH$_3$), 1.64-1.73 (m, 1H, CH), 2.00-2.16 (m, 2H, CH$_2$), 3.86 (s, 3H, CH$_3$), 4.00 (d, J=17 Hz, 1H, CHH), 4.09 (q, J=7 Hz, 2H, CH$_2$), 4.27 (d, J=17 Hz, 1H, NCHH), 5.33 (dd, J=7, 9 Hz, 1H, NCH), 6.83-6.95 (m, 3H, Ar), 7.00 (d, J=8 Hz, 1H, Ar), 7.42 (t, J=8 Hz, 1H, Ar), 8.42 (d, J=8 Hz, 1H, Ar), 10.67 (s, 1H, NH); $^{13}$C NMR (CDCl$_3$) δ 8.19, 11.18, 14.78, 16.18, 24.54, 45.64, 55.53, 55.97, 64.58, 111.46, 112.91, 116.68, 117.67, 119.51, 131.96, 132.94, 138.02, 141.37, 148.54, 149.04, 169.55, 172.70; Anal Calcd for C$_{24}$H$_{28}$N$_2$O$_4$: C, 70.57; H, 6.91; N, 6.86. Found: C, 70.54; H, 6.91; N, 6.86.

5.21. Example 21

Cyclopropanecarboxylic acid {7-chloro-2-[2-cyano-1-(3-ethoxy-4-methoxy-phenyl)-ethyl]-3-oxo-2,3-dihydro-1H-isoindol-4-yl}-amide

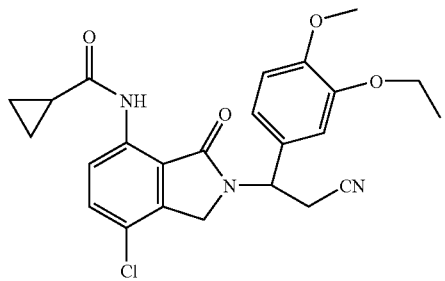

To the DMF solution (20 ml) of 3-Amino-3-(3-ethoxy-4-methoxy-phenyl)-propionitrile (1.55 g, 7 mmol) was added Et$_3$N (1.6 ml, 12 mmol) followed by 2-bromomethyl-3-chloro-6-(cyclopropanecarbonyl-amino)-benzoic acid methyl ester (2.42 g, 7 mmol). The mixture was heated at 90° C. for 12 hrs then cooled to room temperature. The mixture was extracted with EtOAc (50 ml) and water (50 ml). The organic layer was washed with water (50 ml) and brine (50 ml), dried over Na$_2$SO$_4$ and concentrated in vacuo. The resulted oil was purified by silica gel chromatography to give cyclopropanecarboxylic acid {7-chloro-2-[2-cyano-1-(3-ethoxy-4-methoxy-phenyl)-ethyl]-3-oxo-2,3-dihydro-1H-isoindol-4-yl}-amide as white solid (2.4 g, 80%): mp 200-202° C.; $^1$H NMR (CDCl$_3$) δ 0.90-0.94 (m, 2H, c-CH$_2$), 1.09-1.14 (m, 2H, c-CH$_2$), 1.45 (t, J=7.0 Hz, 3H, CH$_3$), 1.64-1.70 (m, 1H, c-CH), 3.12-3.32 (m, 2H, CH$_2$CN), 3.89 (s, 3H), 3.99-4.12 (m, 3H, OCH$_2$CH$_3$+CHHN), 4.37 (d, J=18 Hz, 1H. CHHN), 5.62-5.68 (m, 1H, NCH), 6.87-6.98 (m, 3H, Ar), 7.40 (d, J=9 Hz, 1H, Ar), 8.47 (t, J=9 Hz, 1H, Ar), 10.34 (s, 1H, NH); $^{13}$C NMR (CDCl$_3$) δ 8.5, 14.7, 16.2, 21.2, 46.4, 51.8, 56.0, 64.7, 111.7, 112.2, 116.9, 118.4, 119.1, 119.8, 121.9, 127.9, 133.3, 136.9, 138.9, 149.9, 150.0, 169.0, 172.7; Anal Calcd for C$_{24}$H$_{24}$ClN$_3$O$_4$: C, 63.50; H, 5.33; N, 9.26. Found: C, 63.43; H, 5.31; N, 9.01

5.22. Example 22

Cyclopropanecarboxylic acid {2-[2-(3,5-dichloro-pyridin-4-yl)-1-(3-ethoxy-4-methoxy-phenyl)-ethyl]-3-oxo-2,3-dihydro-1H-isoindol-4-yl}-amide

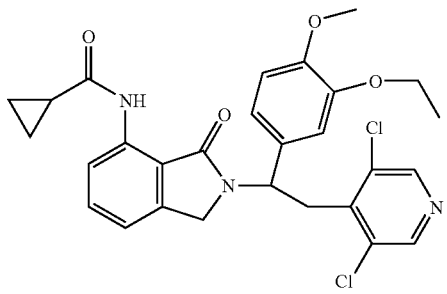

To a mixture of 2-(3,5-dichloro-pyridin-4-yl)-1-(3-ethoxy-4-methoxy-phenyl)-ethanol (500 mg, 1.5 mmol) and PPh$_3$ (0.60 g, 2.3 mmol), was added DIAD (0.44 mL, 2.2 mmol) at 0° C. After 5 min, (PhO)$_2$PON$_3$ was added to the mixture at 0° C. The mixture was allowed to warm to room temperature overnight. To the mixture was added PPh$_3$ (0.9 g, 3.5 mmol) and water (2 mL). The mixture was heated to reflux for 6 hrs. The mixture was extracted with ether (25 mL) and 1N HCl (2×25 mL). The aqueous layer was basified with 10 N sodium hydroxide until pH=14. The aqueous layer was extracted with methylene chloride (2×50 mL). The combined organic layer was concentrated to give an oil. A mixture of the resulted oil, 2-bromomethyl-6-(cyclopropanecarbonyl-amino)-benzoic acid methyl ester (100 mg, 0.64 mmol) and triethyl amine (0.1 mL, 0.7 mmol) in DMF (5 mL) was heated at 80° C. for 27 hrs. The solvent was removed in vacuo. The residue was extracted with ethyl acetate (50 mL) and water (50 mL). The organic layer was washed with water (50 mL) and brine (50 mL). The solvent was removed in vacuo. The residue was purified with Preparative HPLC to give cyclopropanecarboxylic acid {2-[2-(3,5-dichloro-pyridin-4-yl)-1-(3-ethoxy-4-methoxy-phenyl)-ethyl]-3-oxo-2,3-dihydro-1H-isoindol-4-yl}-amide (130 mg, 16% yield): mp, 159-161° C.; $^1$H NMR (CDCl$_3$) δ 0.81-0.91 (m, 2H, CH$_2$), 1.01-1.09 (m, 2H, CH$_2$), 1.45 (t, J=7 Hz, 3H, CH$_3$), 1.56-1.63 (m, 1H, CH), 3.68 (dd, J=4, 13 Hz 1H, CHH), 3.79 (dd, J=11, 13 Hz, 1H, CH—H), 3.89 (s, 3H, CH$_3$), 3.91 (d, J=17 Hz, 1H, NCHH), 4.08 (q, J=7 Hz, 2H, CH$_2$), 4.56 (d, J=17 Hz, 1H, NCHH), 5.94 (dd, J=4, 11 Hz, 1H, NCH), 6.86 (m, 4H, Ar), 7.41 (t, J=8 Hz, 1H, Ar), 8.40 (d, J=8 Hz, 1H, Ar), 8.43 (s, 2H, pyr), 10.28 (s, 1H, NH); $^{13}$C NMR (CDCl$_3$) δ 8.27, 14.76, 16.09, 33.22, 46.71, 52.63, 56.00, 64.66, 111.44, 112.69, 116.62, 116.95, 117.67, 119.52, 130.65, 133.11, 133.19, 137.96, 141.40, 142.89, 147.59, 148.75, 149.52, 169.32, 172.75; Anal Calcd for C$_{28}$H$_{27}$N$_3$O$_4$Cl$_2$: C, 62.23; H, 5.04; N, 7.78. Found: C, 61.99; H, 5.09; N, 7.43.

5.23. Example 23

(1R)-Cyclopropanecarboxylic acid {2-[1-(3-ethoxy-4-methoxy-phenyl)-3-hydroxy-3-methyl-butyl]-3-oxo-2,3-dihydro-1H-isoindol-4-yl}-amide

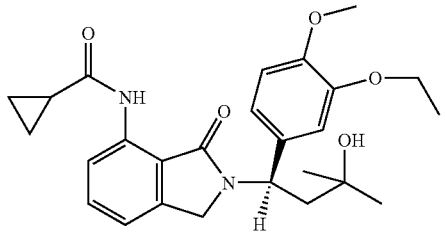

Step 1: To a solution of (1R)-[1-(3-ethoxy-4-methoxy-phenyl)-3-oxo-butyl]-carbamic acid tert-butyl ester (1 g, 3 mmol) in THF (10 mL) was added a solution of methyl lithium (4 mL, 3M, 12 mmol) at 0° C. To the mixture was added methanol (5 mL). The residue was extracted with ethyl acetate (50 mL) and NH$_4$Cl (sat, 25 mL). The organic layer was washed with brine (100 mL) and dried over MgSO$_4$. The solvent was removed in vacuo. The residue was purified with preparative HPLC to give (R)-[1-(3-ethoxy-4-methoxy-phenyl)-3-hydroxy-3-methyl-butyl]-carbamic acid tert-butyl ester (150 mg, 14% yield).

Step 2: To a solution of (1R)-[1-(3-ethoxy-4-methoxy-phenyl)-3-hydroxy-3-methyl-butyl]-carbamic acid tert-butyl ester (150 mg, 0.42 mmol) in methylene chloride (5 mL) was added a solution of HCl in dioxane (0.5 mL, 4N, 2 mmol). After 2 hrs, the solvent was removed and the crude oil was used in the next step without further purification. A mixture of the resulted oil, 2-bromomethyl-6-(cyclopropanecarbonyl-amino)-benzoic acid methyl ester (130 mg, 0.42 mmol) and triethyl amine (0.12 mL, 0.86 mmol) in DMF (3 mL) was heated at 80° C. for 27 hrs. The solvent was removed in vacuo. The residue was extracted with ethyl acetate (50 mL) and 1N HCl (50 mL). The organic layer was washed with 1N HCl (50 mL), brine (50 mL), and dried over MgSO$_4$. The solvent was removed in vacuo. The residue was purified with Preparative HPLC to give (1R)-cyclopropanecarboxylic acid {2-[1-(3-ethoxy-4-methoxy-phenyl)-3-hydroxy-3-methyl-butyl]-3-oxo-2,3-dihydro-1H-isoindol-4-yl}-amide (100 mg, 51% yield): mp, 90-92° C.; $^1$H NMR (CDCl$_3$) δ 0.85-0.93 (m, 2H, CH$_2$), 1.08-1.13 (m, 2H, CH$_2$), 1.25 (s, 3H, CH$_3$), 1.34 (s, 3H, CH$_3$), 1.45 (t, J=7 Hz, 3H, CH$_3$), 1.67-1.74 (m, 1H, CH), 2.18 (dd, J=4, 14 Hz 1H, CHH), 2.32 (dd, J=9, 14 Hz, 1H, CHH), 2.38 (s, 1H, OH), 3.86 (s, 3H, CH$_3$), 3.94 (d, J=17 Hz, 1H, NCHH), 4.07 (q, J=7 Hz, 2H, CH$_2$), 4.36 (d, J=17 Hz, 1H, NCHH), 5.70 (dd, J=4, 9 Hz, 1H, NCH), 6.82-6.99 (m, 4H, Ar), 7.41 (t, J=8 Hz, 1H, Ar), 8.42 (d, J=8 Hz, 1H, Ar), 10.58 (s, 1H, NH); $^{13}$C NMR (CDCl$_3$) δ 8.27, 14.78, 16.19, 29.98, 30.22, 43.95, 46.13, 50.96, 55.98, 64.60, 70.02, 111.43, 112.90, 116.71, 117.51, 117.69, 119.72, 132.48, 133.16, 137.99, 141.50, 148.50, 149.12, 169.63, 172.72; Anal Calcd for C$_{26}$H$_{32}$N$_2$O$_5$+1.1H$_2$O: C, 66.11; H, 7.30; N, 5.93. Found: C, 65.73; H, 6.90; N, 5.82.

5.24. Example 24

(1R)-Cyclopropanecarboxylic acid {2-[2-cyclopropanecarbonyloxycarbamoyl-1-(3-ethoxy-4-methoxy-phenyl)-ethyl]-3-oxo-2,3-dihydro-1H-isoindol-4-yl}-amide

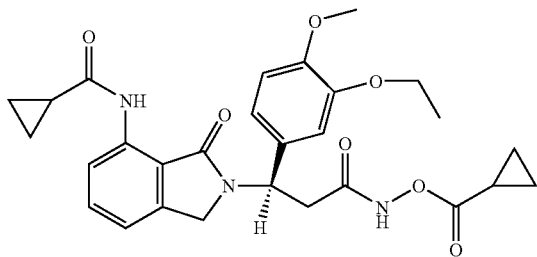

To a solution of (1R)-cyclopropanecarboxylic acid {2-[1-(3-ethoxy-4-methoxy-phenyl)-2-hydroxycarbamoyl-ethyl]-3-oxo-2,3-dihydro-1H-isoindol-4-yl}-amide (500 mg, 1.1 mmol) in acetonitrile (5 mL) was added cyclopropanecarbonyl chloride (0.15 mL, 1.7 mmol) at room temperature and kept for 24 hrs. The solution was extracted with ethyl acetate (50 mL) and sodium hydrogen carbonate (50 mL, sat). The organic layer was dried over MgSO$_4$. Filtration and removal of solvent gave (1R)-cyclopropanecarboxylic acid {2-[2-cyclopropanecarbonyloxycarbamoyl-1-(3-ethoxy-4-methoxy-phenyl)-ethyl]-3-oxo-2,3-dihydro-1H-isoindol-4-yl}-amide (380 mg, 66% yield): mp, 130-132° C.; $^1$H NMR (DMSO-d$_6$) δ 0.81-1.01 (2 ms, 8H, 4-CH$_2$), 1.31 (t, J=7 Hz, 3H, CH$_3$), 1.70-1.80 (m, 1H, CH), 2.97-3.05 (m, 2H, CH$_2$), 3.73 (s, 3H, CH$_3$), 3.97-4.04 (m, 2H, CH$_2$), 4.17 (d, J=18 Hz, 1H, NCHH), 4.59 (d, J=18 Hz, 1H, NCHH), 5.66 (t, J=8 Hz, 1H, NCH), 6.87-6.94 (m, 3H, Ar), 7.18 (d, J=8 Hz, 1H, Ar), 7.49 (d, J=8 Hz, 1H, Ar), 8.23 (d, J=8 Hz, 1H, Ar), 10.54 (s, 1H, NH), 12.00 (s, 1H, NH); $^{13}$C NMR (DMSO-d$_6$) δ 7.77, 8.92, 10.28, 14.69, 15.46, 34.61, 46.60, 51.11, 55.48, 63.80, 111.94, 112.11, 116.81, 117.31, 117.49, 119.27, 131.22, 132.77, 136.96, 142.25, 147.94, 148.57, 166.59, 168.85, 171.72, 172.41; Anal Calcd for C$_{28}$H$_{31}$N$_3$O$_7$+0.7H$_2$O: C, 62.96; H, 6.11; N, 7.87. Found: C, 62.64; H, 5.89; N, 7.78.

5.25 Example 25

(1R)-Cyclopropanecarboxylic acid {2-[1-(3-ethoxy-4-methoxy-phenyl)-2-isobutyryloxycarbamoyl-ethyl]-3-oxo-2,3-dihydro-1H-isoindol-4-yl}-amide

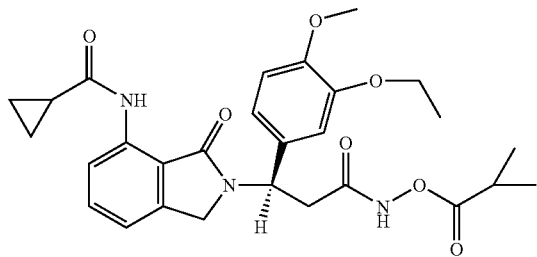

To a solution of (1R)-cyclopropanecarboxylic acid {2-[1-(3-ethoxy-4-methoxy-phenyl)-2-hydroxycarbamoyl-ethyl]-3-oxo-2,3-dihydro-1H-isoindol-4-yl}-amide (500 mg, 1.1 mmol) in acetonitrile (5 mL) was added isobutyryl chloride (0.15 mL, 1.4 mmol) at room temperature and kept for 24 hrs. The solution was extracted with ethyl acetate (50 mL) and sodium hydrogen carbonate (50 mL, sat). The organic layer was dried over MgSO$_4$. Filtration and removal of solvent gave (1R)-cyclopropanecarboxylic acid {2-[1-(3-ethoxy-4-methoxy-phenyl)-2-isobutyryloxycarbamoyl-ethyl]-3-oxo-2,3-dihydro-1H-isoindol-4-yl}-amide (380 mg, 66% yield): mp, 107-109° C.; $^1$H NMR (DMSO-d$_6$) δ 0.86-0.89 (m, 4H, 2CH$_2$), 1.10 (d, J=7 Hz, 6H, 2CH$_3$), 1.31 (t, J=7 Hz, 3H, CH$_3$), 1.73-1.81 (m, 1H, CH), 2.62-2.73 (m, 1H, CH), 3.02-3.05 (m, 2H, CH$_2$), 3.73 (s, 3H, CH$_3$), 3.96-4.05 (m, 2H, CH$_2$), 4.19 (d, J=18 Hz, 1H, NCHH), 4.59 (d, J=18 Hz, 1H, NCHH), 5.67 (t, J=8 Hz, 1H, NCH), 6.86-6.94 (m, 3H, Ar), 7.19 (d, J=8 Hz, 1H, Ar), 7.50 (d, J=8 Hz, 1H, Ar), 8.23 (d, J=8 Hz, 1H, Ar), 10.54 (s, 1H, NH), 11.86 (s, 1H, NH); $^{13}$C NMR (DMSO-d$_6$) δ 7.76, 14.69, 15.46, 18.65, 31.27, 34.64, 46.59, 51.07, 55.47, 63.80, 111.93, 112.09, 116.82, 117.32, 117.50, 119.27, 131.23, 132.77, 136.98, 142.25, 147.95, 148.58, 166.61, 168.04, 171.72, 174.29; Anal Calcd for C$_{28}$H$_{33}$N$_3$O$_7$+0.11 H$_2$O: C, 63.99; H, 6.37; N, 8.00; H$_2$O, 0.38. Found: C, 63.64; H, 6.37; N, 7.70; H$_2$O, 0.39.

5.26. Example 26

(1R)-Cyclopropanecarboxylic acid {2-[2-(2,2-dimethyl-propionyloxycarbamoyl)-1-(3-ethoxy-4-methoxy-phenyl)-ethyl]-3-oxo-2,3-dihydro-1H-isoindol-4-yl}-amide

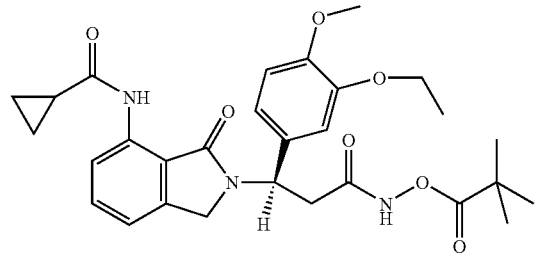

To a solution of (1R)-cyclopropanecarboxylic acid {2-[1-(3-ethoxy-4-methoxy-phenyl)-2-hydroxycarbamoyl-ethyl]-3-oxo-2,3-dihydro-1H-isoindol-4-yl}-amide (180 mg, 0.4 mmol) in acetonitrile (2 mL) was added 2,2-dimethyl-propionyl chloride (0.064 mL, 0.5 mmol) at room temperature and kept for 24 hrs. The solution was extracted with ethyl acetate (15 mL) and sodium hydrogen carbonate (15 mL, sat). The organic layer was dried over MgSO$_4$. Filtration and removal of solvent gave (1R)-cyclopropanecarboxylic acid {2-[2-(2,2-dimethyl-propionyloxycarbamoyl)-1-(3-ethoxy-4-methoxy-phenyl)-ethyl]-3-oxo-2,3-dihydro-1H-isoindol-4-yl}-amide (90 mg, 42% yield): mp, 146-148° C.; $^1$H NMR (DMSO-d$_6$) δ 0.87-0.89 (m, 4H, 2CH$_2$), 1.19 (s, 9H, 3CH$_3$), 1.30 (t, J=7 Hz, 3H, CH$_3$), 1.76-1.82 (m, 1H, CH), 3.04 (d, J=8 Hz, 2H, CH$_2$), 3.73 (s, 3H, CH$_3$), 3.97-4.05 (m, 2H, CH$_2$), 4.19 (d, J=18 Hz, 1H, NCHH), 4.58 (d, J=18 Hz, 1H, NCHH), 5.66 (t, J=8 Hz, 1H, NCH), 6.87-6.94 (m, 3H, Ar), 7.19 (d, J=8 Hz, 1H, Ar), 7.50 (d, J=8 Hz, 1H, Ar), 8.23 (d, J=8 Hz, 1H, Ar), 10.55 (s, 1H, NH), 11.82 (s, 1H, NH); $^{13}$C NMR (DMSO-d$_6$) δ 7.77, 14.69, 15.46, 26.71, 34.63, 37.63, 46.61, 51.03, 55.46, 63.78, 111.91, 112.07, 116.82, 117.32, 117.51, 119.24, 131.24, 132.76, 136.96, 142.24, 147.92, 148.55, 166.66, 168.00, 171.71, 175.41; Anal Calcd for C$_{29}$H$_{35}$N$_3$O$_7$: C, 64.79; H, 6.56; N, 7.82. Found: C, 64.91; H, 6.50; N, 7.84.

5.27 Example 27

(1R)-Cyclopropanecarboxylic acid {2-[2-(3,3-dimethyl-butyryloxycarbamoyl)-1-(3-ethoxy-4-methoxy-phenyl)-ethyl]-3-oxo-2,3-dihydro-1H-isoindol-4-yl}-amide

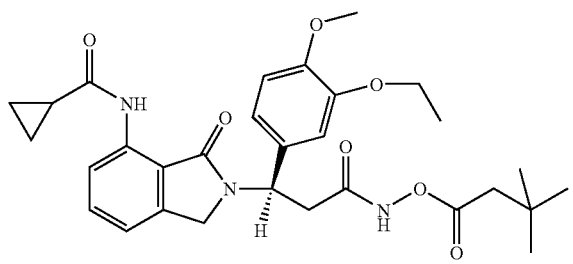

To a solution of (1R)-cyclopropanecarboxylic acid {2-[1-(3-ethoxy-4-methoxy-phenyl)-2-hydroxycarbamoyl-ethyl]-3-oxo-2,3-dihydro-1H-isoindol-4-yl}-amide (500 mg, 1.1 mmol) in acetonitrile (5 mL) was added 3,3-dimethyl-butyryl chloride (0.2 mL, 1.4 mmol) at room temperature and kept for 24 hrs. The solution was extracted with ethyl acetate (50 mL) and sodium hydrogen carbonate (50 mL, sat). The organic layer was dried over MgSO$_4$. Filtration and removal of solvent gave (1R)-cyclopropanecarboxylic acid {2-[2-(3,3-dimethyl-butyryloxycarbamoyl)-1-(3-ethoxy-4-methoxy-phenyl)-ethyl]-3-oxo-2,3-dihydro-1H-isoindol-4-yl}-amide (360 mg, 59% yield): mp, 118-120° C.; $^1$H NMR (DMSO-d$_6$) δ 0.87-0.89 (m, 4H, 2CH$_2$), 0.98 (s, 9H, 3CH$_3$), 1.31 (t, J=7 Hz, 3H, CH$_3$), 1.73-1.80 (m, 1H, CH), 2.27 (s, 2H, CH$_2$), 3.03-3.06 (m, 2H, CH$_2$), 3.73 (s, 3H, CH$_3$), 3.97-4.03 (m, 2H, CH$_2$), 4.18 (d, J=18 Hz, 1H, NCHH), 4.59 (d, J=18 Hz, 1H, NCHH), 5.67 (t, J=8 Hz, 1H, NCH), 6.86-6.94 (m, 3H, Ar), 7.18 (d, J=8 Hz, 1H, Ar), 7.49 (d, J=8 Hz, 1H, Ar), 8.22 (d, J=8 Hz, 1H, Ar), 10.55 (s, 1H, NH), 11.82 (s, 1H, NH); $^{13}$C NMR (DMSO-d$_6$) δ 7.75, 14.70, 15.46, 29.12, 30.53, 34.67, 44.24, 46.62, 51.11, 55.47, 63.80, 111.94, 112.09, 116.78, 117.33, 117.48, 119.25, 131.23, 132.73, 136.98, 142.26, 147.95, 148.56, 166.54, 168.06, 169.34, 171.70; Anal Calcd for C$_{30}$H$_{37}$N$_3$O$_7$+0.1H$_2$O: C, 65.11; H, 6.78; N, 7.59. Found: C, 64.87; H, 6.87; N, 7.48.

5.28. Example 28

(1S)-Cyclopropanecarboxylic acid {2-[1-(3-ethoxy-4-methoxy-phenyl)-2-methanesulfonyl-ethyl]-7-fluoro-3-oxo-2,3-dihydro-1H-isoindol-4-yl}-amide

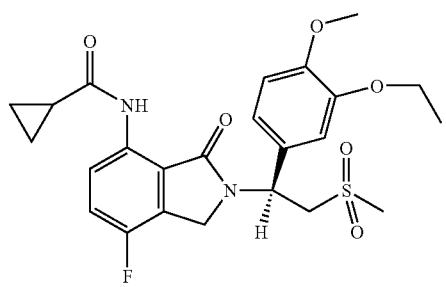

To a solution of 2-bromomethyl-6-(cyclopropanecarbonyl-amino)-3-fluoro-benzoic acid methyl ester (1 g, 3 mmol) and Et$_3$N (1.25 ml, 9 mmol) in DMF (10 ml) was added (1S)-1-(3-ethoxy-4-methoxy-phenyl)-2-methanesulfonyl-ethylamine (870 mg, 3.2 mmol). The mixture was heated at 90° C. for 20 hrs. The reaction mixture was cooled to room temperature and extracted with water (50 ml) and EtOAc (50 ml). The organic layer was washed with water (50 ml), brine (25 ml), dried over Na$_2$SO$_4$ and concentrated. The resulted oil was purified by chromatography to give (1S)-cyclopropanecarboxylic acid {2-[1-(3-ethoxy-4-methoxy-phenyl)-2-methanesulfonyl-ethyl]-7-fluoro-3-oxo-2,3-dihydro-1H-isoindol-4-yl}-amide as a white solid (800 mg, 55% yield): mp, 176-178° C.; $^1$H NMR (CDCl$_3$) δ 0.88-0.92 (m, 2H, c-propylCH$_2$), 1.09-1.12 (m, 2H, c-propylCH$_2$), 1.47 (t, J=7.0 Hz, 3H, OCH$_2$CH$_3$), 1.64-1.68 (m, 1H, c-propylCH), 2.98 (s, 3H, CH$_3$), 3.63-3.73 (m, 1H, CHHSO$_2$), 3.87 (s, 3H, CH$_3$), 4.05-4.28 (m, 4H, CHHSO$_2$+CNHH+OCH$_2$CH$_3$), 4.49 (d, J=18 Hz, 1H, CHHN), 6.85-6.92 (m, 1H, NCH), 6.86-6.93 (m, 3H, Ar), 7.04 (t, J=8 Hz, 1H, Ar), 8.45-8.55 (m, 1H, Ar), 10.32 (s, 1H, NHCO); $^{13}$C NMR (CDCl$_3$) δ 8.26, 8.27, 14.67, 16.04, 41.50, 44.67, 51.30, 55.39, 55.96, 64.65, 111.63, 112.21, 118.95, 119.26, 119.68, 119.92, 126.43, 126.74, 128.99, 134.48, 134.53, 148.98, 149.88, 150.31, 154.22, 168.89, 172.39. Anal Calcd for C$_{24}$H$_{27}$FN$_2$O$_6$S: C, 58.76; H, 5.55; N, 5.71. Found: C, 58.60; H, 5.33; N, 5.65.

5.29. Example 29

(1S)-3-{7-Chloro-2-[1-(3-ethoxy-4-methoxy-phenyl)-2-methanesulfonyl-ethyl]-3-oxo-2,3-dihydro-1H-isoindol-4-yl}-1,1-dimethyl-urea

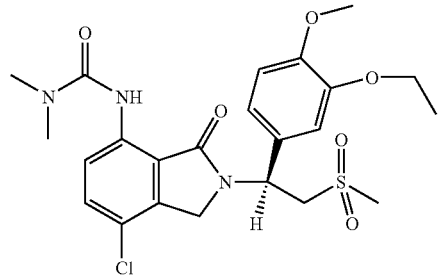

To (1S)-7-amino-4-chloro-2-[1-(3-ethoxy-4-methoxy-phenyl)-2-methanesulfonyl-ethyl]-2,3-dihydro-isoindol-1-one (800 mg, 1.82 mmol) was added dimethylcarbamyl chloride (3 ml). The mixture was heated at 100° C. for 20 hrs. The reaction mixture was cooled to room temperature and extracted with water (50 ml) and EtOAc (50 ml). The organic layer was washed with water (50 ml), brine (25 ml), dried over Na$_2$SO$_4$ and concentrated. The resulted oil was purified by chromatography to give (1S)-3-{7-chloro-2-[1-(3-ethoxy-4-methoxy-phenyl)-2-methanesulfonyl-ethyl]-3-oxo-2,3-dihydro-1H-isoindol-4-yl}-1,1-dimethyl-urea as a white solid (600 mg, 70% yield): mp, 205-207° C.; $^1$H NMR (CDCl$_3$) δ 1.47 (t, J=7.0 Hz, 3H, OCH$_2$CH$_3$), 2.94 (s, 3H, CH$_3$), 3.11 (s, 6H, N(CH$_3$)$_2$), 3.72 (dd, J=5, 15 Hz, 1H, CHHSO$_2$), 3.88 (s, 3H, CH$_3$), 4.05-4.22 (m, 4H, CHHSO$_2$+CHHN+OCH$_2$CH$_3$), 4.40 (d, J=10 Hz, 1H, CHHN), 5.73-5.79 (m, 1H, NCH), 6.86-6.96 (m, 3H, Ar), 7.36 (d, J=9 Hz, 1H, Ar), 8.35 (d, J=9 Hz, 1H, Ar), 9.77 (s, 1H, NHCO); $^{13}$C NMR (CDCl$_3$) δ 14.68, 36.27, 41.51, 46.96, 51.47, 55.73, 55.97, 64.64, 111.64, 111.67, 112.28, 118.20, 118.54, 119.31, 120.08, 129.13, 133.24, 138.58, 138.77, 148.94, 149.88, 155.01, 169.72. Anal Calcd for C$_{23}$H$_{28}$ClN$_3$O$_6$S: C, 54.32; H, 5.65; N, 8.12. Found: C, 54.16; H, 5.42; N, 7.82.

5.30 Example 30

(1S)—N-{7-Chloro-2-[1-(3-ethoxy-4-methoxy-phenyl)-2-methanesulfonyl-ethyl]-3-oxo-2,3-dihydro-1H-isoindol-4-yl}-2-(4-methyl-piperazin-1-yl)-acetamide

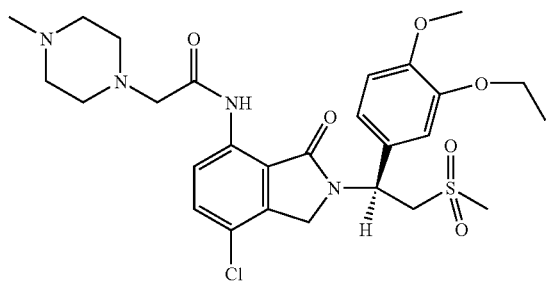

To a solution of (1S)-2-chloro-N-{7-chloro-2-[1-(3-ethoxy-4-methoxy-phenyl)-2-methanesulfonyl-ethyl]-3-oxo-2,3-dihydro-1H-isoindol-4-yl}-acetamide (250 mg, 0.48 mmol) in CH$_3$CN (10 ml) was added 1-methylpiperazine (0.21 ml, 1.9 mmol). The mixture was heated at 70° C. for 2 hrs. The reaction mixture was concentrated on rota-vap and extracted with water (50 ml) and EtOAc (50 ml). The organic layer was washed with water (50 ml), brine (25 ml), dried over Na$_2$SO$_4$ and concentrated. The resulted oil was purified by chromatography to give (1S)—N-{7-chloro-2-[1-(3-ethoxy-4-methoxy-phenyl)-2-methanesulfonyl-ethyl]-3-oxo-2,3-dihydro-1H-isoindol-4-yl}-2-(4-methyl-piperazin-1-yl)-acetamide as a white solid (70 mg, 25% yield): mp, 205-207° C.; $^1$H NMR (CDCl$_3$) δ 1.47 (t, J=7.0 Hz, 3H, OCH$_2$CH$_3$), 2.36 (s, 3H, CH$_3$), 2.64 (broad, 8H, CH$_2$ on piperazine ring), 2.99 (S, 3H, NCH$_3$), 3.21 (d, J=2 Hz, 2H, CH$_2$NCO), 3.73 (dd, J=5, 15 Hz, 1H, CHHSO$_2$), 3.88 (s, 3H, OCH$_3$), 4.05-4.20 (m, 4H, CHHSO$_2$+CNHH+OCH$_2$CH$_3$), 4.39 (d, J=15 Hz, 1H, CHHN), 5.74-5.80 (m, 1H, NCH), 6.86-6.98 (m, 3H, Ar), 7.40 (d, J=8 Hz, 1H, Ar), 8.55 (d, J=8 Hz, 1H, Ar), 11.45 (s, 1H, NHCO); $^{13}$C NMR (CDCl$_3$) δ 14.73, 41.37, 46.11, 46.81, 51.57, 53.46, 54.81, 55.76, 55.98, 62.18, 64.62, 111.61, 112.42, 119.46, 119.77, 119.87, 122.32, 129.20, 132.95, 135.98, 139.21, 148.93, 149.87, 168.50, 170.01. Anal Calcd for C$_{27}$H$_{35}$ClN$_4$O$_6$S: C, 56.00; H, 6.09; N, 9.67. Found: C, 55.82; H, 5.79; N, 9.42.

5.31 Example 31

(1S)—N-{7-Chloro-2-[1-(3-ethoxy-4-methoxy-phenyl)-2-methanesulfonyl-ethyl]-3-oxo-2,3-dihydro-1H-isoindol-4-yl}-2-morpholin-4-yl-acetamide; hydrochloride

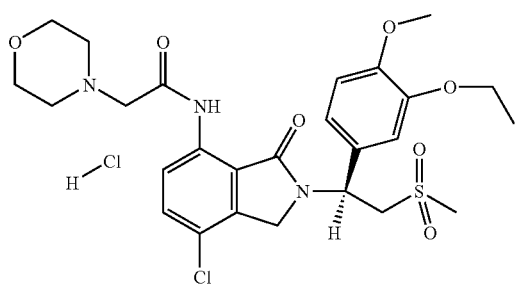

To a solution of (1S)-2-chloro-N-{7-chloro-2-[1-(3-ethoxy-4-methoxy-phenyl)-2-methanesulfonyl-ethyl]-3-oxo-2,3-dihydro-1H-isoindol-4-yl}-acetamide (250 mg, 0.48 mmol) in CH$_3$CN (10 ml) was added morpholine (0.17 ml, 1.94 mmol). The mixture was heated at 70° C. for 2 hrs. The reaction mixture was concentrated on rota-vap and extracted with water (50 ml) and EtOAc (50 ml). The organic layer was washed with water (50 ml), brine (25 ml), dried over Na$_2$SO$_4$ and concentrated. The resulted oil was purified by chromatography to give an oil which was stirred with HCl in ether (3 ml) to give (1S)—N-{7-chloro-2-[1-(3-ethoxy-4-methoxy-phenyl)-2-methanesulfonyl-ethyl]-3-oxo-2,3-dihydro-1H-isoindol-4-yl}-2-morpholin-4-yl-acetamide; hydrochloride as a white solid (200 mg, 68% yield): mp, 198-200° C.; $^1$H NMR (CDCl$_3$ with D$_2$O added) δ 1.46 (t, J=7.0 Hz, 3H, OCH$_2$CH$_3$), 2.68 (broad, 4H, CH$_2$NCH$_2$ on morpholino ring), 2.99 (s, 3H, SCH$_3$), 3.24 (broad, 2H, CH$_2$NCO), 3.72 (dd, J=5, 15 Hz, 1H, CHHSO$_2$), 3.87-3.92 (m, 7H, OCH$_3$+CH$_2$OCH$_2$ on morpholine ring), 4.05-4.23 (m, 4H, CHHSO$_2$+CNHH+OCH$_2$CH$_3$), 4.40 (d, J=15 Hz, 1H, CHHN), 5.71-5.77 (m, 1H, NCH), 6.86-6.97 (m, 3H, Ar), 7.40 (d, J=8 Hz, 1H, Ar), 8.52 (d, J=8 Hz, 1H, Ar); $^{13}$C NMR (CDCl$_3$) δ 14.75, 41.71, 47.09, 51.22, 51.59, 55.09, 56.02, 63.81, 64.10, 64.81, 105.68, 111.67, 112.28, 119.32, 120.0, 120.27, 124.03, 128.81, 133.20, 134.72, 139.41, 149.09, 150.01, 168.55. Anal Calcd for C$_{26}$H$_{33}$Cl$_2$N$_3$O$_7$S+0.53H$_2$O: C, 51.02; H, 5.61; N, 6.87. Found: C, 50.70; H, 5.38; N, 6.76, 0.98% H$_2$O.

5.32 Example 32

(1S)—N-{7-Chloro-2-[1-(3-ethoxy-4-methoxy-phenyl)-2-methanesulfonyl-ethyl]-3-oxo-2,3-dihydro-1H-isoindol-4-yl}-2-dimethylamino-acetamide; hydrochloride

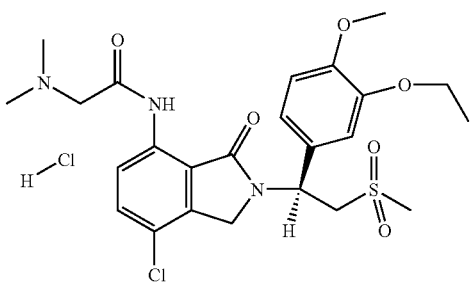

To a solution of (1S)-2-chloro-N-{7-chloro-2-[1-(3-ethoxy-4-methoxy-phenyl)-2-methanesulfonyl-ethyl]-3-oxo-2,3-dihydro-1H-isoindol-4-yl}-acetamide (400 mg, 0.78 mmol) in CH₃CN (10 ml) was added dimethylamine (2N in MeOH, 1.6 ml, 3.2 mmol). The mixture was heated at 70° C. for 2 hrs. The reaction mixture was concentrated on rota-vap and extracted with water (50 ml) and EtOAc (50 ml). The organic layer was washed with water (50 ml), brine (25 ml), dried over Na₂SO₄ and concentrated. The resulted oil was purified by chromatography to give an oil which was stirred with HCl in ether (3 ml) to give (1S)—N-{7-chloro-2-[1-(3-ethoxy-4-methoxy-phenyl)-2-methanesulfonyl-ethyl]-3-oxo-2,3-dihydro-1H-isoindol-4-yl}-2-dimethylamino-acetamide; hydrochloride as a white solid (300 mg, 68% yield): mp, 198-200° C.; ¹H NMR (DMSO-d₆) δ 1.32 (t, J=7.5 Hz, 3H, OCH₂CH₃), 2.87 (s, 6H, N(CH₃)₂), 3.04 (s, 3H, CH₃), 3.74 (s, 3H, CH₃), 3.94-4.16 (m, 4H, OCH₂CH₃+NCHH+CHHSO₂), 4.36-4.50 (m, 3H, CHHSO₂+CH₂NCO), 4.73 (d, J=18 Hz, 1H, CHHN), 5.85-5.91 (m, 1H, NCH), 6.98 (s, 2H, Ar), 7.05 (s, 1H, Ar), 7.69 (d, J=8 Hz, 1H, Ar), 8.18 (d, J=8 Hz, 1H, Ar), 10.21 (bs, 1H, HCl); 10.45 (s, 1H, NHCO); ¹³C NMR (DMSO-d6) δ 15.17, 23.25, 41.51, 43.86, 46.03, 49.41, 53.88, 56.00, 58.52, 64.41, 112.50, 112.80, 120.23, 121.25, 123.33, 130.22, 133.21, 134.72, 140.60, 148.55, 149.46, 154.53, 167.02, 180.13, Anal Calcd for C₂₄H₃₁Cl₂N₃O₆S+ 0.41 H₂O: C, 50.78; H, 5.65; N, 7.40. Found: C, 50.81; H, 5.55; N, 7.18, H₂O, 1.30.

5.33. Example 33

50 mg Solid Tablets

Tablets, each containing 50 mg of (1R)-Cyclopropanecarboxylic acid {2-[2-carbamoyl-1-(3-ethoxy-4-methoxy-phenyl)-ethyl]-7-chloro-3-oxo-2,3-dihydro-1H-isoindol-4-yl}-amide, can be prepared in the following manner:

| Constitutuents (for 1000 tablets) | |
|---|---|
| (1R)-Cyclopropanecarboxylicn acid {2-[2-carbamoyl-1-(3-ethoxy-4-methoxy-phenyl)-ethyl]-7-chloro-3-oxo-2,3-dihydro-1H-isoindol-4-yl}-amide | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

5.34. Example 34

100 mg Solid Tablets

Tablets, each containing 100 mg of (1R)-Cyclopropanecarboxylic acid {2-[2-carbamoyl-1-(3-ethoxy-4-methoxy-phenyl)-ethyl]-7-chloro-3-oxo-2,3-dihydro-1H-isoindol-4-yl}-amide, can be prepared in the following manner:

| Constitutuents (for 1000 tablets) | |
|---|---|
| (1R)-Cyclopropanecarboxylicn acid {2-[2-carbamoyl-1-(3-ethoxy-4-methoxy-phenyl)-ethyl]-7-chloro-3-oxo-2,3-dihydro-1H-isoindol-4-yl}-amide | 100.0 g |
| lactose | 100.0 g |
| wheat starch | 47.0 g |
| magnesium stearate | 3.0 g |

All the solid ingredients are first forced through a sieve of 0.6 mm mesh width. The active ingredient, lactose, magnesium stearate and half of the starch then are mixed. The other half of the starch is suspended in 40 mL of water and this suspension is added to 100 mL of boiling water. The resulting paste is added to the pulverised substances and the mixture is granulated, if necessary with the addition of water. The granulate is dried overnight at 35° C., forced through a sieve of 1.2 mm mesh width and compressed to form tablets of approximately 6 mm diameter which are concave on both sides.

5.35. Example 35

75 mg Chewable Tablets

Tablets for chewing, each containing 75 mg of (1R)-Cyclopropanecarboxylic acid {2-[2-carbamoyl-1-(3-ethoxy-4-methoxy-phenyl)-ethyl]-7-chloro-3-oxo-2,3-dihydro-1H-isoindol-4-yl}-amide, can be prepared in the following manner:

| Composition (for 1000 tablets) | |
|---|---|
| (1R)-Cyclopropanecarboxylicn acid {2-[2-carbamoyl-1-(3-ethoxy-4-methoxy-phenyl)-ethyl]-7-chloro-3-oxo-2,3-dihydro-1H-isoindol-4-yl}-amide | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatin solution | q.s. |

All the solid ingredients are first forced through a sieve of 0.25 mm mesh width. The mannitol are the lactose are mixed, granulated with the addition of gelatin solution, forced through a sieve of 2 mm mesh width, dried at 50° C. and again forced through a sieve of 1.7 mm mesh width (1R)-Cyclopropanecarboxylic acid {2-[2-carbamoyl-1-(3-ethoxy-4-methoxy-phenyl)-ethyl]-7-chloro-3-oxo-2,3-dihydro-1H-isoindol-4-yl}-amide, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

5.36. Example 36

10 mg Tablets

Tablets, each containing 10 mg (1R)-Cyclopropanecarboxylic acid {2-[2-carbamoyl-1-(3-ethoxy-4-methoxy-phenyl)-ethyl]-7-chloro-3-oxo-2,3-dihydro-1H-isoindol-4-yl}-amide, can be prepared in the following manner:

| Composition (for 1000 tablets) | |
|---|---:|
| (1R)-Cyclopropanecarboxylicn acid {2-[2-carbamoyl-1-(3-ethoxy-4-methoxy-phenyl)-ethyl]-7-chloro-3-oxo-2,3-dihydro-1H-isoindol-4-yl}-amide | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralized water | q.s. |

The solid ingredients are first forced through a sieve of 0.6 mm mesh width. Then the active amide ingredient, lactose, talc, magnesium stearate and half of the starch are intimately mixed. The other half of the starch is suspended in 65 mL and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

5.37. Example 37

100 mg Gelatin Capsules

Gelatin dry-filled capsules, each containing 100 (1R)-Cyclopropanecarboxylic acid {2-[2-carbamoyl-1-(3-ethoxy-4-methoxy-phenyl)-ethyl]-7-chloro-3-oxo-2,3-dihydro-1H-isoindol-4-yl}-amide, can be prepared in the following manner:

| Composition (for 1000 tablets) | |
|---|---:|
| (1R)-Cyclopropanecarboxylicn acid {2-[2-carbamoyl-1-(3-ethoxy-4-methoxy-phenyl)-ethyl]-7-chloro-3-oxo-2,3-dihydro-1H-isoindol-4-yl}-amide | 100.0 g |
| microcrystalline cellulose | 30.0 g |
| sodium lauryl sulfate | 2.0 g |
| magnesium stearate | 8.0 g |

The sodium lauryl sulfate is sieved into (1R)-Cyclopropanecarboxylic acid {2-[2-carbamoyl-1-(3-ethoxy-4-methoxy-phenyl)-ethyl]-7-chloro-3-oxo-2,3-dihydro-1H-isoindol-4-yl}-amide through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

5.38. Example 27

Injectable Solution

A 0.2% injection or infusion solution can be prepared, for example, in the following manner:

| | |
|---|---:|
| (1R)-Cyclopropanecarboxylicn acid {2-[2-carbamoyl-1-(3-ethoxy-4-methoxy-phenyl)-ethyl]-7-chloro-3-oxo-2,3-dihydro-1H-isoindol-4-yl}-amide | 5.0 g |
| sodium chloride | 22.5 g |
| phosphate buffer pH 7.4 | 300.0 g |
| demineralized water | to 2500.0 mL |

(1R)-Cyclopropanecarboxylic acid {2-[2-carbamoyl-1-(3-ethoxy-4-methoxy-phenyl)-ethyl]-7-chloro-3-oxo-2,3-dihydro-1H-isoindol-4-yl}-amide is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of amide).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating leukemia comprising administering to a patient a therapeutically effective amount of (1R)-cyclopropanecarboxylic acid {2-[2-carbamoyl-1-(3-ethoxy-4-methoxy-phenyl)-ethyl]-7-chloro-3-oxo-2,3-dihydro-1H-isoindol-4-yl}-amide:

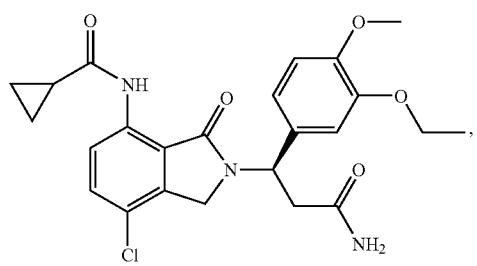

or a pharmaceutically acceptable salt or solvate thereof.

2. The method of claim 1, wherein the leukemia is chronic lymphocytic leukemia.

3. The method of claim 1, wherein the leukemia is acute lymphoblastic leukemia.

* * * * *